(12) United States Patent
Chung et al.

(10) Patent No.: US 8,940,739 B2
(45) Date of Patent: Jan. 27, 2015

(54) COMPOUND OF A REVERSE-TURN MIMETIC AND A PRODUCTION METHOD AND USE THEREFOR

(75) Inventors: Jae-Uk Chung, Cheongju-si (KR); Mi-Jung Kim, Suwon-si (KR); Yong-Sil Lee, Hwaseong-si (KR); Sang-Ho Ma, Suwon-si (KR); Young-Seok Cho, Hwaseong-si (KR); Sang-Hak Lee, Hwaseong-si (KR); Young-Jun Na, Yongin-si (KR); Myoung-Joo Kang, Hwaseong-si (KR); Woul-Seong Park, Suwon-si (KR)

(73) Assignee: JW Pharmaceutical Corporation, Seoul (KR)

( * ) Notice: Subject to any disclaimer, the term of this patent is extended or adjusted under 35 U.S.C. 154(b) by 0 days.

(21) Appl. No.: 13/878,990

(22) PCT Filed: Oct. 14, 2011

(86) PCT No.: PCT/KR2011/007667
§ 371 (c)(1),
(2), (4) Date: Apr. 11, 2013

(87) PCT Pub. No.: WO2012/050393
PCT Pub. Date: Apr. 19, 2012

(65) Prior Publication Data
US 2013/0196972 A1     Aug. 1, 2013

(30) Foreign Application Priority Data
Oct. 14, 2010   (KR) ........................ 10-2010-0100490

(51) Int. Cl.
*A01N 43/64* (2006.01)
*A61K 31/53* (2006.01)
*C07D 487/12* (2006.01)

(52) U.S. Cl.
USPC ........................................................ 514/243

(58) Field of Classification Search
USPC .......................................... 514/243; 544/184
See application file for complete search history.

(56) References Cited

U.S. PATENT DOCUMENTS

| | | | |
|---|---|---|---|
| 5,440,013 A | 8/1995 | Kahn | |
| 5,929,237 A | 7/1999 | Kahn | |
| 6,013,458 A | 1/2000 | Kahn et al. | |
| 6,762,185 B1 | 7/2004 | Kahn et al. | |
| 7,008,941 B2 | 3/2006 | Urban et al. | |
| 7,232,822 B2 | 6/2007 | Moon et al. | |
| 7,531,320 B2 | 5/2009 | Kahn et al. | |
| 7,563,825 B1 | 7/2009 | Kahn | |
| 7,566,711 B2 | 7/2009 | Moon et al. | |
| 7,576,084 B2 | 8/2009 | Moon et al. | |
| 7,585,862 B2 | 9/2009 | Moon et al. | |
| 7,662,960 B2 | 2/2010 | Kahn et al. | |
| 7,671,054 B1* | 3/2010 | Moon et al. | 514/243 |
| 7,932,384 B2 | 4/2011 | Moon et al. | |
| 8,049,008 B2 | 11/2011 | Chung et al. | |
| 8,080,657 B2* | 12/2011 | Chung et al. | 544/184 |
| 8,101,751 B2 | 1/2012 | Moon et al. | |
| 8,106,049 B2 | 1/2012 | Moon et al. | |
| 8,138,337 B2 | 3/2012 | Moon et al. | |
| 8,293,743 B2 | 10/2012 | Kahn | |
| 8,318,738 B2 | 11/2012 | Moon et al. | |
| 2004/0072831 A1 | 4/2004 | Moon et al. | |
| 2007/0128669 A1 | 6/2007 | Kahn | |
| 2007/0129353 A1 | 6/2007 | Kahn | |
| 2010/0267672 A1* | 10/2010 | Jung et al. | 514/81 |
| 2010/0286094 A1* | 11/2010 | Chung et al. | 514/81 |
| 2011/0257185 A1 | 10/2011 | Moon et al. | |

FOREIGN PATENT DOCUMENTS

| | | |
|---|---|---|
| CN | 102459271 A | 5/2012 |
| KR | 10-2010-0085107 A | 7/2010 |
| WO | 94/03494 A1 | 2/1994 |
| WO | 01/00210 A1 | 1/2001 |
| WO | 01/16135 A2 | 3/2001 |
| WO | 03/031448 A1 | 4/2003 |
| WO | 2004/093828 A2 | 11/2004 |
| WO | 2005/116032 A2 | 12/2005 |
| WO | 2007/139346 A1 | 12/2007 |
| WO | 2009/051397 A2 | 4/2009 |
| WO | 2010/120112 A2 | 10/2010 |

OTHER PUBLICATIONS

Pinedo et al (2001).*
McMahon et al (2001).*
Obrecht et al., "Novel Peptide Mimetic Building Blocks and Strategies for Efficient Lead Finding," *Advances in Medicinal Chemistry* 4:1-68,1999.

* cited by examiner

*Primary Examiner* — Paul V. Ward
(74) *Attorney, Agent, or Firm* — Seed IP Law Group PLLC

(57) ABSTRACT

This invention relates to novel compounds of reverse-turn mimetics, having pyrazino-triazinone as a basic framework, and a method of preparing the same, and the use thereof to treat diseases such as cancer, in particular, acute myeloid leukemia.

8 Claims, No Drawings

COMPOUND OF A REVERSE-TURN MIMETIC AND A PRODUCTION METHOD AND USE THEREFOR

TECHNICAL FIELD

The present invention relates to novel compounds of reverse-turn mimetics, a method of preparing the same, and the use thereof in the treatment of diseases, such as acute myeloid leukemia.

BACKGROUND ART

The random screening of molecules for their possible activity as therapeutic agents has been being done for many years, as a consequence of which a number of important drugs have been discovered. Recently, non-peptide compounds have been developed which mimic the secondary structure of reverse-turns found in biologically active proteins or peptides. For example, U.S. Pat. No. 5,440,013, and Published PCT Application Nos. WO 94/003494A1, WO 01/000210A1, and WO 01/016135A2, all to Kahn, each disclose conformationally constrained non-peptide compounds, which mimic the secondary structure of reverse-turns. In addition, U.S. Pat. Nos. 5,929,237 and 6,013,458 that is a continuation-in-part (CIP) thereof, both to Kahn, describe conformationally constrained compounds which mimic the secondary structure of reverse-turn regions of biologically active peptides and proteins. The synthesis and identification of conformationally constrained reverse-turn mimetics and the application thereof to diseases were reviewed by Obrecht (Advances in Med. Chem., 4, 1-68, 1999).

As mentioned above, significant advancements have been made in the synthesis and identification of conformationally constrained reverse-turn mimetics, and techniques have been developed and provided that synthesize and screen library members of small molecules which mimic the secondary structure of peptides, in order to identify bioactive library members. Accordingly, attempts have been made to seek conformationally constrained compounds and highly bioactive compounds which mimic the secondary structure of the reverse-turn regions of biologically active peptides and proteins. For instance, reverse-turn mimetics, methods of manufacturing the same and bioactivities thereof are disclosed in PCT Application Nos. WO 04/093828A2, WO 05/116032A2, and WO 07/139,346A1.

Although a great number of the reverse-turn mimetics mentioned above have been manufactured, efforts continue to be made to manufacture compounds applicable to the treatment of diseases such as cancer, etc.

Of particular mention is the effort that has been focused on the development of compounds which strongly block a Wnt signaling pathway to effectively suppress the growth of acute myeloid leukemia (AML) cancer cells which are known to have an activated Wnt signaling pathway.

Also, there is a need to develop methods of manufacturing highly bioactive compounds on a mass scale once they have been found.

DISCLOSURE OF INVENTION

Technical Problem

Accordingly, an object of the present invention is to provide novel compounds which are highly bioactive, and a method of preparing the same.

Another object of the present invention is to provide the use of such compounds as therapeutic agents having anti-cancer effects and the like, in particular, as agents to treat acute myeloid leukemia.

Technical Solution

In order to accomplish the above objects, the present invention provides a compound represented by Formula I below or a pharmaceutically acceptable salt thereof

[Formula I]

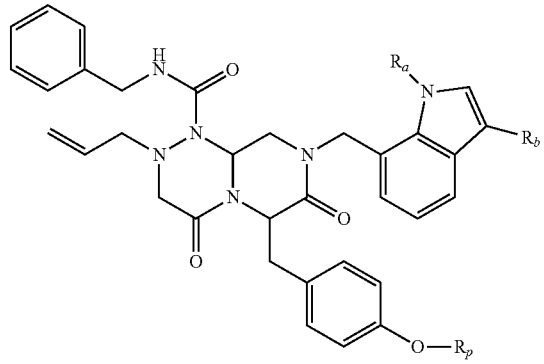

wherein, $R_a$ is $C_1$-$C_6$ alkyl group, $C_2$-$C_6$ alkenyl group, or $C_2$-$C_6$ alkynyl group;

$R_b$ is

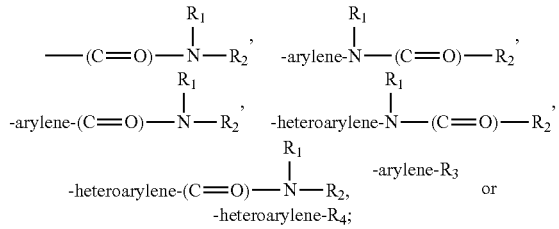

and wherein, $R_1$ is H, $C_1$-$C_{12}$ alkyl group or substituted $C_1$-$C_{12}$ alkyl group;

$R_2$ is H, aryl group, substituted aryl group, heteroaryl group, substituted heteroaryl group, heterocycloalkyl group, substituted heterocycloalkyl group, $C_1$-$C_{30}$ alkoxy group, substituted $C_1$-$C_{30}$ alkoxy group, $C_1$-$C_{30}$ alkyl group, substituted $C_1$-$C_{30}$ alkyl group, substituted or unsubstituted alkylamino group, substituted or unsubstituted arylamino group, substituted or unsubstituted heteroarylamino group, or substituted or unsubstituted amino group, $R_1$ and $R_2$ may be joined together to form an aliphatic ring, an aliphatic hetero ring, an aromatic ring, or an aromatic hetero ring or to form a spiro bond, in which the rings may optionally have at least one substituent;

$R_3$ is $C_1$-$C_{20}$ acyl group, substituted $C_1$-$C_{20}$ acyl group, cyano group or sulfonyl group;

$R_4$ is H, substituted or unsubstituted amino group, $C_1$-$C_{20}$ acyl group or substituted $C_1$-$C_{20}$ acyl group; and $R_p$ is H or a prodrug functional group.

Advantageous Effects

The present invention provides novel compounds of reverse-turn mimetics, a method of preparing the same, and the use thereof. According to the present invention, the novel compounds can effectively inhibit the proliferation of acute myeloid leukemia cancer cells in vitro, and also efficiently suppresses the growth of tumor in acute myeloid leukemia mouse model. Furthermore, the compounds of the present invention exhibit low CYP3A4 inhibitory activity, and superior hepatic metabolic stability.

The compounds of the present invention have high solubility and can thus be advantageously utilized as a drug even when they are not applied to the prodrug form.

Also, upon administration in vivo, the compounds of the present invention can exhibit superior efficacy even when they are injected in a smaller dose or the injection frequency thereof is low.

In the case where the method of preparing the compounds of the present invention is used, not only the compounds of Formula I but also reverse-turn mimetic structures can be mass produced on an industrial scale.

BEST MODE FOR CARRYING OUT THE INVENTION

Hereinafter, a detailed description will be given of the present invention.

The present invention provides a novel compound of reverse-turn mimetic represented by Formula I below or a pharmaceutically acceptable salt thereof, and thereby provides a compound useful as a therapeutic agent of acute myeloid leukemia or a pharmaceutically acceptable salt thereof

[Formula I]

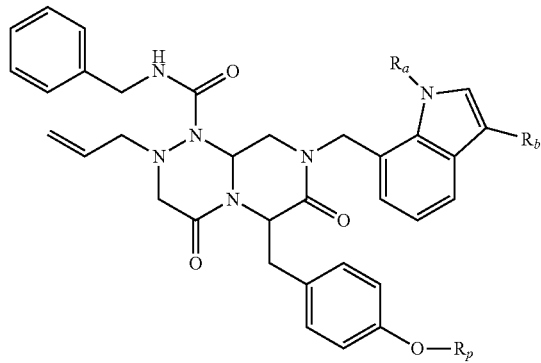

In Formula I, $R_a$ is $C_1$-$C_6$ alkyl group, $C_2$-$C_6$ alkenyl group, or $C_2$-$C_6$ alkynyl group; $R_b$ is

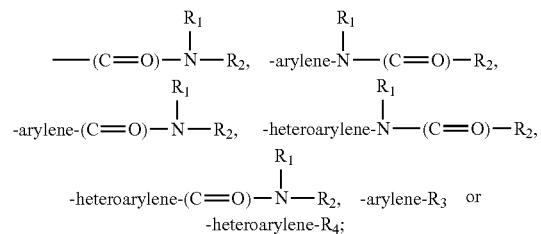

wherein, $R_1$ is H, $C_1$-$C_{12}$ alkyl group or substituted $C_1$-$C_{12}$ alkyl group; $R_2$ is H, aryl group, substituted aryl group, heteroaryl group, substituted heteroaryl group, heterocycloalkyl group, substituted heterocycloalkyl group, $C_1$-$C_{30}$ alkoxy group, substituted $C_1$-$C_{30}$ alkoxy group, $C_1$-$C_{30}$ alkyl group, substituted $C_1$-$C_{30}$ alkyl group, substituted or unsubstituted alkylamino group, substituted or unsubstituted arylamino group, substituted or unsubstituted heteroarylamino group, or substituted or unsubstituted amino group, $R_1$ and $R_2$ may be joined together to form an aliphatic ring, an aliphatic hetero ring, an aromatic ring, or an aromatic hetero ring or to form a spiro bond, in which the rings may optionally have at least one substituent; $R_3$ is $C_1$-$C_{20}$ acyl group, substituted $C_1$-$C_{20}$ acyl group, cyano group or sulfonyl group; and $R_4$ is H, substituted or unsubstituted amino group, $C_1$-$C_{20}$ acyl group or substituted $C_1$-$C_{20}$ acyl group; and $R_p$ is H or a prodrug functional group.

The prodrug functional group may include any functional group typically usable for a prodrug. Examples of any functional group include a phosphate functional group, a carboxyl functional group, a $C_1$-$C_6$ alkylamino functional group, an acylamino functional group, etc., and specific examples thereof include —$PO_3H_2$, —$HPO_3^-Na^+$, —$PO_3^{2-}Na_2^+$, —$PO_3^{2-}K_2^+$, —$PO_3^{2-}Mg^{2+}$, —

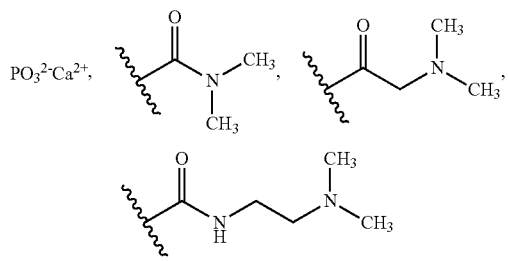

and so on.

$R_a$ may be $C_1$-$C_6$ alkyl group, $C_2$-$C_6$ alkenyl group, or $C_2$-$C_6$ alkynyl group, and preferably $C_1$-$C_6$ alkyl group.

$R_b$ may be

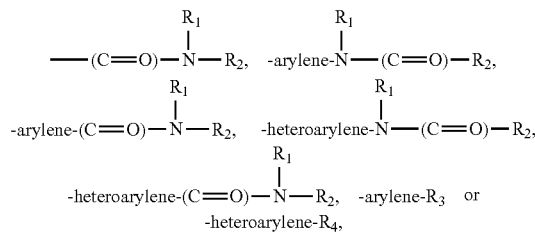

and preferably may be any one selected from the group consisting of

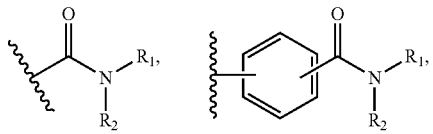

-continued

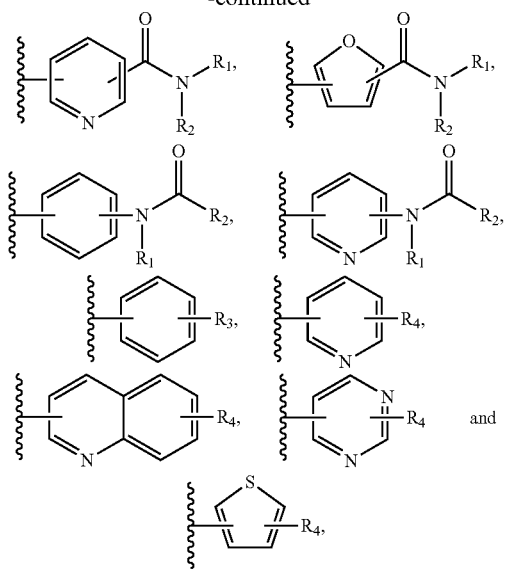

but is not limited thereto.

Furthermore, $R_1$ may be H, $C_1$-$C_{12}$ alkyl group or substituted $C_1$-$C_{12}$ alkyl group, and $R_2$ may be an aryl group, a substituted aryl group, a heteroaryl group, a substituted heteroaryl group, a heterocycloalkyl group, a substituted heterocycloalkyl group, a $C_1$-$C_{12}$ alkoxy group, a substituted $C_1$-$C_{12}$ alkoxy group, a $C_1$-$C_{12}$ alkyl group, a substituted $C_1$-$C_{12}$ alkyl group, a substituted or unsubstituted alkylamino group, a substituted or unsubstituted arylamino group, a substituted or unsubstituted heteroarylamino group, or a substituted or unsubstituted amino group, and $R_1$ and $R_2$ may be joined together to form an aliphatic ring, an aliphatic hetero ring, an aromatic ring or an aromatic hetero ring or to form a spiro bond, wherein the rings may have a substituent. Also, $R_3$ may be H, a $C_1$-$C_{20}$ acyl group, a substituted $C_1$-$C_{20}$ acyl group, a substituted or unsubstituted amino group, a cyano group or —$SO_2$—.

In the present invention, the alkyl group means a linear, branched or cyclic alkyl group.

In the present invention, the alkoxy group means a linear, branched or cyclic alkoxy group.

The arylene or aryl group may be an aryl having 5~12 carbons, and may include monocyclic or bicyclic or tricyclic aryls, but is not necessarily limited thereto.

The heteroarylene or heteroaryl group may be a heteroaryl having 2~11 carbons, and may include monocyclic or bicyclic or tricyclic heteroaryls, but is not necessarily limited thereto.

The heterocycloalkyl group may be a heterocycloalkyl group having 2~6 carbons, but is not necessarily limited thereto.

In the case where $R_1$, $R_2$, $R_3$ or $R_4$ is substituted with a substituent, examples of the substituent may include but are not limited to a substituted or unsubstituted alkyl group, a halogen-substituted alkyl group, a hydroxyl-substituted alkyl group, a substituted or unsubstituted aryl group, a substituted or unsubstituted heteroaryl group, a substituted or unsubstituted heterocycloalkyl group, a substituted or unsubstituted amino group, a substituted or unsubstituted alkoxy group, a substituted or unsubstituted carbonyl group, an acetyl group, a carboxyl group, a cyano group or —$SO_2$—.

Specifically, $R_1$ may be H or a $C_1$-$C_5$ alkyl group, wherein the $C_1$-$C_5$ alkyl group may be substituted with at least one Rq.

$R_2$ may be H, a $C_1$-$C_{10}$ alkyl group, a $C_3$-$C_{10}$ cycloalkyl group, an amino group, a $C_1$-$C_{10}$ alkoxy group, a benzyl group,

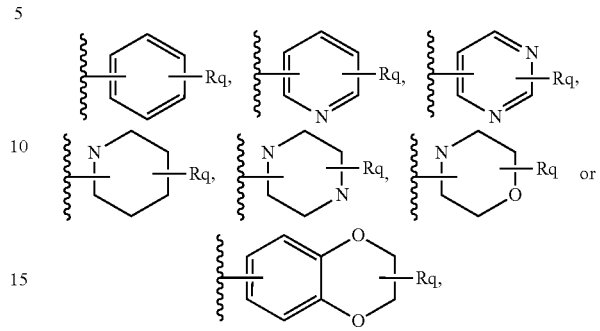

wherein the $C_1$-$C_{10}$ alkyl group, the $C_3$-$C_{10}$ cycloalkyl group, the amino group, the $C_1$-$C_{10}$ alkoxy group and the benzyl group may be substituted with at least one Rq.

$R_1$ and $R_2$ are fused with N, thus forming any one ring selected from among

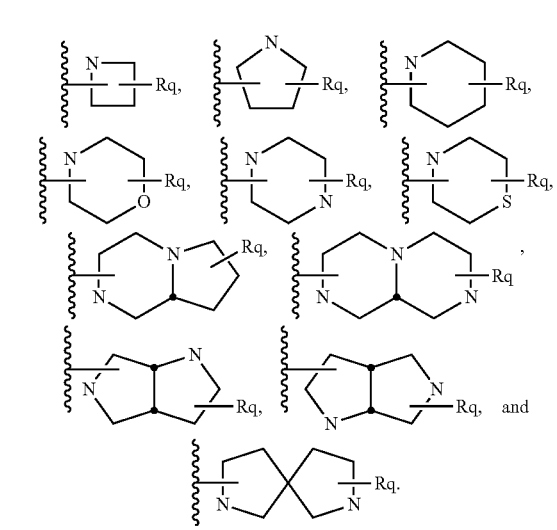

$R_3$ may be,

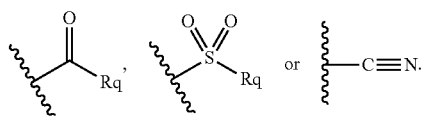

$R_4$ may be H, an amino group substituted with at least one Rq,

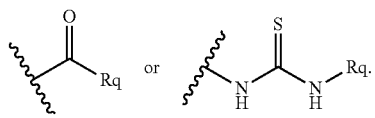

Rq may be H, at least one $C_1$-$C_{10}$ alkyl, substituted $C_1$-$C_{10}$ alkyl, $C_1$-$C_{10}$ cycloalkyl, substituted $C_1$-$C_{10}$ cycloalkyl, amino, substituted amino, $C_1$-$C_{10}$ alkoxy, substituted $C_1$-$C_{10}$ alkoxy, halogen, —OH, benzyl, substituted benzyl, acyl, substituted acyl, phenyl, substituted phenyl, butyl oxy carbonyl (BOC),

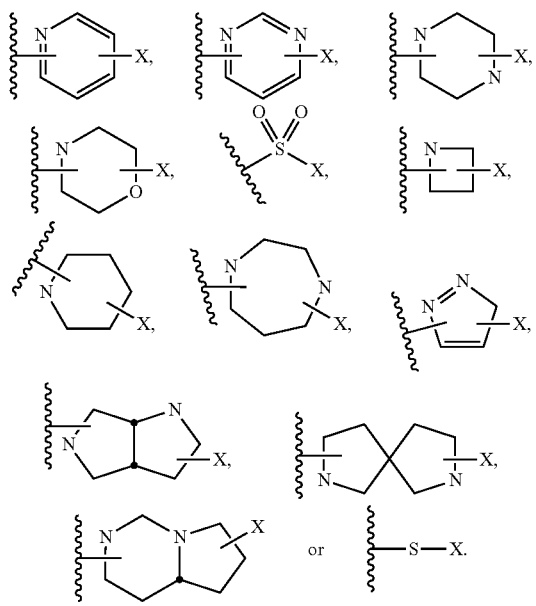

As such, X may be H, at least one $C_1$-$C_{10}$ alkyl, substituted $C_1$-$C_{10}$ alkyl, acyl, $C_3$-$C_{10}$ cycloalkyl, $C_1$-$C_{10}$ alkoxy, phenyl, substituted phenyl, benzyl, substituted benzyl, $C_1$-$C_{10}$ hetero aromatic ring, $C_3$-$C_{10}$ heterocycloalkyl, substituted $C_3$-$C_{10}$ heterocycloalkyl, amino, substituted amino or —OH.

The compounds according to the present invention have high solubility and may thus be advantageously utilized as a drug even without the development of the prodrug form.

Hence, a composition containing the compound of the present invention is favorably adapted to be provided in the form of an injection agent, such as an injectable pharmaceutical composition.

The present invention provides the preparation of a drug using the above compound, in order to treat diseases, particularly cancer, more particularly acute myeloid leukemia.

The compounds of the present invention are advantageous because (1) drug efficacy is good, (2) drug interactions are improved thus exhibiting better pharmaceutical activity, (3) they have high solubility and may thus be utilized as a drug even when they are not applied to the prodrug form, and (4) they have increased hepatic metabolic stability.

Specifically, the compounds of the present invention have lower CYP3A4 inhibitory activity (a higher IC50) compared to conventional compounds, thus improving drug interactions. Also, the compounds of the present invention may have stronger anti-proliferative activity (lower GI50) against acute myeloid leukemia cancer cells compared to conventional compounds, and thereby may be used to prevent or treat acute myeloid leukemia.

The solubility of the novel compounds of the present invention may be considerably increased because of structural improvements, and the compounds may be utilized as a drug even when they are not applied to the prodrug form.

Furthermore, the hepatic metabolic stability of the compounds of the present invention is increased, and thus, even when these compounds are injected in vivo in a smaller dose or they are injected at a lower frequency, they may manifest equal or superior efficacy compared to conventional compounds.

Examples of the compounds prepared in the present invention are listed in Tables 1 to 6 below, but the compounds of the present invention are not limited thereto.

TABLE 1

| No. | Chemical Formula | M.W. | NMR |
|---|---|---|---|
| A | 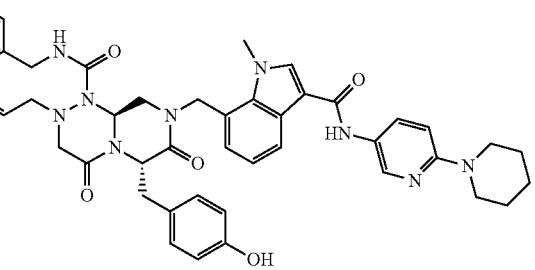 | 795.93 | 1H NMR (300 MHz, CDCl3-d, ppm, δ): 8.10~8.06 (m, 3H), 8.03~7.99 (m, 1H), 7.38 (d, J = 0.6 Hz, 1H), 7.31~7.22 (m, 2H), 7.15 (d, J = 6.9 Hz, 2H), 7.07 (t, J = 7.8 Hz, 1H), 6.98 (d, J = 4.8 Hz, 2H), 6.86 (d, J = 7.2 Hz, 1H), 6.75~6.68 (m, 4H), 5.61~5.52 (m, 1H), 5.31~5.27 (m, 2H), 5.07 (d, J = 10.2 Hz, 2H), 4.96~4.83 (m, 1H), 4.37-4.17 (m, 2H), 3.78 (s, 3H), 3.49~3.22 (m, 12H), 3.17~3.12 (m, 1H) |
| B | 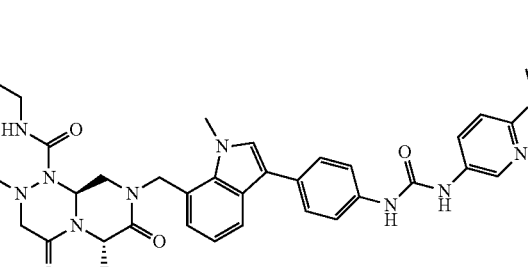 | 833.93 | (CDCl3, 300 MHz) δ 11.66 (bs, 1H), 8.43 (s, 1H), 8.28 (s, 1H), 7.77 (m, 2H), 7.64 (d, 2H, J = 7.8 HZ), 7.38 (m, 2H), 7.24~7.19 (m, 2H), 7.14 (m, 1H), 7.07 (s, 1H), 7.04 (d, 2H, J = 8.4 Hz), 6.90 (d, 2H, J = 7.2 Hz), 6.75 (d, 2H, J = 8.4 Hz), 6.70 (t, 1H, J = 5.7 Hz), 5.57 (m, 1H), 5.42~5.34 (m, 3H), 5.29 (d, 1H, J = 15.0 Hz), 5.18 (d, 1H, J = 15.0 Hz), 5.08 (d, 1H, J = 10.2 Hz), 4.90 (d, 1H, J = 17.1 Hz), 4.44 (dd, 1H, J = 15.0, 8.3 Hz), 4.32 (dd, 1H, J = 15.0, 6.0 Hz), 3.98 (s, 3H), 3.54~3.22 (m, 9H) |

TABLE 1-continued

| NO. | Chemical Formula | M.W. | NMR |
|---|---|---|---|
| C | | 803.91 | (CDCl3, 300 MHz) δ 8.01~7.87 (m, 3H), 7.75 (d, 1H, J = 8.1 Hz), 7.39~7.18 (m, 2H), 7.12 (s, 1H), 7.08-6.99 (m, 3H), 7.04 (d, 2H, J = 8.1 Hz), 6.95 (d, 2H, J = 10.5 Hz), 6.83-6.71 (m, 3H) 6.76 (s, 1H), 6.73 (d, 2H, J = 8.1 Hz), 5.61~5.47 (m, 3H), 5.44 (t, 1H, J = 4.8 Hz), 5.39~5.25 (m, 3H), 5.03~4.97 (m, 3H), 4.83 (d, 1H, J = 17.1 Hz), 4.43 (dd, 1H, J = 14.7, 6.3 Hz), 4.32 (dd, 1H, J = 15.6, 5.7 Hz), 3.94 (s, 3H), 3.91 (s, 3H), 3.56~3.18 (m, 9H) |

| NO. | Chemical Formula | M.W. | NMR |
|---|---|---|---|
| D-1 | | 781.90 | — |
| D-2 | | 794.94 | — |
| D-3 | | 794.94 | (CDCl3, 300 MHz) δ 7.87 (d, 1H, J = 8.1 Hz), 7.63 (d, 2H, J = 8.1 Hz), 7.49 (d, 2H, J = 8.1 Hz), 7.39~7.22 (m, 4H), 7.16 (s, 1H), 7.13 (t, 1H, J = 7.8 Hz), 7.05 (d, 2H, J = 8.4 Hz), 6.94 (d, 1H, J = 7.8 Hz), 6.70 (d, 2H, J = 7.5 Hz), 6.65 (m, 1H), 5.59~5.47 (m, 3H), 5.37 (t, 1H, J = 5.7 Hz), 5.02 (d, 1H J = 10.5 Hz), 4.94 (d, 1H, J = 15.0 Hz), 4.79 (d, 1H, J = 17.1 Hz), 4.47 (dd, 1H, J = 15.0, 6.3 Hz), 4.32 (dd, 1H, J = 15.0, 6.0 Hz), 4.01 (s, 3H), 3.91~3.47 (bd, 4H), 3.45~3.19 (m, 8H), 2.56-2.38 (bs, 4H), 2.34 (s, 3H) |

| No. | Chemical Formula | M.W. | NMR |
|---|---|---|---|
| D-4 | | 779.93 | — |
| D-5 | | 797.96 | — |
| D-6 | | 795.92 | — |
| D-7 | | 711.81 | — |
| D-8 | | 725.83 | — |

| No. | Chemical Formula | M.W. | NMR |
|---|---|---|---|
| D-9 | | 793.95 | — |
| D-10 | | 914.06 | (CD3CD, 300 MHz) δ 7.97 (d, 2H, J = 8.4 Hz), 7.88 (d, 1H, J = 7.8 Hz), 7.75 (d, 2H J = 8.4 Hz), 7.60 (d, 2H, J = 9.0 Hz), 7.48 (s, 1H), 7.33~6.90 (m, 1H), 6.69 (d, 2H, J = 8.4 Hz), 5.77~5.64 (m, 1H), 5.51~5.46 (m, 1H), 5.40~5.25 (m, 2H), 5.12~4.97 (m, 2H), 4.34~4.23 (m, 2H), 4.06 (s, 3H), 3.76~3.68 (m, 4H), 3.63~3.52 (m, 4H), 3.36~3.26 (m, 4H), 3.21~3.12 (m, 4H), 2.15 (s, 3H) |
| D-11 | | 886.05 | — |
| D-12 | | 874.00 | 1H NMR (300 MHz, CDCl3) δ 7.98-7.79 (m, 1H), 7.81-7.68 (m, 1H), 7.59-7.47 (d, J = 8.7 Hz, 2H), 7.40-7.29 (m, 1H), 7.25-720 (m, 1H), 7.05-6.95 (m, 9H), 6.98-6.89 (d, J = 8.8 Hz, 1H), 6.72-6.63 (d, J = 8.2 Hz, 1H), 5.50-5.29 (m, 1H), 5.03-4.88 (m, 1H), 4.83-4.72 (d, J = 17.2 Hz, 1H), 4.41-4.32 (d, J = 6.1 Hz, 1H), 4.31-4.22 (d, J = 5.8 Hz, 1H), 4.05-3.99 (s, 3H), 3.69-3.63 (s, 1H), 3.65-3.55 (m, 8H), 3.50-3.32 (m, 2H) |

-continued

| No. | Chemical Formula | M.W. | NMR |
|---|---|---|---|
| D-13 | | 872.02 | — |
| D-14 | | 787.90 | — |
| D-15 | | 830.93 | — |
| D-16 | | 803.90 | — |
| D-17 | | 787.90 | — |

-continued

| No. | Chemical Formula | M.W. | NMR |
|---|---|---|---|
| D-18 | | 802.92 | — |
| D-19 | | 816.95 | — |
| D-20 | | 894.03 | — |
| D-21 | | 817.93 | — |
| D-22 | | 817.93 | 1H NMR (300 MHz, CDCl3) δ 7.99-7.84 (m, 1H), 7.82-7.66 (m, 1H), 7.62-7.53 (d, J = 8.7 Hz, 2H), 7.40-7.30 (m, 1H), 7.24-7.11 (m, 1H), 7.08-6.99 (m, 10H), 6.98-6.89 (d, J = 8.8 Hz, 1H), 6.74-6.65 (d, J = 8.2 Hz, 1H), 5.51-5.27 (m, 1H), 5.08-4.93 (m, 1H), 4.86-4.74 (d, J = 17.2 Hz, 1H), 4.45-4.36 (d, J = 6.1 Hz, 1H), 4.35-4.26 (d, J = 5.8 Hz, 1H), 4.06-4.00 (s, 3H), 3.86-3.80 (s, 3H), 3.68-3.62 (s, 1H), 3.53-3.36 (m, 2H), 3.35-3.16 (m, 1H) |

-continued

| No. | Chemical Formula | M.W. | NMR |
|---|---|---|---|
| D-23 | | 860.01 | 1H NMR (300 MHz, CDCl3) δ 7.98-7.81 (m, 4H), 7.76-7.65 (m, 2H), 7.62-7.51 (dd, J = 6.7, 2.3 Hz, 2H), 7.40-729 (m, 3H), 725-7.11 (m, 5H), 7.07-6.98 (m, 2H), 6.98-6.85 (dd, J = 6.9, 2.0 Hz, 3H), 6.74-6.63 (m, 3H), 5.63-5.27 (m, 4H), 5.15-4.94 (m, 2H), 4.87-4.74 (m, 1H), 4.49-4.22 (m, 2H), 4.02-4.00 (s, 1H), 3.98-3.95 (m, 2H), 3.54-3.15 (m, 7H), 1.85-1.71 (m, 2H), 1.55-1.41 (m, 4H), 1.33-1.18 (s, 5H), 1.04-0.94 (t, J = 7.4 Hz, 3H). |
| D-24 | | 817.93 | — |
| D-25 | | 978.15 | — |
| D-26 | | 845.98 | — |
| D-27 | | 801.93 | — |

-continued

| No. | Chemical Formula | M.W. | NMR |
|---|---|---|---|
| D-28 | | 801.93 | — |
| D-29 | | 751.87 | — |
| D-30 | | 808.97 | — |
| D-31 | | 909.08 | (CDCl3, 300 MHz) δ 7.84~7.78 (m, 3H), 7.61 (d, 2H, J = 8.1 Hz), 7.38~7.09 (m, 6H), 7.02 (d, 2H, J = 8.7 Hz), 6.90 (d, 2H, J = 7.2 Hz), 6.70~6.65 (m, 2H), 6.10 (d, 1H, J = 8.4 Hz), 5.55~5.44 (m, 3H), 5.36 (t, 1H, J = 5.6 Hz), 5.01~4.70 (m, 3H), 4.49~4.24 (m, 3H), 3.99 (s, 3H), 3.50~3.17 (m, 8H), 2.17~2.06 (m, 4H), 1.45 (s, 9H), 1.37~1.24 (m, 4H) |
| D-32 | | 823.98 | — |

-continued

| No. | Chemical Formula | M.W. | NMR |
|---|---|---|---|
| D-33 | | 740.85 | — |
| D-34 | | 782.93 | — |
| D-35 | | 768.90 | — |
| D-36 | | 754.88 | — |
| D-37 | | 808.85 | — |

| No. | Chemical Formula | M.W. | NMR |
|---|---|---|---|
| D-38 | 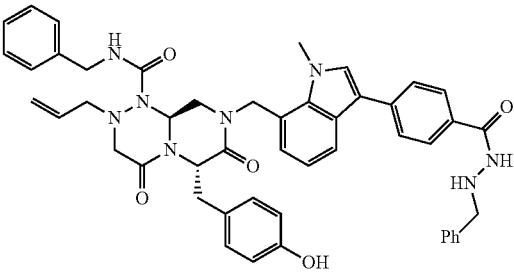 [SMILES: C=CCN1CC(=O)N2[C@@H](Cc3ccc(O)cc3)C(=O)N(Cc3cccc4c(-c5ccc(C(=O)NNCc6ccccc6)cc5)cn(C)c34)C[C@@H]2N1C(=O)NCc1ccccc1] | 816.95 | — |
| D-39 | 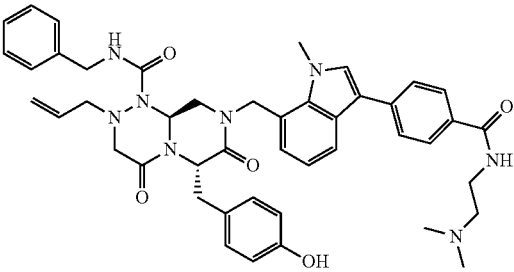 [SMILES: C=CCN1CC(=O)N2[C@@H](Cc3ccc(O)cc3)C(=O)N(Cc3cccc4c(-c5ccc(C(=O)NCCN(C)C)cc5)cn(C)c34)C[C@@H]2N1C(=O)NCc1ccccc1] | 782.93 | — |
| D-40 | 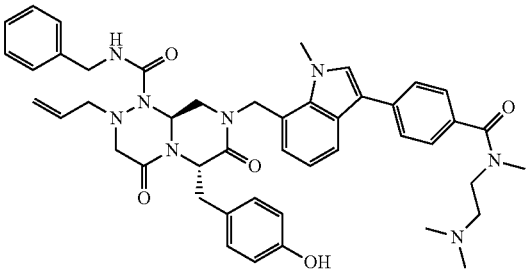 [SMILES: C=CCN1CC(=O)N2[C@@H](Cc3ccc(O)cc3)C(=O)N(Cc3cccc4c(-c5ccc(C(=O)N(C)CCN(C)C)cc5)cn(C)c34)C[C@@H]2N1C(=O)NCc1ccccc1] | 796.96 | — |
| D-41 | 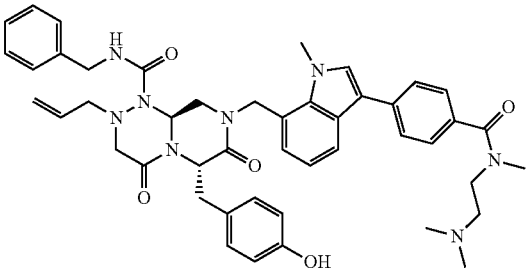 [SMILES: C=CCN1CC(=O)N2[C@@H](Cc3ccc(O)cc3)C(=O)N(Cc3cccc4c(-c5ccc(C(=O)N(C)CCN(C)C)cc5)cn(C)c34)C[C@@H]2N1C(=O)NCc1ccccc1] | 796.89 | — |
| D-42 | 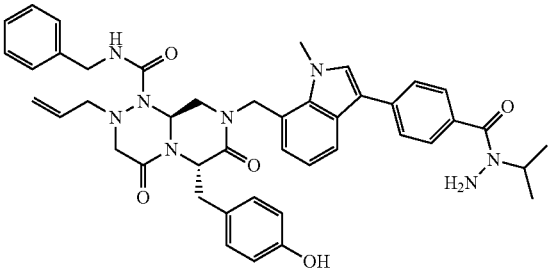 [SMILES: C=CCN1CC(=O)N2[C@@H](Cc3ccc(O)cc3)C(=O)N(Cc3cccc4c(-c5ccc(C(=O)N(N)C(C)C)cc5)cn(C)c34)C[C@@H]2N1C(=O)NCc1ccccc1] | 768.90 | — |

-continued

| No. | Chemical Formula | M.W. | NMR |
|---|---|---|---|
| D-43 | | 796.91 | — |
| D-44 | | 873.01 | — |
| D-45 | | 809.95 | — |
| D-46 | | 783.91 | — |
| D-47 | | 755.86 | — |

| No. | Chemical Formula | M.W. | NMR |
|---|---|---|---|
| D-48 | 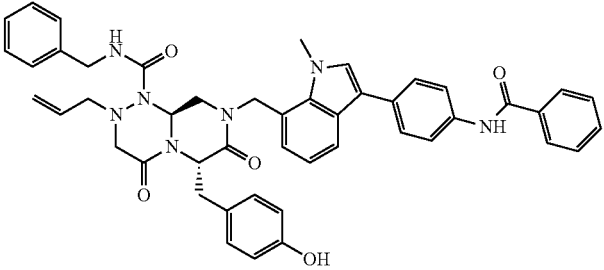 [SMILES: C=CCN1CC(=O)N2[C@@H](Cc3ccc(O)cc3)C(=O)N(Cc3cccc4c(-c5ccc(NC(=O)c6ccccc6)cc5)cn(C)c34)C[C@@H]2N1C(=O)NCc1ccccc1] | 787.90 | 1H NMR (300 MHz, CDCl3) δ 8.08-7.98 (s, 1H), 7.97-7.80 (m, 3H), 7.76-7.65 (m, 2H), 7.64-7.42 (m, 5H), 7.39-729 (m, 2H), 7.25-7.20 (m, 1H), 7.16-7.06 (m, 2H), 7.06-6.98 (d, J = 8.5 Hz, 2H), 6.95-6.86 (d, J = 7.2 Hz, 1H), 6.77-6.63 (m, 3H), 5.60-5.42 (m, 3H), 5.40-5.31 (t, J = 5.5 Hz, 1H), 5.05-4.86 (m, 2H), 4.81-4.68 (dd, J = 17.6, 1.4 Hz, 1H), 4.49-4.22 (m, 2H), 4.01-3.92 (s, 3H), 3.51-3.18 (m, 8H). |
| D-49 | 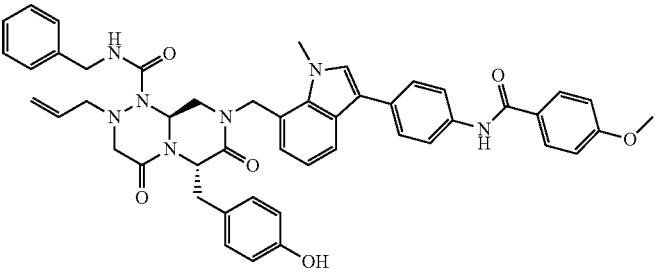 [SMILES: C=CCN1CC(=O)N2[C@@H](Cc3ccc(O)cc3)C(=O)N(Cc3cccc4c(-c5ccc(NC(=O)c6ccc(OC)cc6)cc5)cn(C)c34)C[C@@H]2N1C(=O)NCc1ccccc1] | 817.93 | 1H NMR (300 MHz, CDCl3) δ 7.98-7.77 (m, 4H), 7.74-7.64 (m, 2H), 7.64-7.49 (m, 2H), 7.40-7.29 (m, 0H), 7.25-7.18 (d, J = 8.4 Hz, 3H, 7.16-7.06 (m, 2H), 7.05-6.95 (dd, J = 12.9, 8.6 Hz, 1H), 6.94-6.87 (d, J = 7.2 Hz, 0H), 6.73-6.62 (m, 3H), 5.61-5.43 (m, 1H), 5.40-5.33 (t, J = 5.5 Hz, 0H), 5.06-4.95 (dd, J = 10.2, 1.3 Hz, 0H), 4.95-4.85 (d, J = 15.0 Hz, 0H), 4.81-4.68 (dd, J = 17.3, 1.3 Hz, 1H), 4.49-4.22 (ddd, J = 39.4, 14.9, 6.0 Hz, 2H), 4.02-3.92 (s, 3H), 3.90-3.84 (s, 1H), 3.51-3.17 (m, H). |
| D-50 | 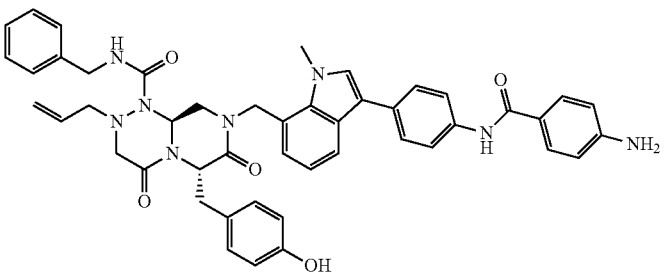 [SMILES: C=CCN1CC(=O)N2[C@@H](Cc3ccc(O)cc3)C(=O)N(Cc3cccc4c(-c5ccc(NC(=O)c6ccc(N)cc6)cc5)cn(C)c34)C[C@@H]2N1C(=O)NCc1ccccc1] | 802.92 | (CDCl3, 300 MHz) δ 7.85 (d, 1H, J = 7.5 Hz), 7.75~7.66 (m, 4H), 7.61~6.55 (m, 2H), 7.39~7.22 (m, 5H), 7.13~7.08 (m, 2H), 7.03 (d, 2H, J = 8.7 Hz), 6.90 (d, 1H, J = 7.5 Hz), 6.74~6.67 (m, 4H), 5.65 (s, 1H), 5.55~5.30 (m, 4H), 5.01~4.71 (m, 3H), 4.42 (dd, 1H, J = 15, 6.0 Hz), 4.28 (dd, 1H, J = 15, 6.0 Hz), 3.99 (s, 3H), 3.46~3.16 (m, 8H) |

| No. | Chemical Formula | M.W. | NMR |
|---|---|---|---|
| D-51 | | 830.97 | 1H NMR (300 MHz, CDCl3) δ 7.91-7.77 (m, 4H), 7.75-7.64 (m, 2H), 7.64-7.51 (m, 2H), 7.42-7.29 (m, 3H), 7.25-7.20 (d, J = 84 Hz, 2H), 7.17-6.97 (m, 4H), 6.97-6.88 (d, J = 7.1 Hz, 1H), 6.78-6.62 (m, 5H), 5.62-5.41 (m, 3H), 5.41-5.32 (t, J = 5.6 Hz, 1H), 5.04-4.94 (m, 1H), 4.94-4.82 (d, J = 15.0 Hz, 1H), 4.79-4.67 (m, 1H), 4.50-4.36 (m, 1H), 4.36-4.22 (m, 1H), 4.02-3.95 (s, 3H), 3.50-3.17 (m, 7H), 3.09-3.02 (s, 6H). |
| D-52 | | 809.99 | — |
| D-53 | | 816.95 | — |
| D-54 | | 845.00 | — |
| D-55 | | 873.05 | — |

| No. | Chemical Formula | M.W. | NMR |
|---|---|---|---|
| D-56 | | 816.95 | (CD3OD, 300 MHz) δ 7.78~7.73 (m, 3H), 7.65 (d, 2H, J = 8.4 Hz), 7.53 (d, 2H, J = 8.7 Hz), 7.28~7.16 (m, 6H), 7.04 (t, 1H, J = 7.2 Hz), 6.91~6.84 (m, 3H), 6.63~6.57 (m, 4H), 5.68~5.59 (m, 1H), 5.49~5.44 (m, 1H), 5.28~4.75 (m, 5H), 4.28~4.17 (m, 2H), 3.98 (s, 3H), 3.58~3.01 (m, 8H), 2.78 (s, 3H) |
| D-57 | | 859.03 | (CDCl3, 300 MHz) δ 7.86~7.77 (m, 4H), 7.69 (d, 2H, J = 8.4 Hz), 7.55 (d, 2H, J = 8.4 Hz), 7.35~7.21 (m, 5H), 7.10~7.07 (m, 2H), 7.029 (d, 2H, J = 8.1 Hz), 6.91 (d, 1H, J = 7.2 Hz), 6.69~6.66 (m, 4H), 5.58~5.34 (m, 4H), 4.98 (d, 1H, J = 10.5 Hz), 4.88 (d, 1H J = 15.3 Hz), 4.72 (d, 1H, J = 17.4 Hz), 4.42 (dd, 1H, J = 15, 6.3 Hz), 4.29 (dd, 1H, J = 15, 6.3 Hz), 3.97 (s, 3H), 3.40~3.20 (m, 12H), 1.20 (t, 6H, J = 6.9 Hz) |
| D-58 | | 886.05 | — |
| D-59 | | 796.91 | — |

-continued
| No. | Chemical Formula | M.W. | NMR |
|---|---|---|---|
| D-60 | 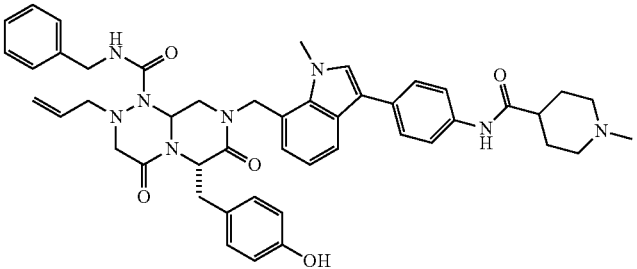 [SMILES: C=CCN1CC(=O)N2C(CN(Cc3cccc4c(-c5ccc(NC(=O)C6CCN(C)CC6)cc5)cn(C)c34)C(=O)[C@@H]2Cc2ccc(O)cc2)N1C(=O)NCc1ccccc1] | 808.97 | — |
| D-61 | 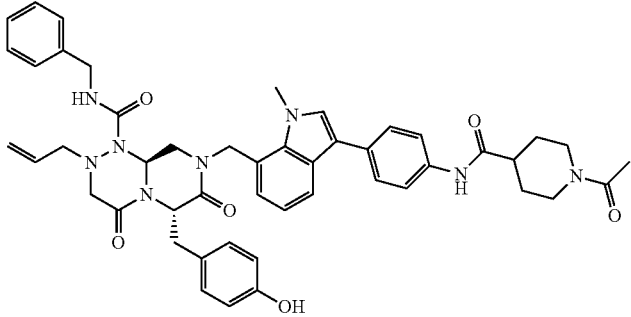 [SMILES: C=CCN1CC(=O)N2[C@@H](Cc3ccc(O)cc3)C(=O)N(Cc3cccc4c(-c5ccc(NC(=O)C6CCN(C(C)=O)CC6)cc5)cn(C)c34)C[C@@H]2N1C(=O)NCc1ccccc1] | 836.98 | — |
| D-62 | 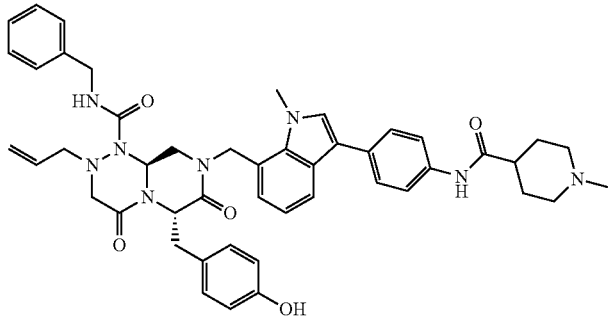 | 808.97 | — |
| D-63 | 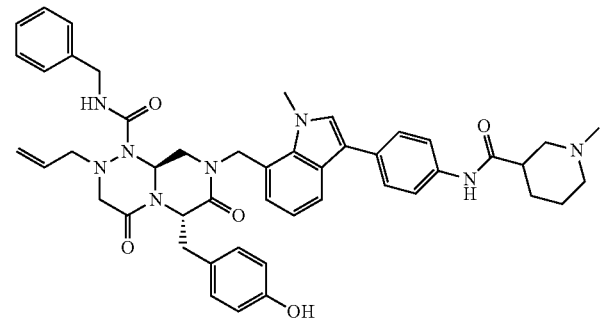 [SMILES: C=CCN1CC(=O)N2[C@@H](Cc3ccc(O)cc3)C(=O)N(Cc3cccc4c(-c5ccc(NC(=O)C6CCCN(C)C6)cc5)cn(C)c34)C[C@@H]2N1C(=O)NCc1ccccc1] | 808.97 | — |
| D-64 | 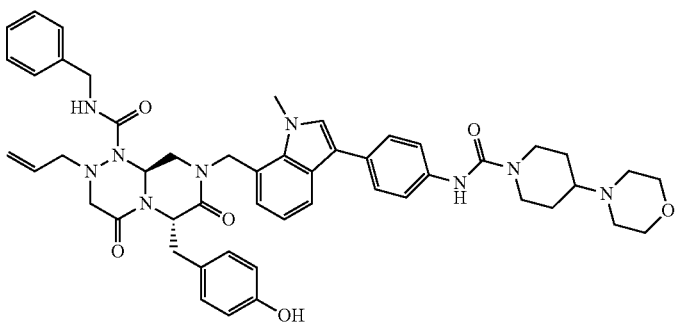 [SMILES: C=CCN1CC(=O)N2[C@@H](Cc3ccc(O)cc3)C(=O)N(Cc3cccc4c(-c5ccc(NC(=O)N6CCC(N7CCOCC7)CC6)cc5)cn(C)c34)C[C@@H]2N1C(=O)NCc1ccccc1] | 880.04 | — |

| No. | Chemical Formula | M.W. | NMR |
|---|---|---|---|
| D-65 | | 838.01 | — |
| D-66 | | 851.99 | — |
| D-66-1 | | 880.04 | — |
| D-67 | | 809.95 | — |
| D-68 | | 854.95 | — |

| No. | Chemical Formula | M.W. | NMR |
|---|---|---|---|
| D-69 | | 803.91 | (300 MHz, CDCl3): 3.112-3.539 (m, 6H), 4.256-4.449 (dq, J = 14.7 Hz, J = 5.7 Hz, 2H), 4.707-4.839 (dd, J = 21.6 Hz, J = 15.0 Hz, 1H), 4.987-5.650 (m, 7H), 6.678-7.598 (m, 20H) |
| D-70 | | 768.90 | — |
| D-71 | | 825.95 | — |
| D-72 | | 838.99 | — |
| D-73 | | 802.92 | 1H NMR (CDCl3, 300 MHz) δ 7.82 (d, J = 7.4 Hz, 1H), 7.51-7.36 (m, 7H), 7.36-7.22 (m, 8H), 7.20-7.12 (m, 2H), 7.10-6.99 (m, 3H), 6.99-6.92 (d, J = 8.5 Hz, 2H), 6.84-6.77 (d, J = 7.2 Hz, 1H), 6.76-6.66 (m, 3H), 5.57 (m, 1H), 5.41 (m, 1H), 5.32-5.21 (m, 2H), 5.10-4.93 (m, 2H), 4.84 (m, 1H), 4.38-4.19 (m, 2H), 4.00-3.89 (s, 3H), 3.49-3.20 (m, 8H), 3.20 (m, 1H). |

-continued

| No. | Chemical Formula | M.W. | NMR |
|---|---|---|---|
| D-74 | | 808.97 | 1H NMR (300 MHz,) δ 7.80 (d, J = 7.9 Hz, 1H), 7.48-7.39 (m, 2H), 7.38-7.19 (m, 8H), 7.20-7.12 (m, 2H), 7.08-7.00 (m, 2H), 6.99-6.89 (d, J = 8.5 Hz, 2H), 6.84 (d, J = 7.1 Hz, 1H), 6.76-6.64 (m, 3H), 5.57-5.33 (m, 2H), 5.33-5.20 (m, 2H), 5.09-4.92 (m, 2H), 4.82 (d, J = 17.1 Hz, 1H), 4.38-4.18 (m, 2H), 3.99-3.88 (s, 3H), 3.66 (m, 1H), 3.48-3.19 (m, 9H), 3.18 (d, J = 4.1 Hz, 1H), 1.99-1.83 (m, 2H), 1.75-1.50 (m, 3H), 1.43-1.24 (m, 2H), 1.23-1.01 (m, 3H). |
| D-75 | | 830.97 | — |
| D-76 | | 832.94 | — |

| No. | Chemical Formula | M.W. | NMR |
|---|---|---|---|
| D-77 | | 833.93 | (CDCl3, 300 MHz) δ 11.66 (bs, 1H), 8.43 (s, 1H), 8.28 (s, 1H), 7.77 (m, 2H), 7.64 (d, 2H, J = 7.8 HZ), 7.38 (m, 2H), 7.24 ~7.19 (m, 4H), 7.14 (m, 1H), 7.07 (s, 1H), 7.04 (d, 2H, J = 8.4 Hz), 6.90 (d, 2H, J = 7.2 Hz), 6.75 (d, 2H, J = 8.4 Hz), 6.70 (t, 1H J = 5.7 Hz), 5.57 (m, 1H), 5.42-5.34 (m, 3H), 5.29 (d, 1H, J = 15.0 Hz), 5.18 (d, 1H, J = 15.0 Hz), 5.08 (d, 1H, J = 10.2 Hz), 4.90 (d, 1H, J = 17.1 Hz), 4.44 (dd,1H, J = 15.0, 8.3 Hz), 4.32 (dd, 1H, J = 15.0, 6.0 Hz), 3.98 (s, 3H), 3.54~3.22 (m, 8H) |
| D-78 | | 902.05 | — |
| D-79 | | 794.94 | — |
| D-80 | | 816.95 | — |

| No. | Chemical Formula | M.W. | NMR |
|---|---|---|---|
| D-81 | | 804.89 | — |
| D-82 | | 804.89 | — |
| D-83 | | 804.89 | — |
| D-84 | | 851.99 | — |

-continued

| No. | Chemical Formula | M.W. | NMR |
|---|---|---|---|
| D-85 | | 803.91 | (CDCl3, 300 MHz) δ 8.01~7.87 (m, 3H), 7.75 (d, 1H, J = 8.1 Hz), 7.39~7.18 (m, 4H), 7.12 (s, 1H), 7.08~6.99 (m, 3H), 7.04 (d, 2H, J = 8.1 Hz), 6.95 (d, 2H, J = 10.5 Hz), 6.83~6.71 (m, 3H) 6.76 (s, 1H), 6.73 (d, 2H, J = 8.1 Hz), 5.61~5.47 (m, 3H), 5.44 (t, 1H, J = 4.8 Hz), 5.39~5.25 (m, 3H), 5.03~4.97 (m, 3H), 4.83 (d, 1H, J = 17.1 Hz), 4.43 (dd, 1H, J = 14.7, 6.3 Hz), 4.32 (dd, 1H, J = 15.6, 5.7 Hz), 3.91 (s, 3H), 3.56~3.18 (m, 8H) |
| D-86 | | 833.93 | — |
| D-87 | | 810.94 | — |
| D-88 | | 797.90 | 1H NMR (300 MHz,) δ 8.46 (d, J = 1.7 Hz, 1H), 8.15 (d, J = 8.7 Hz, 1H), 7.93 (dd, J = 8.6, 2.3 Hz, 1H), 7.79 (m, 1H), 7.41-7.18 (m, 4H), 7.16-7.08 (m, 2H), 7.07-6.98 (d, J = 8.4 Hz, 2H), 6.95 (m, 1H), 6.75-6.62 (m, 3H), 5.60-5.39 (m, 3H), 5.39 (t, J = 5.5 Hz, 1H), 5.08-4.90 (m, 2H), 4.85-4.72 (m, 1H), 4.49 (dd, 1H, J = 15.0, 6, 1 Hz), 4.34 (dd, 1H, J = 15.6, 5.7 Hz), 4.07 (s, 3H), 3.82-3.71 (m, 4H), 3.60-3.51 (m, 4H), 3.49-3.18 (m, 8H). |

| No. | Chemical Formula | M.W. | NMR |
|---|---|---|---|
| D-89 | 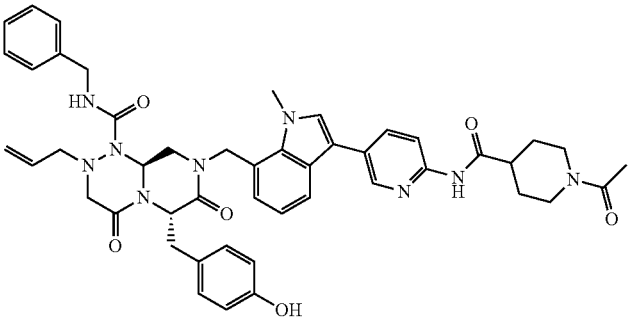 [SMILES: C=CCN1CC(=O)N2[C@@H](Cc3ccc(O)cc3)C(=O)N(Cc3cccc4c(-c5ccc(NC(=O)C6CCN(C(C)=O)CC6)nc5)cn(C)c34)C[C@@H]2N1C(=O)NCc1ccccc1] | 838.95 | — |
| D-90 | 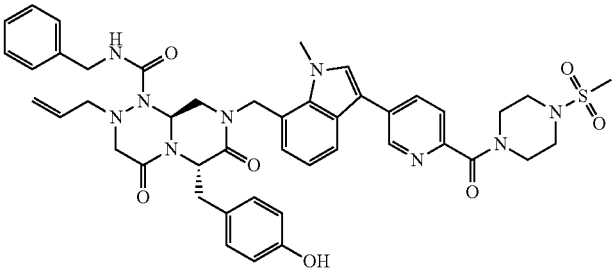 [SMILES: C=CCN1CC(=O)N2[C@@H](Cc3ccc(O)cc3)C(=O)N(Cc3cccc4c(-c5ccc(C(=O)N6CCN(S(C)(=O)=O)CC6)nc5)cn(C)c34)C[C@@H]2N1C(=O)NCc1ccccc1] | 859.99 | 1H NMR (300 MHz, CDCl3) δ 8.85-8.78 (s, 2H), 8.08-7.98 (d, J = 8.0 Hz, 2H), 7.87-7.77 (m, 4H), 7.41-7.29 (m, 3H), 7.26-7.15 (m, 4H), 7.07-7.00 (d, J = 7.9 Hz, 2H), 6.97-6.90 (d, J = 7.2 Hz, 1H), 6.75-6.65 (m, 2H), 5.61-5.52 (d, J = 6.6 Hz, 1H), 5.49-5.42 (s, 1H), 5.40-5.28 (d, J = 15.4 Hz, 4H), 5.12-5.00 (m, 3H), 4.90-4.77 (d, J = 17.3 Hz, 2H), 4.48-4.25 (dd, J = 27.5, 6.2 Hz, 1H), 4.12-4.02 (s, 3H), 3.98-3.92 (m, 8H), 3.69-3.62 (s, 2H), 3.53-3.47 (m, 4H), 3.45-3.33 (m, 4H), 2.24-2.13 (s, 3H). |
| D-91 | 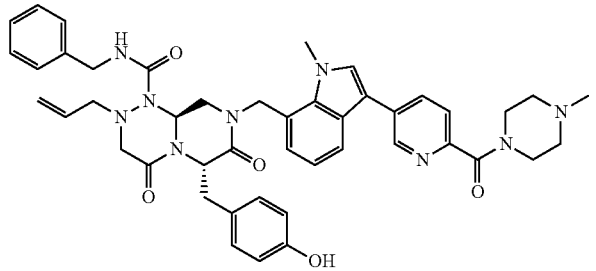 [SMILES: C=CCN1CC(=O)N2[C@@H](Cc3ccc(O)cc3)C(=O)N(Cc3cccc4c(-c5ccc(C(=O)N6CCN(C)CC6)nc5)cn(C)c34)C[C@@H]2N1C(=O)NCc1ccccc1] | 795.93 | 1H NMR (300 MHz, CDCl3) δ 8.39-8.26 (s,2H), δ 8.22-8.12 (s, 1H), 7.76-7.65 (d, J = 8.3 Hz, 1H),7.45-7.19 (m, 4H), 7.16-7.05 (t, J = 7.6 Hz, 1H), 7.07-6.98 (m, 3H), 6.96-6.87 (d, J = 7.4 Hz, 1H), 6.74-6.61 (dd, J = 8.2, 2.1 Hz, 3H), 5.61-5.44 (m, 3H), 5.40-5.32 (t, J = 5.6 Hz, 1H), 5.06-4.96 (m, 1H), 4.96-4.86 (d, J = 15.0 Hz, 1H), 4.82-4.69 (d, J = 17.1 Hz, 1H), 4.50-4.23 (ddd, J = 44.6, 15.0, 5.9 Hz, 2H), 4.05-3.94 (s, 3H), 3.43-3.37 (d, J = 5.3 Hz, 4H), 3.25-3.10 (m, 4H), 2.29-2.10 (m, 7H) |

-continued
| No. | Chemical Formula | M.W. | NMR |
|---|---|---|---|
| D-92 | 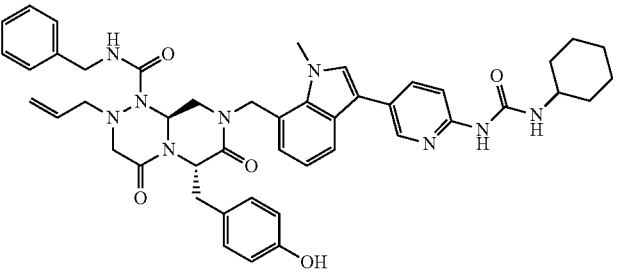 [SMILES: C=CCN1CC(=O)N2[C@@H](Cc3ccc(O)cc3)C(=O)N(Cc3cccc4c(-c5ccc(NC(=O)NC6CCCCC6)nc5)cn(C)c34)C[C@@H]2N1C(=O)NCc1ccccc1] | 809.95 | — |
| D-93 | 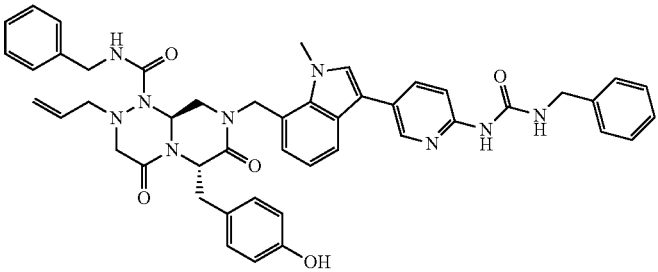 [SMILES: C=CCN1CC(=O)N2[C@@H](Cc3ccc(O)cc3)C(=O)N(Cc3cccc4c(-c5ccc(NC(=O)NCc6ccccc6)nc5)cn(C)c34)C[C@@H]2N1C(=O)NCc1ccccc1] | 817.93 | — |
| D-94 | 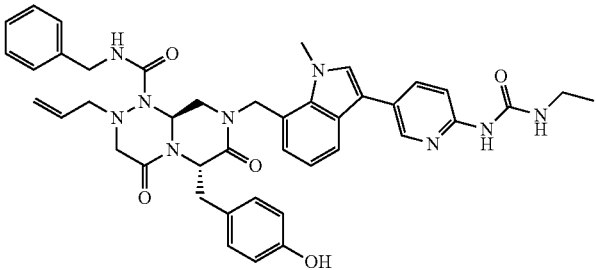 [SMILES: C=CCN1CC(=O)N2[C@@H](Cc3ccc(O)cc3)C(=O)N(Cc3cccc4c(-c5ccc(NC(=O)NCC)nc5)cn(C)c34)C[C@@H]2N1C(=O)NCc1ccccc1] | 755.86 | — |
| D-95 | 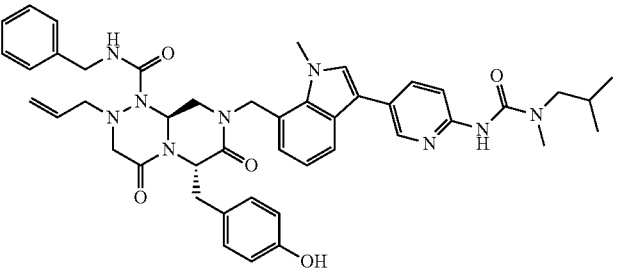 [SMILES: C=CCN1CC(=O)N2[C@@H](Cc3ccc(O)cc3)C(=O)N(Cc3cccc4c(-c5ccc(NC(=O)N(C)CC(C)C)nc5)cn(C)c34)C[C@@H]2N1C(=O)NCc1ccccc1] | 797.94 | — |
| D-96 | 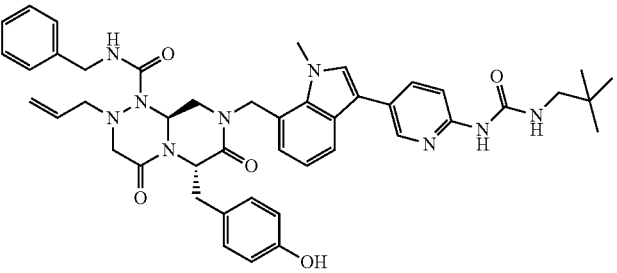 [SMILES: C=CCN1CC(=O)N2[C@@H](Cc3ccc(O)cc3)C(=O)N(Cc3cccc4c(-c5ccc(NC(=O)NCC(C)(C)C)nc5)cn(C)c34)C[C@@H]2N1C(=O)NCc1ccccc1] | 797.94 | — |

-continued

| No. | Chemical Formula | M.W. | NMR |
|---|---|---|---|
| D-97 | | 875.01 | — |
| D-98 | | 824.97 | — |
| D-99 | | 769.89 | — |
| D-100 | | 810.94 | — |
| D-101 | | 715.8 | 1H NMR (300 MHz, CDCl3) δ 8.00-7.90 (m, 1H), 7.72-7.64 (d, J = 4.0 Hz, 1H), 7.40-7.27 (m, 3H), 7.25-7.14 (m, 3H), 7.06-6.90 (m, 3H), 6.75-6.63 (m, 3H), 5.62-5.40 (m, 3H), 5.40-5.28 (t, J = 5.5 Hz, 1H), 5.07-4.87 (m, 2H), 4.85-4.72 (d, J = 17.0 Hz, 1H), 4.50-4.23 (ddd, J = 40.3, 14.9, 5.9 Hz, 2H), 4.06-3.96 (m, 3H), 3.54-3.17 (m, 8H), 2.60-2.53 (s, 3H). |

-continued

| No. | Chemical Formula | M.W. | NMR |
|---|---|---|---|
| D-102 | | 729.82 | 1H NMR (300 MHz, CDCl3) δ 7.94-7.90 (m, 1H), 7.71-7.62 (d, J = 4.0 Hz, 1H), 7.38-7.25 (m, 3H), 7.23-7.12 (m, 3H), 7.02-6.86 (m, 3H), 6.73-6.61 (m, 3H), 5.61-5.39 (m, 3H), 5.43-5.31 (t, J = 5.5 Hz, 1H), 5.03-4.83 (m, 2H), 4.87-4.74 (d, J = 17.0 Hz, 1H), 4.51-4.24 (ddd, J = 40.3, 14.9, 5.9 Hz, 2H), 4.04-3.94 (m, 3H), 3.51-3.19 (m, 8H), 2.58-2.51 (s, 6H). |
| D-103 | | 798.93 | — |
| D-104 | | 826.98 | — |
| D-105 | | 784.9 | — |

TABLE 3

| No. | Chemical Formula | M.W. | NMR |
|---|---|---|---|
| E-1 | | 804.93 | — |
| E-2 | | 704.82 | — |
| E-3 | | 705.80 | (300 MHz, CDCl3): 2.705-3.192 (m, 2H), 3.345-3.484 (m, 4H), 3.684-3.771 (m, 9H), 4.413-5.271 (m, 6H), 5.652-5.845 (m, 6H), 6.036-6.112 (m, 2H), 6.584-8.178 (m, 20H) |
| E-4 | | 718.84 | 1N NMR(300 MHz, CDCL3, ppm, δ): 7.67(d, J = 8.011, 1H), 7.37~7.12(m, 6H), 7.14(dd, J = 7.248, J = 8.011, 1H), 6.97(d, J = 8.392, 2H), 6.92(d, J = 6.866, 1H), 6.68~6.62(m, 3H), 5.61~5.43(m, 2H), 5.34~5.26(m, 2H), 5.09~4.84(m, 3H), 4.47~4.26(m, 2H), 3.97(s, 3H), 3.72(m, 4H), 3.49~3.22(m, 8H), 2.44(m, 4H), 2.33(s, 3H) |

TABLE 3-continued

| No. | Chemical Formula | M.W. | NMR |
|---|---|---|---|
| E-5 | | 732.87 | 1H NMR(300 MHz, CDCL3, ppm, δ): 7.66(d, J = 7.248, 1H), 7.37~7.22(m, 6H), 7.14(t, J = 7.629, 1H), 6.97(d, J = 8.392, 2H), 6.92(d, J = 8.011, 1H), 6.69-6.63(m, 3H), 5.61~5.52(m, 1H), 5.45~5.39(m, 1H), 5.33~5.28(m, 2H), 5.09~4.85(m, 3H), 4.46~4.26(m, 2H), 3.97(s, 3H), 3.73(m, 4H), 3.49-3.19(m, 8H), 2.49~2.42(m, 6H), 1.10(t, J = 7.248, 3H) |
| E-6 | | 746.9 | — |
| E-7 | | 746.9 | — |
| E-8 | | 760.92 | — |

TABLE 3-continued
| No. | Chemical Formula | M.W. | NMR |
|---|---|---|---|
| E-9 | 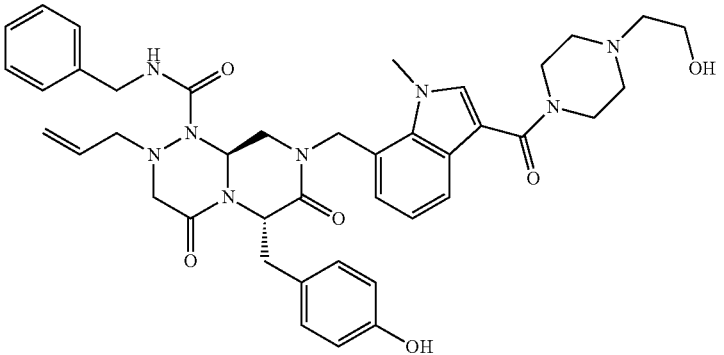 | 748.87 | |
| E-10 | 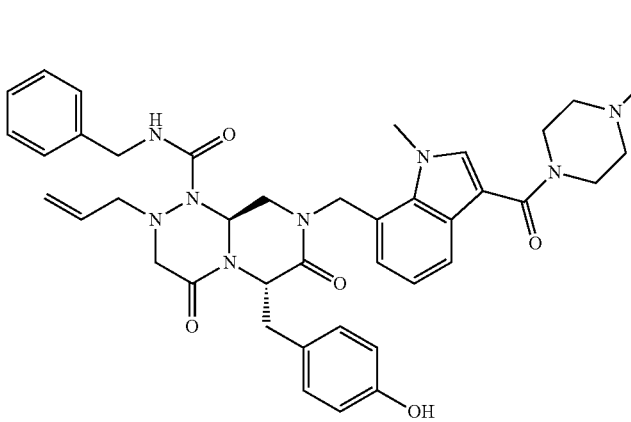 [SMILES: C=CCN1CC(=O)N2[C@@H](Cc3ccc(O)cc3)C(=O)N(Cc3cccc4c(C(=O)N5CCNCC5)cn(C)c34)C[C@@H]2N1C(=O)NCc1ccccc1] | 762.9 | 1H NMR(300 MHz, CDCl-d3, ppm, δ): 7.67(d, J = 7.2, 1H), 7.39~7.20(m, 6H), 7.13(dd, J = 7.5, 7.8, 1H), 6.98(d, J = 8.7, 2H), 6.92(d, J = 7.2, 1H), 6.71~6.63(m, 3H), 5.61~5.33(m, 4H), 5.07~4.82(m, 3H), 4.46-4.26(m, 2H), 3.96(s, 3H), 3.78~3.70(m, 4H), 3.54-3.20(m, 13H), 2.61(t, J = 5.4, 2H), 2.54~2.52(m, 4H). |
| E-11 | 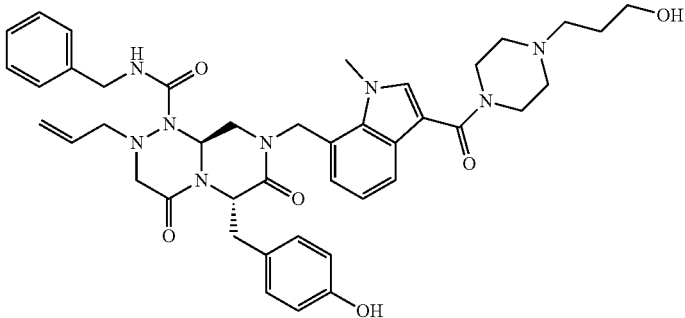 [SMILES: C=CCN1CC(=O)N2[C@@H](Cc3ccc(O)cc3)C(=O)N(Cc3cccc4c(C(=O)N5CCN(CCCO)CC5)cn(C)c34)C[C@@H]2N1C(=O)NCc1ccccc1] | 762.9 | — |
| E-12 | 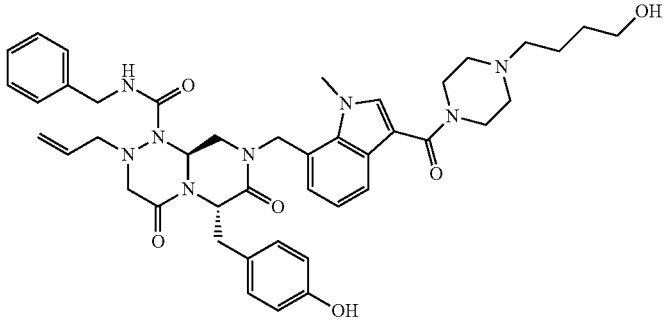 [SMILES: C=CCN1CC(=O)N2[C@@H](Cc3ccc(O)cc3)C(=O)N(Cc3cccc4c(C(=O)N5CCN(CCCCO)CC5)cn(C)c34)C[C@@H]2N1C(=O)NCc1ccccc1] | 776.92 | 1H NMR(300 MHz, CDCl-d3, ppm, δ): 7.64(d, J = 7.8, 1H), 7.40~7.22(m, 6H), 7.14(dd, J = 7.1, 8.1, 1H), 6.98(d, J = 8.4, 2H), 6.91(d, J = 7.2, 1H), 6.70~6.64(m, 3H), 5.63~5.49(m, 1H), 5.46~5.42(m, 1H), 5.34~5.28(m, 2H), 5.09~4.85(m, 3H), 4.46~4.26(m, 2H), 3.96 (s, 3H), 3.76~3.74(m, 4H), 3.60~3.59(m, 2H), 3.49-3.18(m, 8H), 2.55~2.53(m, 4H), 2.45~2.43(m, 2H), 1.61~1.58(m, 2H), 1.26~1.25(m, 2H). |

TABLE 3-continued
| No. | Chemical Formula | M.W. | NMR |
|---|---|---|---|
| E-13 | 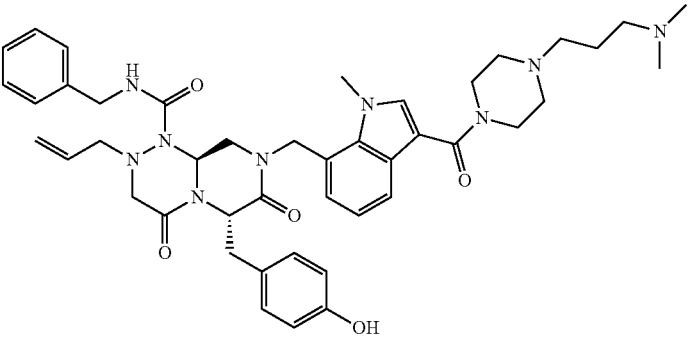 [SMILES: C=CCN1CC(=O)N2[C@@H](Cc3ccc(O)cc3)C(=O)N(Cc3cccc4c(C(=O)N5CCN(CCCN(C)C)CC5)cn(C)c34)C[C@@H]2N1C(=O)NCc1ccccc1] | 789.96 | — |
| E-14 | 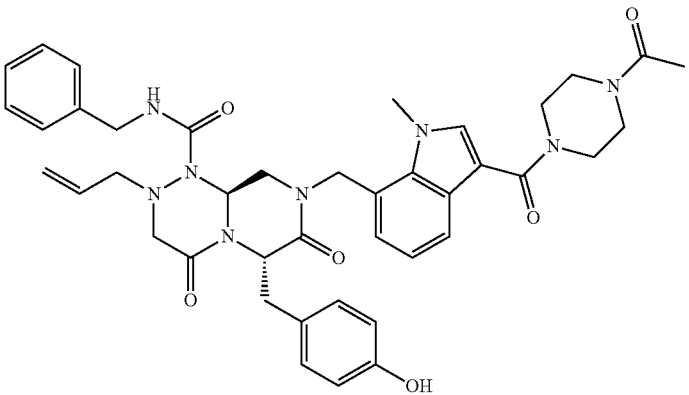 [SMILES: C=CCN1CC(=O)N2[C@@H](Cc3ccc(O)cc3)C(=O)N(Cc3cccc4c(C(=O)N5CCN(C(C)=O)CC5)cn(C)c34)C[C@@H]2N1C(=O)NCc1ccccc1] | 746.85 | — |
| E-15 | 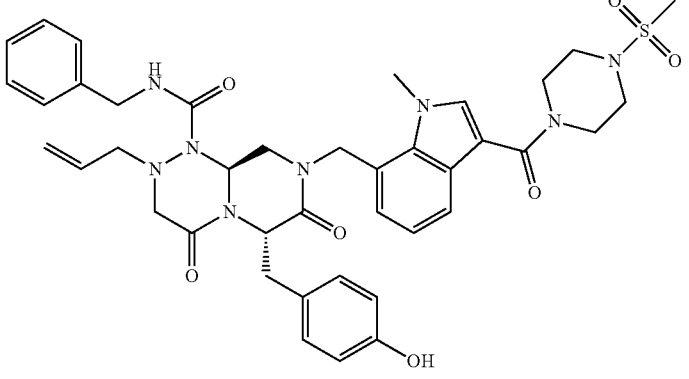 | 782.91 | — |
| E-16 | 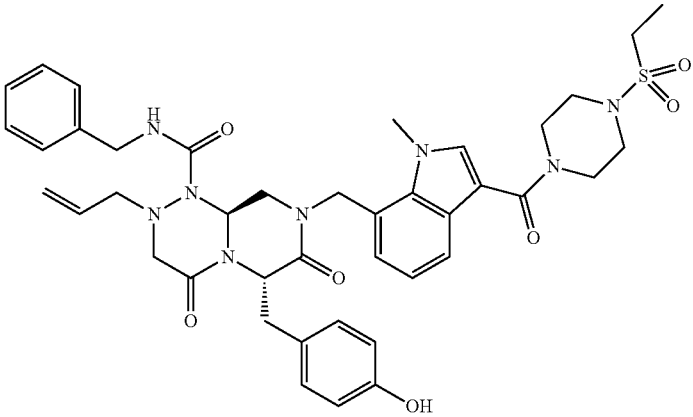 [SMILES: C=CCN1CC(=O)N2[C@@H](Cc3ccc(O)cc3)C(=O)N(Cc3cccc4c(C(=O)N5CCN(S(=O)(=O)CC)CC5)cn(C)c34)C[C@@H]2N1C(=O)NCc1ccccc1] | 796.94 | — |

TABLE 3-continued
| No. | Chemical Formula | M.W. | NMR |
|---|---|---|---|
| E-17 | 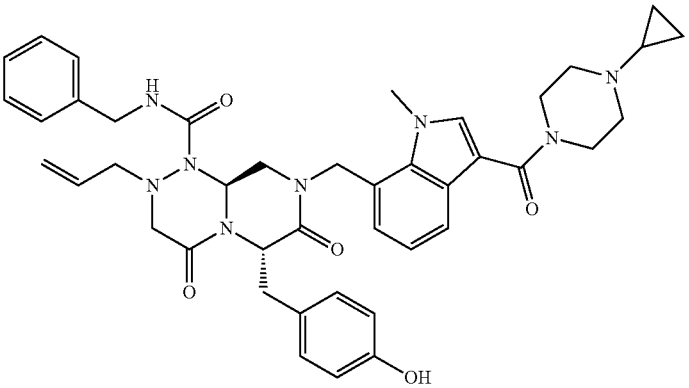 [SMILES: C=CCN1CC(=O)N2[C@@H](Cc3ccc(O)cc3)C(=O)N(Cc3cccc4c(C(=O)N5CCN(C6CC6)CC5)cn(C)c34)C[C@@H]2N1C(=O)NCc1ccccc1] | 744.88 | — |
| E-18 | 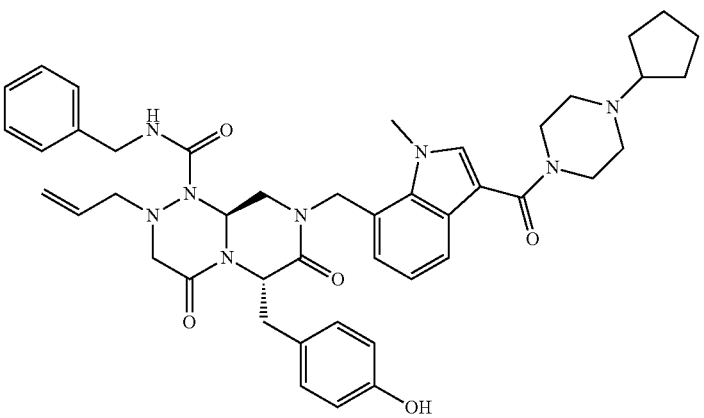 [SMILES: C=CCN1CC(=O)N2[C@@H](Cc3ccc(O)cc3)C(=O)N(Cc3cccc4c(C(=O)N5CCN(C6CCCC6)CC5)cn(C)c34)C[C@@H]2N1C(=O)NCc1ccccc1] | 772.93 | — |
| E-19 | 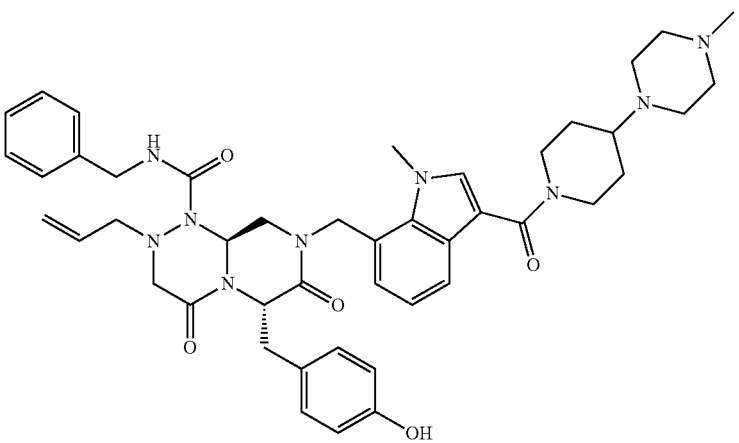 | 801.98 | — |
| E-20 | 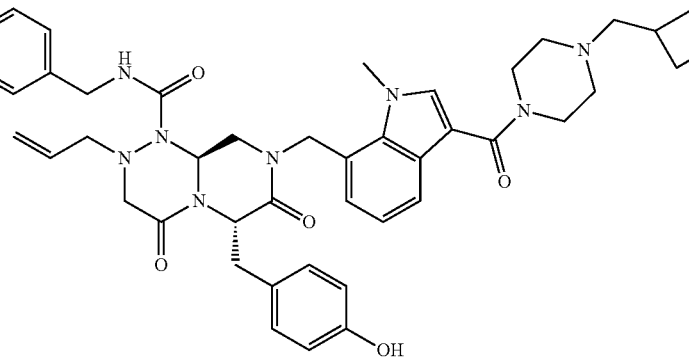 | 772.93 | — |

TABLE 3-continued
| No. | Chemical Formula | M.W. | NMR |
|---|---|---|---|
| E-21 | 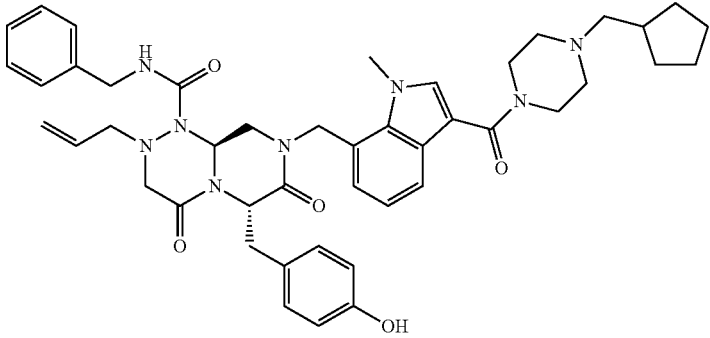 [SMILES: C=CCN1CC(=O)N2[C@@H](Cc3ccc(O)cc3)C(=O)N(Cc3cccc4c(C(=O)N5CCN(CC6CCCC6)CC5)cn(C)c34)C[C@@H]2N1C(=O)NCc1ccccc1] | 786.96 | — |
| E-22 | 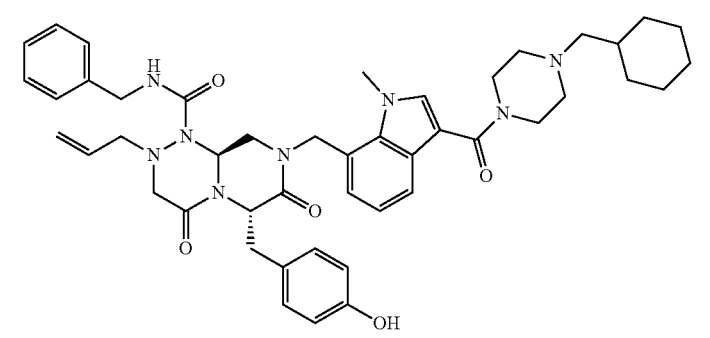 [SMILES: C=CCN1CC(=O)N2[C@@H](Cc3ccc(O)cc3)C(=O)N(Cc3cccc4c(C(=O)N5CCN(CC6CCCCC6)CC5)cn(C)c34)C[C@@H]2N1C(=O)NCc1ccccc1] | 800.98 | — |
| E-23 | 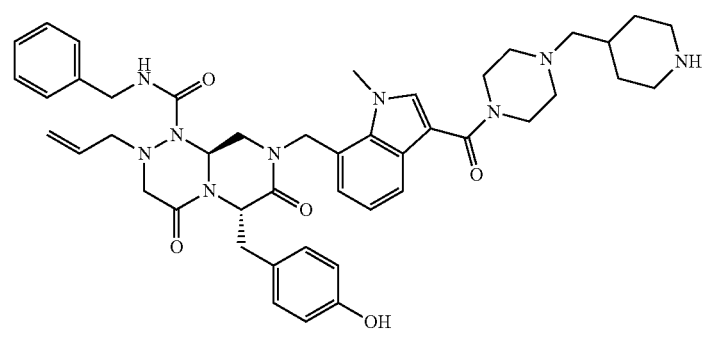 [SMILES: C=CCN1CC(=O)N2[C@@H](Cc3ccc(O)cc3)C(=O)N(Cc3cccc4c(C(=O)N5CCN(CC6CCNCC6)CC5)cn(C)c34)C[C@@H]2N1C(=O)NCc1ccccc1] | 801.98 | — |
| E-24 | 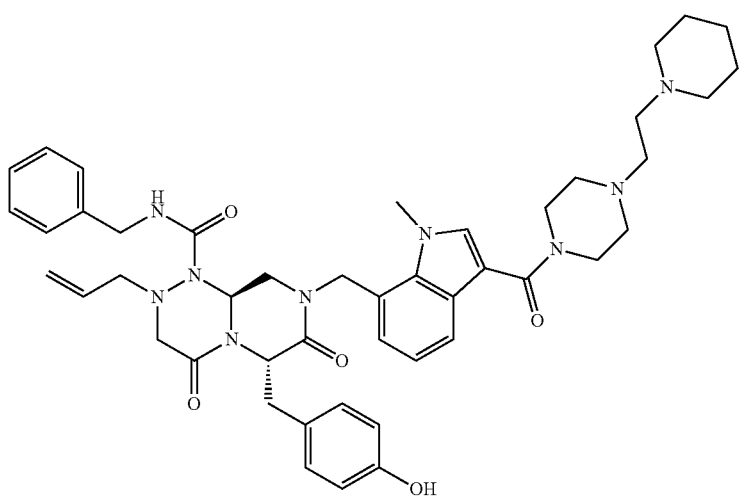 [SMILES: C=CCN1CC(=O)N2[C@@H](Cc3ccc(O)cc3)C(=O)N(Cc3cccc4c(C(=O)N5CCN(CCN6CCCCC6)CC5)cn(C)c34)C[C@@H]2N1C(=O)NCc1ccccc1] | 816.0 | — |

TABLE 3-continued

| No. | Chemical Formula | M.W. | NMR |
|---|---|---|---|
| E-25 | | 817.97 | 1H NMR(300 MHz, CDCl-d3, ppm, δ): 7.73~7.65(m, 1H), 7.40~7.22(m, 6H), 7.13(dd, J = 7.2, 8.1, 1H), 6.99~6.90(m, 3H), 6.70~6.63(m, 3H), 5.62~5.31(m, 4H), 5.08~4.84(m, 3H), 4.46~4.26(m, 2H), 3.96(s, 3H), 3.72~3.69(m, 8H), 3.48~3.20(m, 8H), 2.54~2.47(m, 12H). |
| E-26 | | 794.94 | — |
| E-27 | | 808.97 | — |

TABLE 3-continued
| No. | Chemical Formula | M.W. | NMR |
|---|---|---|---|
| E-28 | 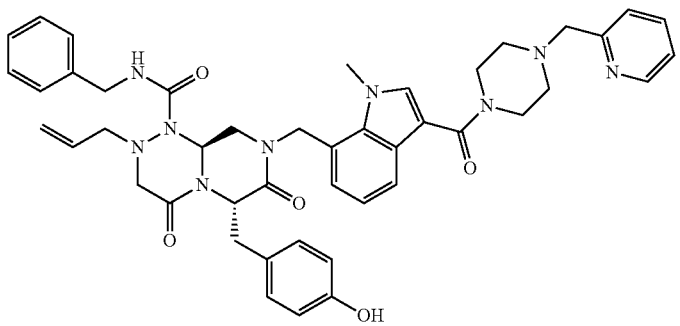 [SMILES: C=CCN1CC(=O)N2[C@@H](Cc3ccc(O)cc3)C(=O)N(Cc3cccc4c(C(=O)N5CCN(Cc6ccccn6)CC5)cn(C)c34)C[C@@H]2N1C(=O)NCc1ccccc1] | 795.93 | — |
| E-29 | 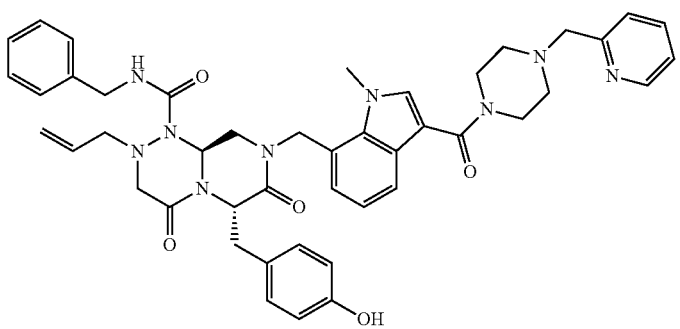 [SMILES: C=CCN1CC(=O)N2[C@@H](Cc3ccc(O)cc3)C(=O)N(Cc3cccc4c(C(=O)N5CCN(Cc6ccccn6)CC5)cn(C)c34)C[C@@H]2N1C(=O)NCc1ccccc1] | 795.93 | — |
| E-30 | 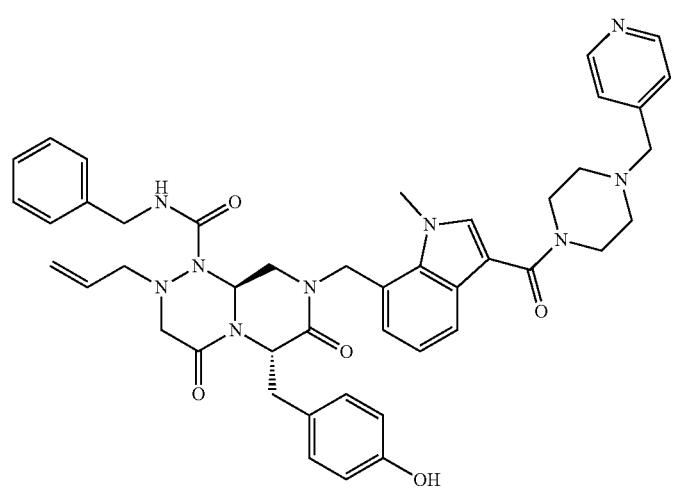 [SMILES: C=CCN1CC(=O)N2[C@@H](Cc3ccc(O)cc3)C(=O)N(Cc3cccc4c(C(=O)N5CCN(Cc6ccncc6)CC5)cn(C)c34)C[C@@H]2N1C(=O)NCc1ccccc1] | 795.93 | — |
| E-31 | 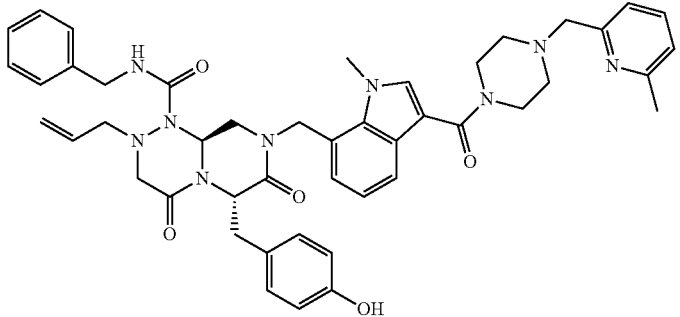 [SMILES: C=CCN1CC(=O)N2[C@@H](Cc3ccc(O)cc3)C(=O)N(Cc3cccc4c(C(=O)N5CCN(Cc6cccc(C)n6)CC5)cn(C)c34)C[C@@H]2N1C(=O)NCc1ccccc1] | 809.95 | — |

TABLE 3-continued
| No. | Chemical Formula | M.W. | NMR |
|---|---|---|---|
| E-32 | 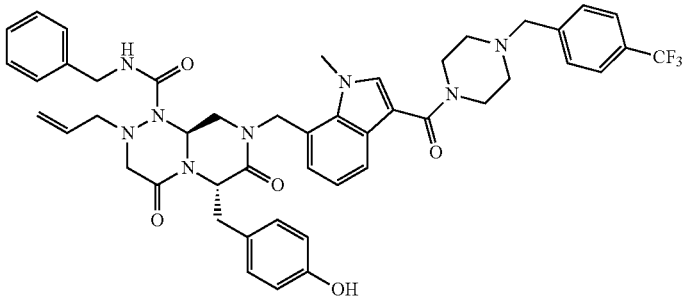 [SMILES: C=CCN1CC(=O)N2[C@@H](Cc3ccc(O)cc3)C(=O)N(Cc3cccc4c(C(=O)N5CCN(Cc6ccc(C(F)(F)F)cc6)CC5)cn(C)c34)C[C@@H]2N1C(=O)NCc1ccccc1] | 862.94 | — |
| E-33 | 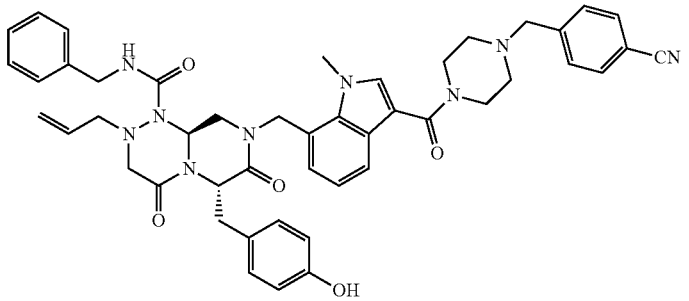 [SMILES: C=CCN1CC(=O)N2[C@@H](Cc3ccc(O)cc3)C(=O)N(Cc3cccc4c(C(=O)N5CCN(Cc6ccc(C#N)cc6)CC5)cn(C)c34)C[C@@H]2N1C(=O)NCc1ccccc1] | 819.95 | — |
| E-34 | 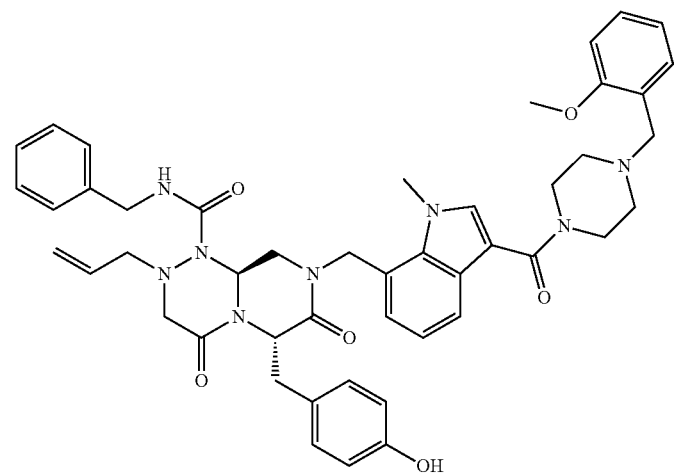 [SMILES: C=CCN1CC(=O)N2[C@@H](Cc3ccc(O)cc3)C(=O)N(Cc3cccc4c(C(=O)N5CCN(Cc6ccccc6OC)CC5)cn(C)c34)C[C@@H]2N1C(=O)NCc1ccccc1] | 824.97 | — |
| E-35 | 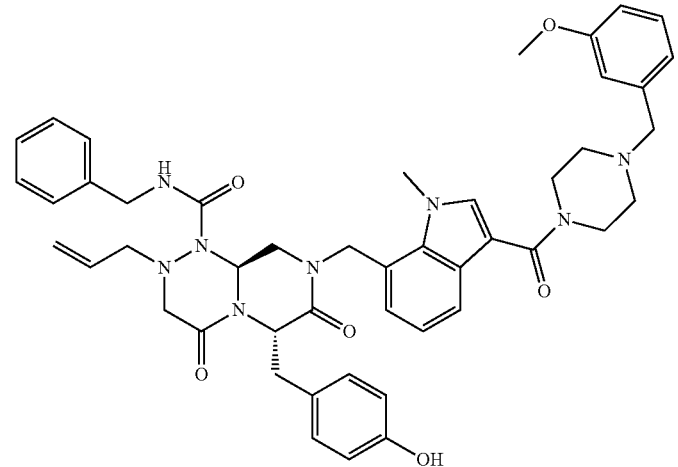 [SMILES: C=CCN1CC(=O)N2[C@@H](Cc3ccc(O)cc3)C(=O)N(Cc3cccc4c(C(=O)N5CCN(Cc6cccc(OC)c6)CC5)cn(C)c34)C[C@@H]2N1C(=O)NCc1ccccc1] | 824.97 | — |

TABLE 3-continued

| No. | Chemical Formula | M.W. | NMR |
|---|---|---|---|
| E-36 | | 824.97 | — |
| E-37 | | 780.91 | — |
| E-38 | | 796.92 | — |

TABLE 3-continued
| No. | Chemical Formula | M.W. | NMR |
|---|---|---|---|
| E-39 | 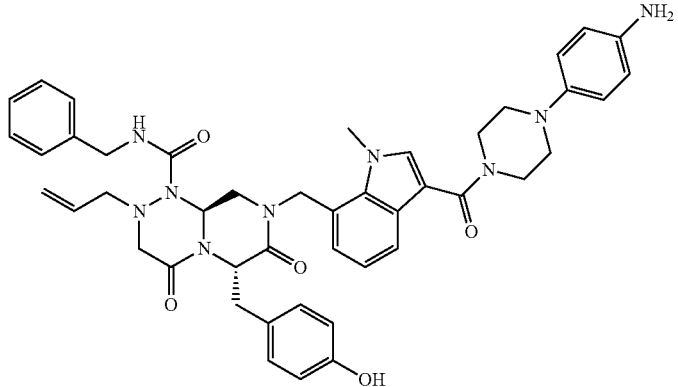 [SMILES: C=CCN1CC(=O)N2[C@@H](Cc3ccc(O)cc3)C(=O)N(Cc3cccc4c(C(=O)N5CCN(c6ccc(N)cc6)CC5)cn(C)c34)C[C@@H]2N1C(=O)NCc1ccccc1] | 795.93 | — |
| E-40 | 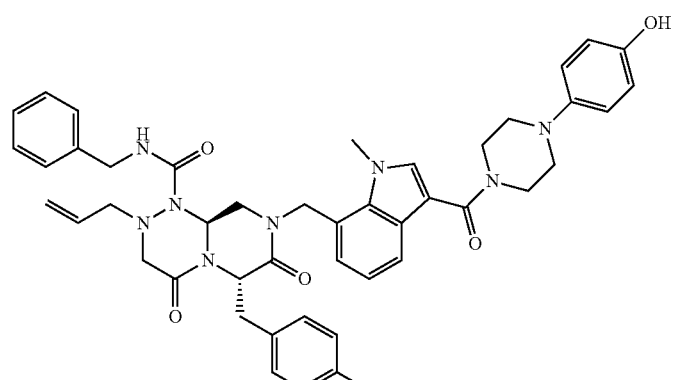 | 796.91 | — |
| E-41 | 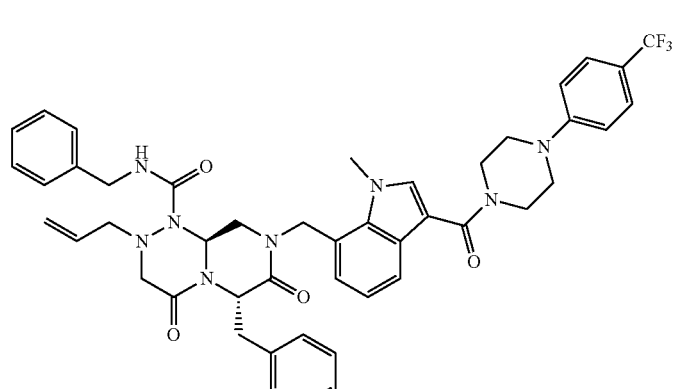 | 848.91 | — |
| E-42 | 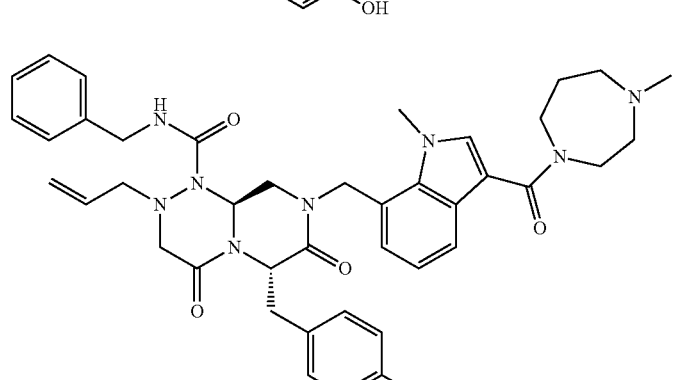 | 732.87 | — |

TABLE 3-continued

| No. | Chemical Formula | M.W. | NMR |
|---|---|---|---|
| E-43 | | 759.9 | 1H NMR(300 MHz, CDCL3, ppm, δ): 7.66(d, J = 8.392, 1H), 7.39~7.23(m, 6H), 7.17(m, J = 7.248, J = 8.801, 1H), 6.98(d, J = 8.392, 2H), 6.91(d, J = 7.248, 1H), 6.71~6.63(m, 3H), 5.60~5.31 (m, 4H), 5.08~4.83(m, 3H), 4.46~4.21(m, 4H), 3.97(s, 3H), 3.49~2.77(m, 13H), 2.22~1.44(m, 6H) |
| E-44 | | 801.93 | — |
| E-45 | | 816 | — |
| E-46 | | 856.07 | — |

TABLE 3-continued
| No. | Chemical Formula | M.W. | NMR |
|---|---|---|---|
| E-47 | 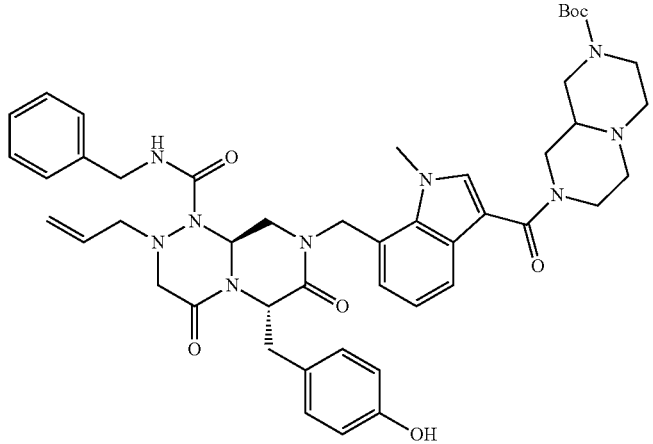 [SMILES: C=CCN1CC(=O)N2[C@@H](Cc3ccc(O)cc3)C(=O)N(Cc3cccc4c(C(=O)N5CCN6CCN(C(=O)OC(C)(C)C)CC6C5)cn(C)c34)C[C@@H]2N1C(=O)NCc1ccccc1] | 860.01 | — |
| E-48 | 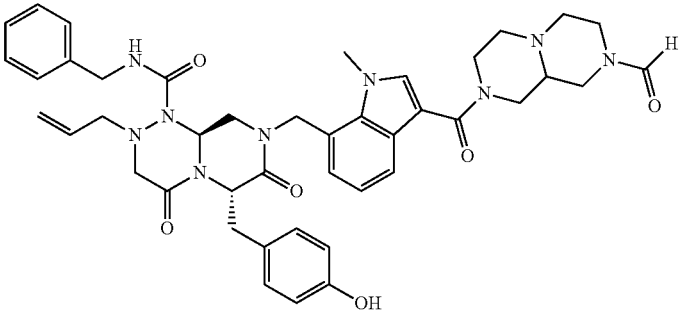 [SMILES: C=CCN1CC(=O)N2[C@@H](Cc3ccc(O)cc3)C(=O)N(Cc3cccc4c(C(=O)N5CCN6CCN(C=O)CC6C5)cn(C)c34)C[C@@H]2N1C(=O)NCc1ccccc1] | 787.91 | — |
| E-49 | 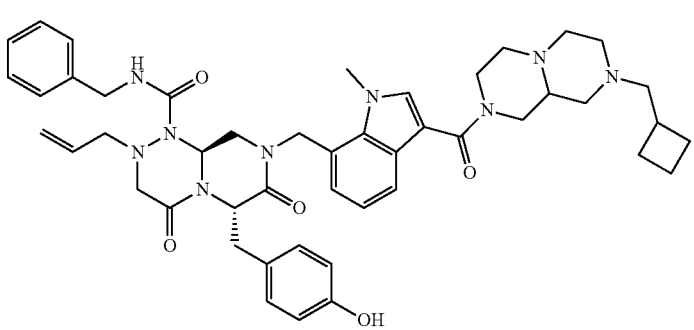 [SMILES: C=CCN1CC(=O)N2[C@@H](Cc3ccc(O)cc3)C(=O)N(Cc3cccc4c(C(=O)N5CCN6CCN(CC7CCC7)CC6C5)cn(C)c34)C[C@@H]2N1C(=O)NCc1ccccc1] | 828.01 | — |
| E-50 | 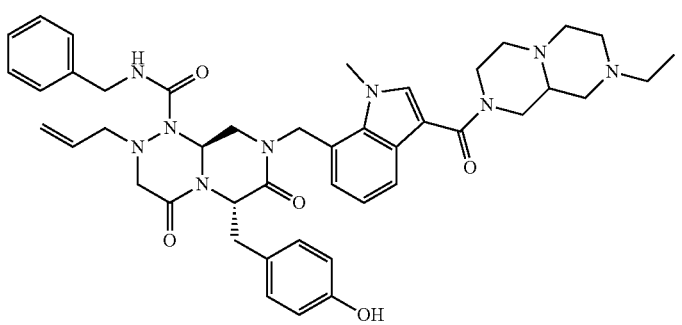 [SMILES: C=CCN1CC(=O)N2[C@@H](Cc3ccc(O)cc3)C(=O)N(Cc3cccc4c(C(=O)N5CCN6CCN(CC)CC6C5)cn(C)c34)C[C@@H]2N1C(=O)NCc1ccccc1] | 787.95 | — |

TABLE 3-continued
| No. | Chemical Formula | M.W. | NMR |
|---|---|---|---|
| E-51 | 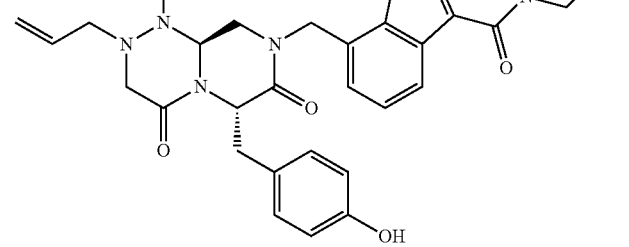 | 719.83 | 1H NMR(300 MHz, CDCl-d3, ppm, δ): 7.66(d, J = 7.8, 1H), 7.38~7.23(m, 6H), 7.14(dd, J = 7.5, 8.1, 1H), 6.99(d, J = 8.4, 2H), 6.84(d, J = 6.9, 1H), 6.72~6.67(m, 3H), 5.60~5.28(m, 4H), 5.10~4.87(m, 3H), 4.46~4.26(m, 2H), 4.14~4.05(m, 2H), 3.96~3.91(m, 4H), 3.53~3.25(m, 10H), 1.95~1.89(m,2H), 1.60~1.57(m, 2H). |
| E-52 | 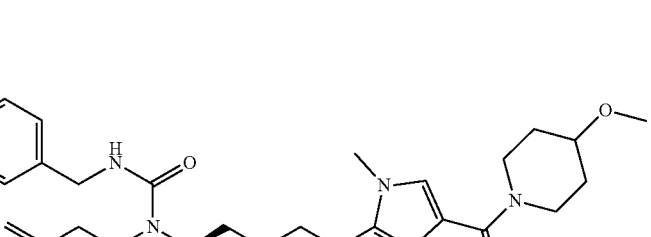 | 733.86 | — |
| E-53 | 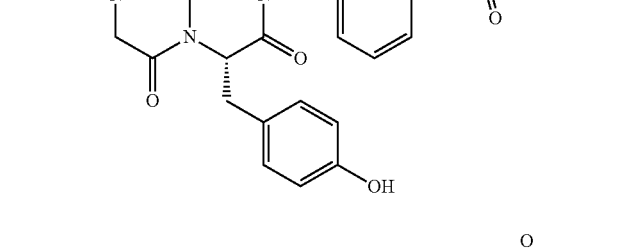 | 775.89 | — |
| E-54 | 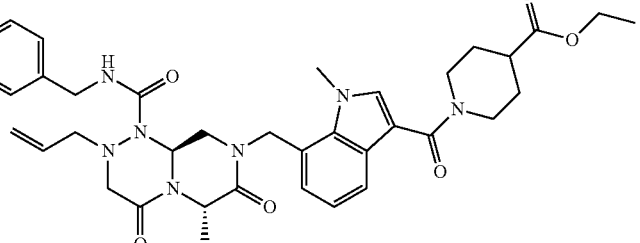 | 832 | — |

TABLE 3-continued

| No. | Chemical Formula | M.W. | NMR |
|---|---|---|---|
| E-55 | | 858.02 | — |
| E-56 | | 818.96 | — |
| E-57 | | 790.91 | — |
| E-58 | | 851.99 | — |

TABLE 3-continued

| No. | Chemical Formula | M.W. | NMR |
|---|---|---|---|
| E-59 | | 866.02 | 1H NMR(300 MHz, CDCl-d3, ppm, δ): 7.69~7.64(m, 3H), 7.33~7.20(m, 6H), 7.13(dd, J = 7.5, 7.8, 1H), 6.97(d, J = 8.4, 2H), 6.80(d, J = 7.2, 1H), 6.74~6.64(m, 5H), 6.32(d, J = 8.4, 1H), 5.59~5.47(m, 1H), 5.44~5.40(m, 1H), 5.35~5.24(m, 2H), 5.13~5.04(m, 2H), 4.88(d, J = 17, 1H), 4.43~4.25(m, 5H), 3.92(s, 3H), 3.53~3.20(m, 8H), 3.14~3.06(m, 2H), 3.00(s, 6H), 2.07~2.04(m, 2H), 1.59~1.51(m, 2H). |
| E-60 | | 921.1 | 1H NMR(300MHz, CDCl-d3, ppm, δ): 7.70~7.64(m, 3H), 7.37~7.22(m, 6), 7.13(dd, J = 7.8, 7.5, 1H), 6.89(d, J = 9.30, 2H), 6.80(d, J = 7.2, 1H), 6.72~6.67(m, 3H), 6.28(d, J = 8.4, 1H), 5.62~5.49(m, 1H), 5.45~5.40(m, 1H), 5.34~5.05(m, 4H), 4.89(d, J = 17.4, 1H), 4.44~4.25(m, 5H), 3.94(s, 3H), 3.54~3.21(m, 12H), 3.15~3.07(m, 2H), 2.58~2.55(m, 4H), 2.35(s, 3H), 2.09~2.05(m, 2H), 1.59~1.51(m, 2H). |
| E-61 | | 746.9 | — |
| E-62 | | 758.91 | — |

| No. | Chemical Formula | M.W. | NMR |
|---|---|---|---|
| E-63 | 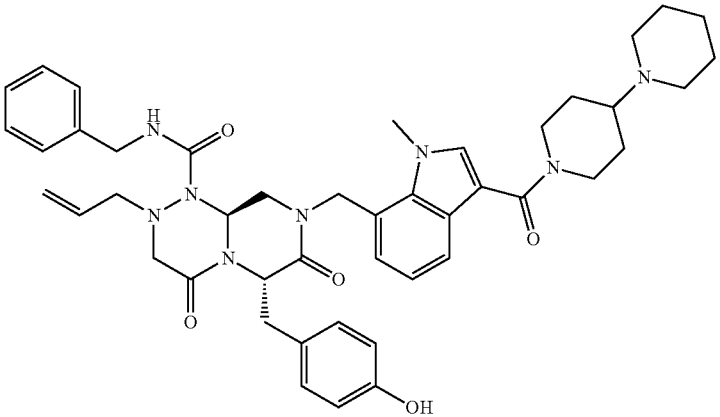 [SMILES: C=CCN1CC(=O)N2[C@@H](Cc3ccc(O)cc3)C(=O)N(Cc3cccc4c(C(=O)N5CCC(N6CCCCC6)CC5)cn(C)c34)C[C@@H]2N1C(=O)NCc1ccccc1] | 811.93 | — |
| E-64 | 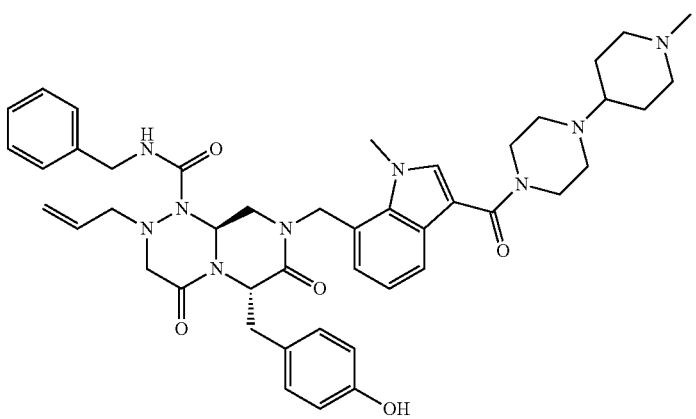 [SMILES: C=CCN1CC(=O)N2[C@@H](Cc3ccc(O)cc3)C(=O)N(Cc3cccc4c(C(=O)N5CCN(C6CCN(C)CC6)CC5)cn(C)c34)C[C@@H]2N1C(=O)NCc1ccccc1] | 786.98 | — |
| E-65 | 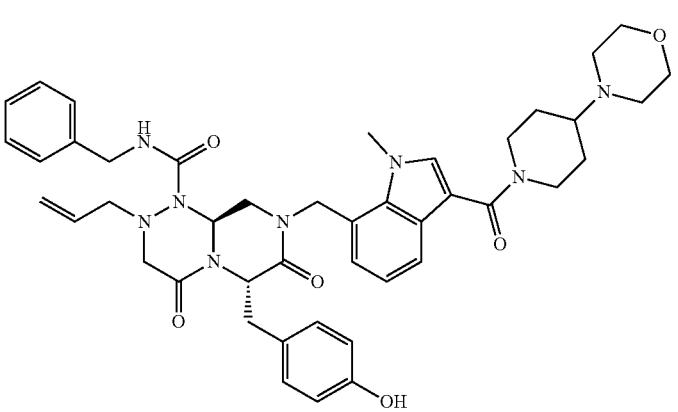 [SMILES: C=CCN1CC(=O)N2[C@@H](Cc3ccc(O)cc3)C(=O)N(Cc3cccc4c(C(=O)N5CCC(N6CCOCC6)CC5)cn(C)c34)C[C@@H]2N1C(=O)NCc1ccccc1] | 788.93 | — |
| E-66 | 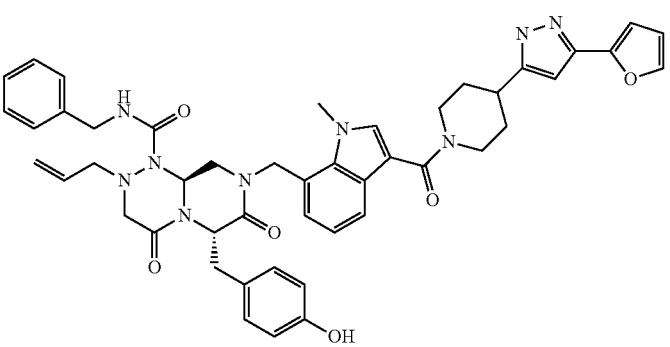 [SMILES: C=CCN1CC(=O)N2[C@@H](Cc3ccc(O)cc3)C(=O)N(Cc3cccc4c(C(=O)N5CCC(c6cc(-c7ccco7)n[nH]6)CC5)cn(C)c34)C[C@@H]2N1C(=O)NCc1ccccc1] | 835.38 | — |

TABLE 3-continued

| No. | Chemical Formula | M.W. | NMR |
|---|---|---|---|
| E-67 | | 772.93 | — |
| E-68 | | 744.88 | — |
| E-69 | | 744.88 | — |
| E-70 | | 691.78 | — |

TABLE 3-continued
| No. | Chemical Formula | M.W. | NMR |
|---|---|---|---|
| E-71 | 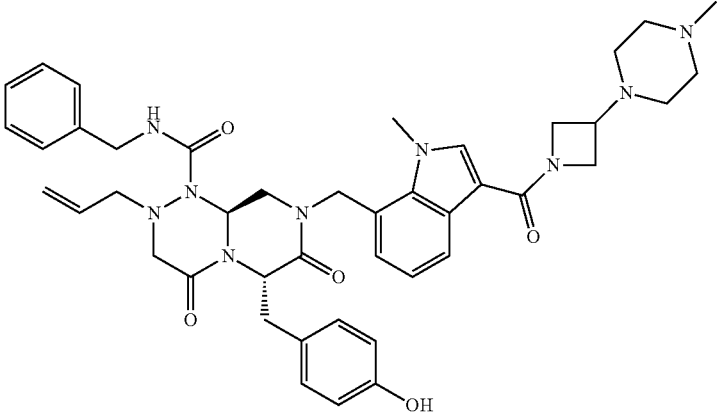 [SMILES: C=CCN1CC(=O)N2[C@@H](Cc3ccc(O)cc3)C(=O)N(Cc3cccc4c(C(=O)N5CC(N6CCN(C)CC6)C5)cn(C)c34)C[C@@H]2N1C(=O)NCc1ccccc1] | 773.92 | — |
| E-72 | 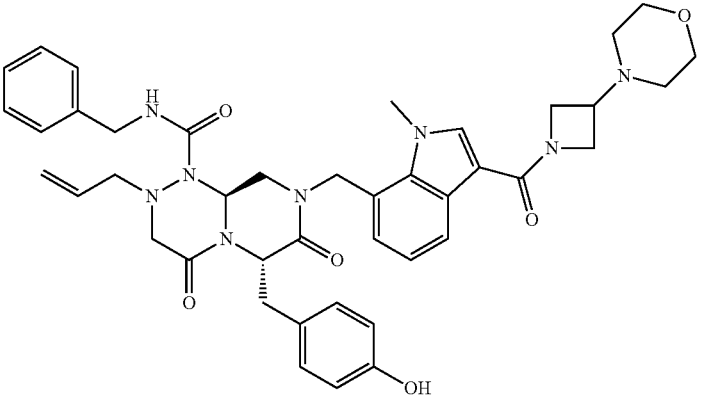 [SMILES: C=CCN1CC(=O)N2[C@@H](Cc3ccc(O)cc3)C(=O)N(Cc3cccc4c(C(=O)N5CC(N6CCOCC6)C5)cn(C)c34)C[C@@H]2N1C(=O)NCc1ccccc1] | 760.88 | — |
| E-73 | 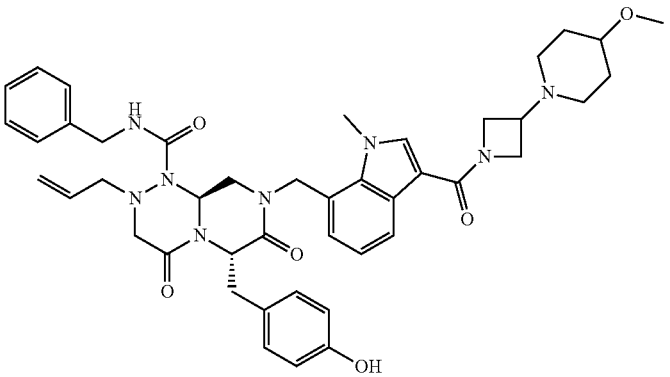 [SMILES: C=CCN1CC(=O)N2[C@@H](Cc3ccc(O)cc3)C(=O)N(Cc3cccc4c(C(=O)N5CC(N6CCC(OC)CC6)C5)cn(C)c34)C[C@@H]2N1C(=O)NCc1ccccc1] | 788.93 | 1H NMR(300 MHz, CDCl-d3, ppm, δ): 8.25(d, J = 8.1, 1H), 7.36~7.13(m, 7H), 7.00~6.93(m, 3H), 6.68~6.65(m, 3H), 5.56~5.41(m, 3H), 5.34~5.30(m, 1H), 5.05~4.76(m, 3H), 4.45~4.24(m, 4H), 4.13~4.11(m, 2H), 3.95(s, 3H), 3.48~3.15(m, 13H), 2.65~2.58(m, 2H), 2.14~2.08(m, 2H), 1.394~1.89 (m, 2H), 1.67~1.61(m, 2H). |

TABLE 4

| No. | Chemical Formula | M.W. | NMR |
|---|---|---|---|
| F-1 | | 663.77 | (300 MHz, CDCl3): 1.254 (s, 9H), 2.734-2.942 (m, 2H), 3.133-3.157 (d, J = 7.2 Hz, 4H), 3.175 (s, 3H), 3.361-3.514 (m, 4H), 4.620-5.299 (m, 5H), 5.642-5.898 (s, 1H), 6.008-6.036 (d, J = 8.4 Hz, 1H), 6.123(s, 1H), 6.225-7.329 (m, 16H), 7.566-7.593 (d, J = 8.1Hz, 1H) |
| F-2 | | 691.82 | — |
| F-3 | | 693.79 | 1H NMR(300MHz, CDCL3, ppm, δ): 7.79(d, J = 7.248, 1H), 7.38~7.12(m, 7H), 6.97(d, J = 8.392, 2H), 6.89(d, J = 7.248, 1H), 6.69~6.65(m, 3H), 5.59~5.51(m, 1H), 5.39~5.21(m, 3H), 5.11~5.06(m, 2H), 4.89(d, J = 17.923, 1H), 4.43~4.24(m, 2H), 3.94(s, 3H), 3.84(m, 2H), 3.72(m, 2H), 3.51~3.25(m, 9H), 3.19(s, 3H) |
| F-4 | | 693.79 | — |

TABLE 4-continued

| No. | Chemical Formula | M.W. | NMR |
|---|---|---|---|
| F-5 | | 708.57 | — |
| F-6 | | 707.82 | 1H NMR(300 MHz, CDCL3, ppm, δ): 8.022(d, J = 7.629, 1H), 7.52(s, 1H), 7.34~7.14(m, 6H), 6.90(d, J = 8.392, 2H), 6.90(d, J = 7.248, 1H), 6.80(t, J = 4.959, 1H), 6.70~6.68(m, 3H), 5.54~5.32(m, 4H), 5.05~4.78(m, 3H), 4.43~4.25(m, 2H), 3.92(s, 3H), 3.16~3.17(m, 15H), 1.90(m, 2H) |
| F-7 | | 723.82 | — |
| F-8 | | 735.87 | — |

TABLE 4-continued
| No. | Chemical Formula | M.W. | NMR |
|---|---|---|---|
| F-9 | 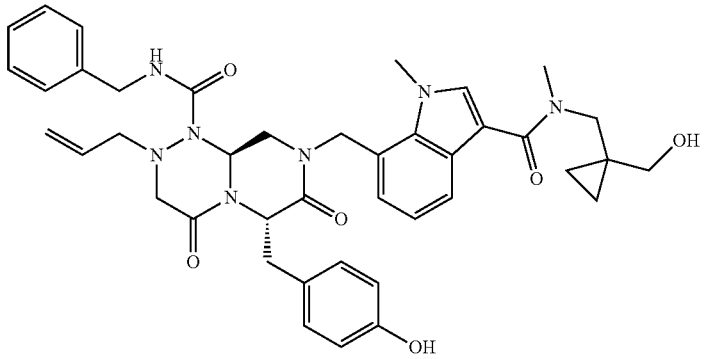 [SMILES: C=CCN1CC(=O)N2[C@@H](Cc3ccc(O)cc3)C(=O)N(Cc3cccc4c(C(=O)N(C)CC5(CO)CC5)cn(C)c34)C[C@@H]2N1C(=O)NCc1ccccc1] | 733.86 | — |
| F-10 | 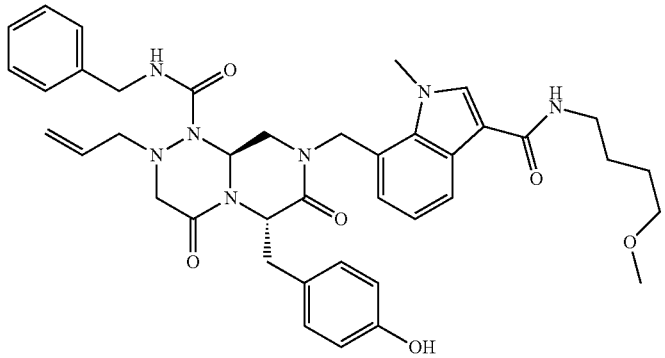 [SMILES: C=CCN1CC(=O)N2[C@@H](Cc3ccc(O)cc3)C(=O)N(Cc3cccc4c(C(=O)NCCCCOC)cn(C)c34)C[C@@H]2N1C(=O)NCc1ccccc1] | 721.84 | — |
| F-11 | 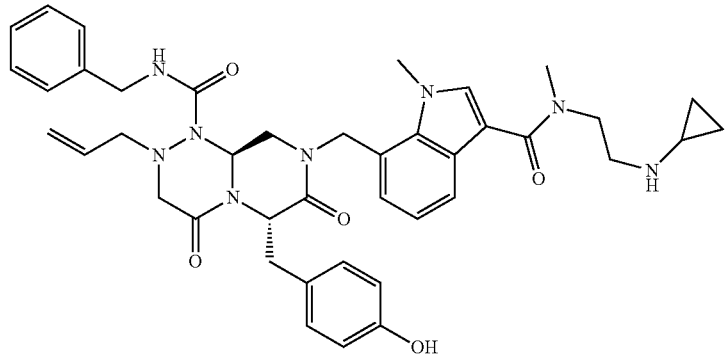 [SMILES: C=CCN1CC(=O)N2[C@@H](Cc3ccc(O)cc3)C(=O)N(Cc3cccc4c(C(=O)N(C)CCNC5CC5)cn(C)c34)C[C@@H]2N1C(=O)NCc1ccccc1] | 732.87 | — |
| F-12 | 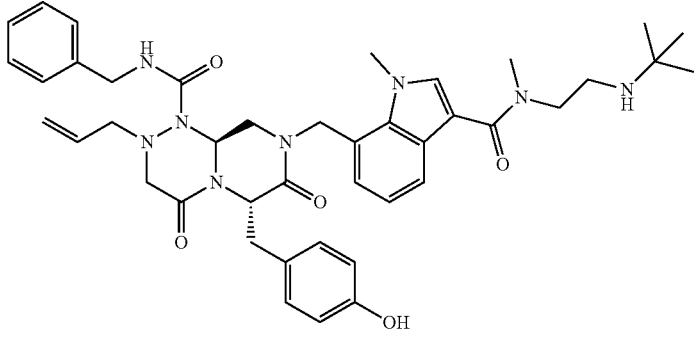 [SMILES: C=CCN1CC(=O)N2[C@@H](Cc3ccc(O)cc3)C(=O)N(Cc3cccc4c(C(=O)N(C)CCNC(C)(C)C)cn(C)c34)C[C@@H]2N1C(=O)NCc1ccccc1] | 748.91 | — |

TABLE 4-continued
| No. | Chemical Formula | M.W. | NMR |
|---|---|---|---|
| F-13 | 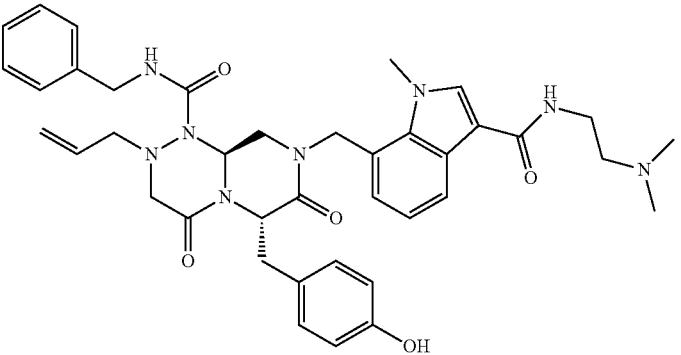 [SMILES: C=CCN1CC(=O)N2[C@@H](Cc3ccc(O)cc3)C(=O)N(Cc3cccc4c(C(=O)NCCN(C)C)cn(C)c34)C[C@@H]2N1C(=O)NCc1ccccc1] | 706.83 | — |
| F-14 | 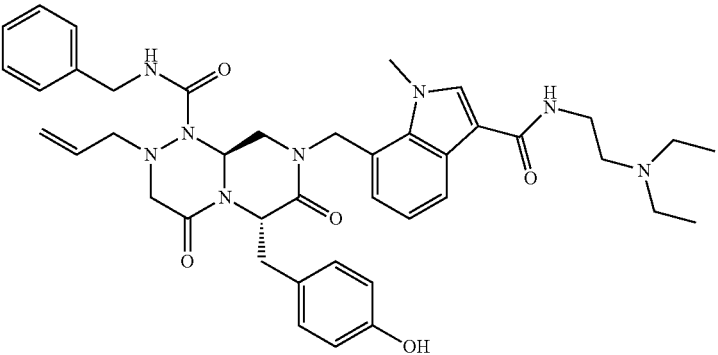 [SMILES: C=CCN1CC(=O)N2[C@@H](Cc3ccc(O)cc3)C(=O)N(Cc3cccc4c(C(=O)NCCN(CC)CC)cn(C)c34)C[C@@H]2N1C(=O)NCc1ccccc1] | 734.89 | — |
| F-15 | 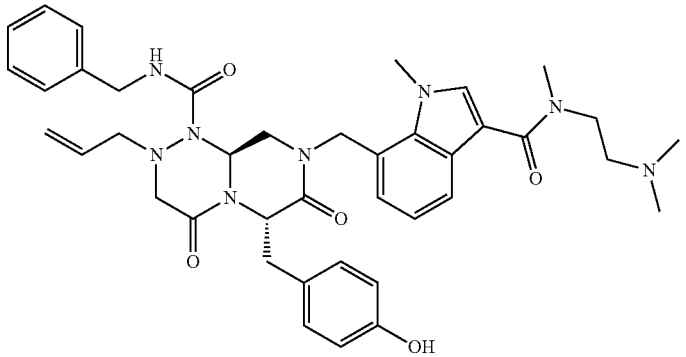 [SMILES: C=CCN1CC(=O)N2[C@@H](Cc3ccc(O)cc3)C(=O)N(Cc3cccc4c(C(=O)N(C)CCN(C)C)cn(C)c34)C[C@@H]2N1C(=O)NCc1ccccc1] | 720.86 | — |
| F-16 | 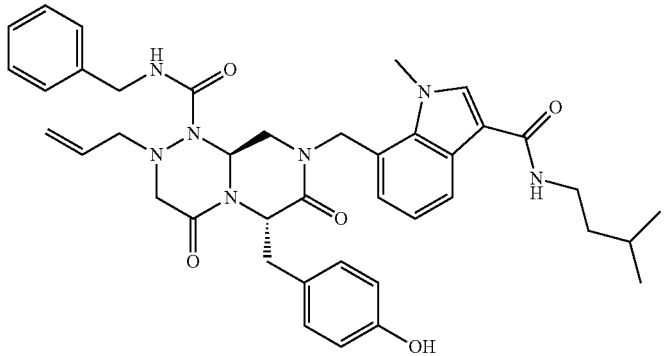 [SMILES: C=CCN1CC(=O)N2[C@@H](Cc3ccc(O)cc3)C(=O)N(Cc3cccc4c(C(=O)NCCC(C)C)cn(C)c34)C[C@@H]2N1C(=O)NCc1ccccc1] | 705.85 | — |

TABLE 4-continued
| No. | Chemical Formula | M.W. | NMR |
|---|---|---|---|
| F-17 | 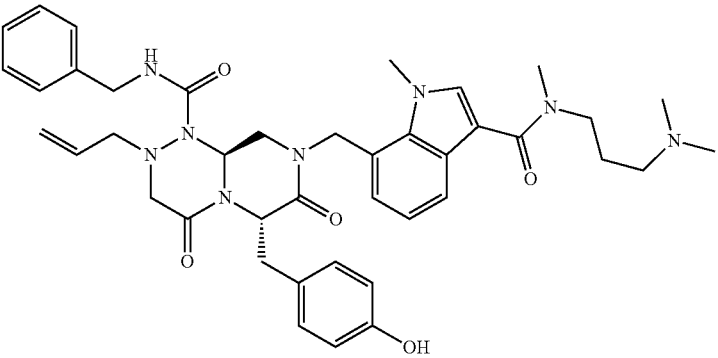 [SMILES: C=CCN1CC(=O)N2[C@@H](Cc3ccc(O)cc3)C(=O)N(Cc3cccc4c(C(=O)N(C)CCCN(C)C)cn(C)c34)C[C@@H]2N1C(=O)NCc1ccccc1] | 734.89 | — |
| F-18 | 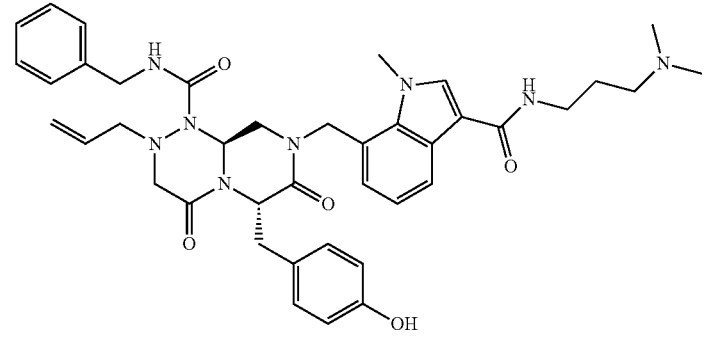 [SMILES: C=CCN1CC(=O)N2[C@@H](Cc3ccc(O)cc3)C(=O)N(Cc3cccc4c(C(=O)NCCCN(C)C)cn(C)c34)C[C@@H]2N1C(=O)NCc1ccccc1] | 720.86 | — |
| F-19 | 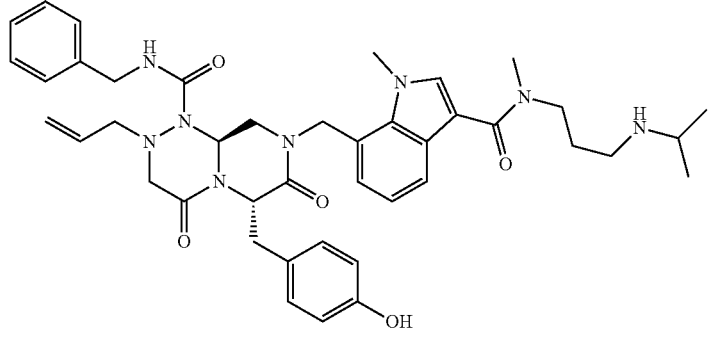 [SMILES: C=CCN1CC(=O)N2[C@@H](Cc3ccc(O)cc3)C(=O)N(Cc3cccc4c(C(=O)N(C)CCCNC(C)C)cn(C)c34)C[C@@H]2N1C(=O)NCc1ccccc1] | 748.91 | — |
| F-20 | 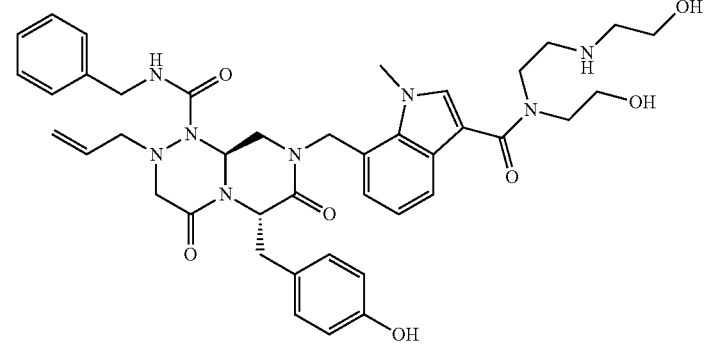 [SMILES: C=CCN1CC(=O)N2[C@@H](Cc3ccc(O)cc3)C(=O)N(Cc3cccc4c(C(=O)N(CCO)CCNCCO)cn(C)c34)C[C@@H]2N1C(=O)NCc1ccccc1] | 766.89 | — |

TABLE 4-continued

| No. | Chemical Formula | M.W. | NMR |
|---|---|---|---|
| F-21 | | 721.80 | — |
| F-22 | | 735.83 | — |
| F-23 | | 735.83 | — |
| F-24 | | 721.80 | — |

TABLE 4-continued

| No. | Chemical Formula | M.W. | NMR |
|---|---|---|---|
| F-25 | | 748.87 | — |
| F-26 | | 762.9 | 1H NMR(300MHz, CDCL3, ppm, δ): 7.79(d, J = 7.248, 1H), 7.40~7.11(m, 7H), 6.97~6.91(m, 2H), 6.73~6.60(m, 3H), 5.61~4.87(m, 8H), 4.44~4.25(m, 3H), 3.96(s, 3H), 3.77~3.64(m, 5H), 3.43~3.15(m, 10H), 3.02(m, 1H) 2.65(m, 2H), 2.49(m, 3H) |
| F-27 | | 761.91 | — |
| F-28 | | 775.94 | — |

TABLE 4-continued

| No. | Chemical Formula | M.W. | NMR |
|---|---|---|---|
| F-29 | | 762.90 | — |
| F-30 | | 775.94 | — |
| F-31 | | 789.96 | — |
| F-32 | | 798.92 | — |

TABLE 4-continued
| No. | Chemical Formula | M.W. | NMR |
|---|---|---|---|
| F-33 | 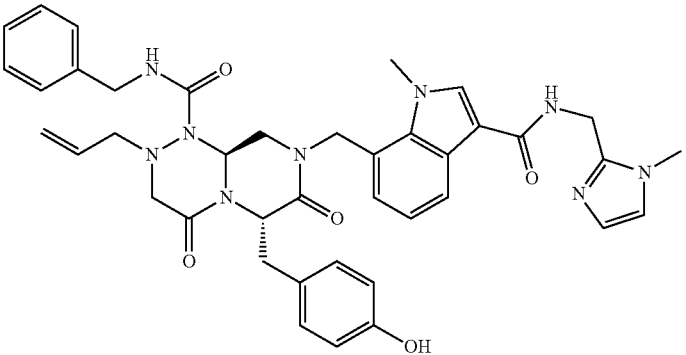 [SMILES: C=CCN1CC(=O)N2[C@@H](Cc3ccc(O)cc3)C(=O)N(Cc3cccc4c(C(=O)NCc5nccn5C)cn(C)c34)C[C@@H]2N1C(=O)NCc1ccccc1] | 729.83 | — |
| F-34 | 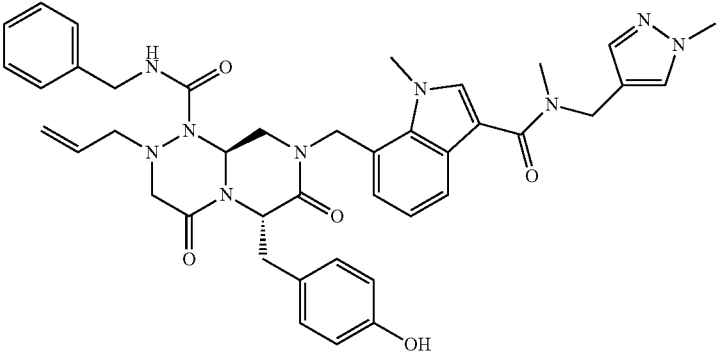 [SMILES: C=CCN1CC(=O)N2[C@@H](Cc3ccc(O)cc3)C(=O)N(Cc3cccc4c(C(=O)N(C)Cc5cnn(C)c5)cn(C)c34)C[C@@H]2N1C(=O)NCc1ccccc1] | 743.85 | — |
| F-35 | 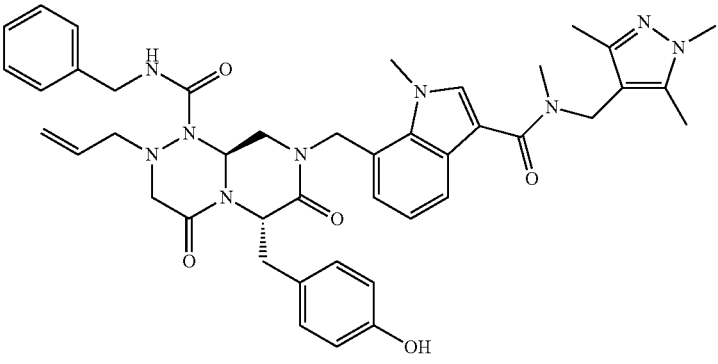 [SMILES: C=CCN1CC(=O)N2[C@@H](Cc3ccc(O)cc3)C(=O)N(Cc3cccc4c(C(=O)N(C)Cc5c(C)nn(C)c5C)cn(C)c34)C[C@@H]2N1C(=O)NCc1ccccc1] | 771.91 | — |
| F-36 | 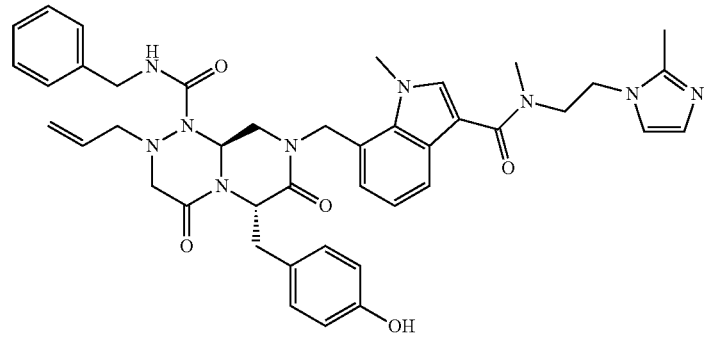 [SMILES: C=CCN1CC(=O)N2[C@@H](Cc3ccc(O)cc3)C(=O)N(Cc3cccc4c(C(=O)N(C)CCn5ccnc5C)cn(C)c34)C[C@@H]2N1C(=O)NCc1ccccc1] | 757.88 | — |

TABLE 4-continued

| No. | Chemical Formula | M.W. | NMR |
|---|---|---|---|
| F-37 | | 785.93 | — |
| F-38 | | 799.96 | — |
| F-39 | | 725.83 | — |
| F-40 | | 740.85 | — |

TABLE 4-continued
| No. | Chemical Formula | M.W. | NMR |
|---|---|---|---|
| F-41 | 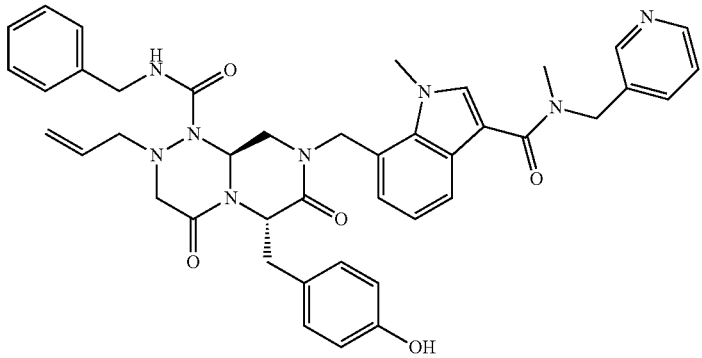 [SMILES: C=CCN1CC(=O)N2[C@@H](Cc3ccc(O)cc3)C(=O)N(Cc3cccc4c(C(=O)N(C)Cc5cccnc5)cn(C)c34)C[C@@H]2N1C(=O)NCc1ccccc1] | 740.85 | — |
| F-42 | 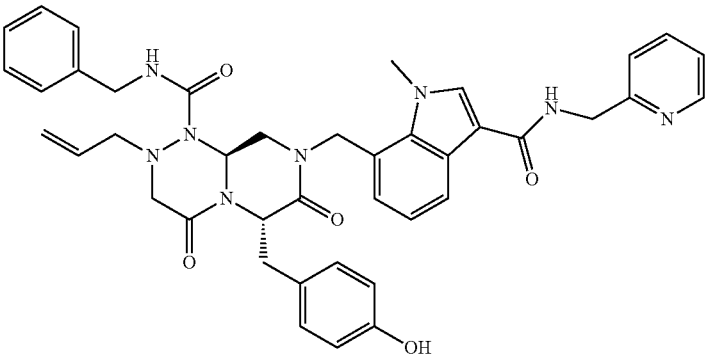 [SMILES: C=CCN1CC(=O)N2[C@@H](Cc3ccc(O)cc3)C(=O)N(Cc3cccc4c(C(=O)NCc5ccccn5)cn(C)c34)C[C@@H]2N1C(=O)NCc1ccccc1] | 726.82 | — |
| F-43 | 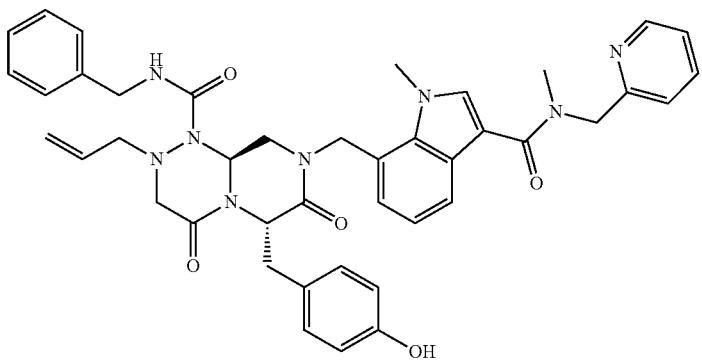 [SMILES: C=CCN1CC(=O)N2[C@@H](Cc3ccc(O)cc3)C(=O)N(Cc3cccc4c(C(=O)N(C)Cc5ccccn5)cn(C)c34)C[C@@H]2N1C(=O)NCc1ccccc1] | 740.85 | — |
| F-44 | 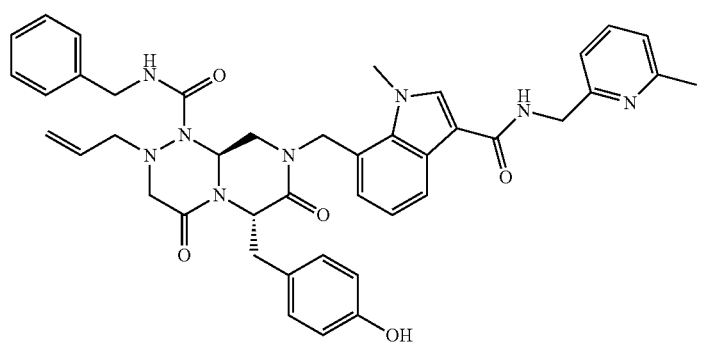 [SMILES: C=CCN1CC(=O)N2[C@@H](Cc3ccc(O)cc3)C(=O)N(Cc3cccc4c(C(=O)NCc5cccc(C)n5)cn(C)c34)C[C@@H]2N1C(=O)NCc1ccccc1] | 740.85 | — |

TABLE 4-continued

| No. | Chemical Formula | M.W. | NMR |
|---|---|---|---|
| F-45 | | 754.90 | — |
| F-46 | | 782.93 | — |
| F-47 | | 769.89 | 1H NMR(300MHz, CDCl-d3, ppm, δ): 8.12(d, J = 2.1, 1H), 8.01(d, J = 7.5, 1H), 7.52(dd, J = 9.0 2.4, 1H), 7.44(s, 1H), 7.36~7.19(m, 5H), 7.07(t, J = 7.8, 1H), 6.96(d, J = 8.7, 2H), 6.83(d, J = 6.9, 1H), 6.69~6.65(m, 3H), 6.48(d, J = 8.7, 1H), 6.43~6.36(m, 1H), 5.62~5.38(m, 2H), 5.32~5.28(m, 1H), 5.21~5.01(m, 3H), 4.87(d, J = 17, 1H), 4.54~4.22(m, 4H), 3.84(s, 3H), 3.51~3.14(m, 8H), 3.06(s, 6H). |
| F-48 | | 769.89 | — |

TABLE 4-continued

| No. | Chemical Formula | M.W. | NMR |
|---|---|---|---|
| F-49 | | 795.53 | — |
| F-50 | | 811.93 | — |
| F-51 | | 826.94 | — |
| F-52 | | 740.85 | — |

TABLE 4-continued

| No. | Chemical Formula | M.W. | NMR |
|---|---|---|---|
| F-53 | | 678.78 | — |
| F-54 | | 678.78 | — |
| F-55 | | 736.82 | — |
| F-56 | | 704.82 | — |

TABLE 4-continued
| No. | Chemical Formula | M.W. | NMR |
|---|---|---|---|
| F-57 | 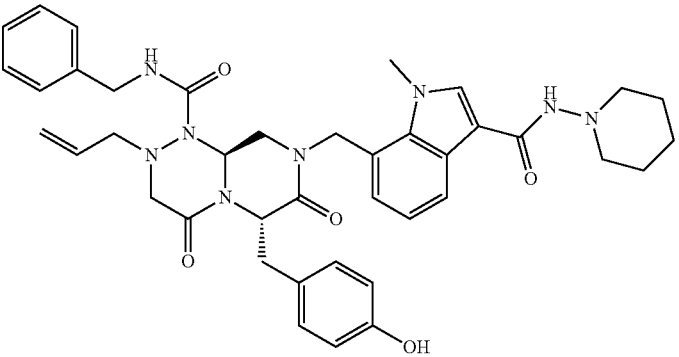 [SMILES: C=CCN1CC(=O)N2[C@@H](Cc3ccc(O)cc3)C(=O)N(Cc3cccc4c(C(=O)NN5CCCCC5)cn(C)c34)C[C@@H]2N1C(=O)NCc1ccccc1] | 718.84 | — |
| F-58 | 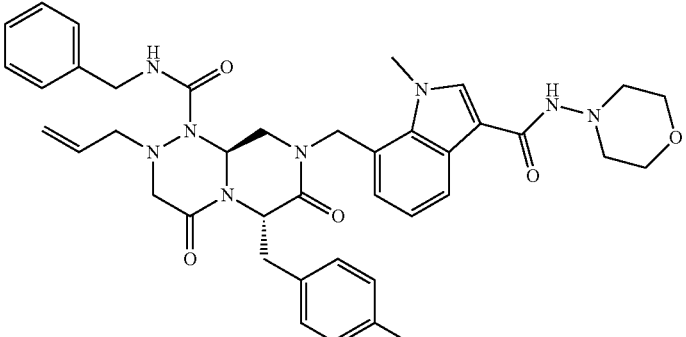 | 720.82 | — |
| F-59 | 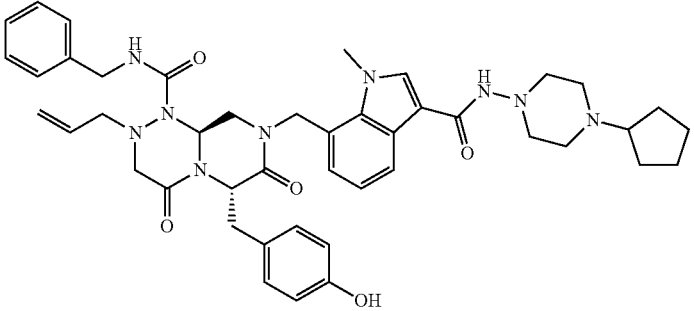 [SMILES: C=CCN1CC(=O)N2[C@@H](Cc3ccc(O)cc3)C(=O)N(Cc3cccc4c(C(=O)NN5CCN(C6CCCC6)CC5)cn(C)c34)C[C@@H]2N1C(=O)NCc1ccccc1] | 786.96 | — |
| F-60 | 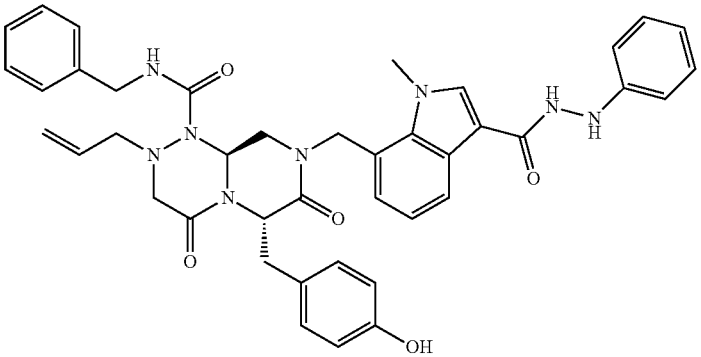 [SMILES: C=CCN1CC(=O)N2[C@@H](Cc3ccc(O)cc3)C(=O)N(Cc3cccc4c(C(=O)NNc5ccccc5)cn(C)c34)C[C@@H]2N1C(=O)NCc1ccccc1] | 726.82 | — |

TABLE 4-continued

| No. | Chemical Formula | M.W. | NMR |
|---|---|---|---|
| F-61 | | 818.96 | — |
| F-62 | | 774.95 | — |
| F-63 | | 776.92 | — |
| F-64 | | 760.88 | — |
| F-65 | | 790.91 | — |

TABLE 4-continued

| No. | Chemical Formula | M.W. | NMR |
|---|---|---|---|
| F-66 | | 866.02 | — |
| F-67 | | 921.1 | 1H NMR(300 MHz, CDCl-d3, ppm, δ): 8.06(d, J = 7.5, 1H), 7.53(s, 1H), 7.36~7.14(m, 8H), 6.98(d, J = 8.7, 2H), 6.89~6.85(m, 3H), 6.70~6.67(m, 3H), 6.24(d, J = 7.5, 1H), 5.58~5.42(m, 2H), 5.34~5.30(m, 1H), 5.26~5.20(m, 1H), 5.08~5.04(m, 2H), 4.90~4.85(m, 1H), 4.43~4.24(m, 4H), 3.87(s, 3H), 3.52~3.06(m, 15H), 2.58~2.55(m, 4H), 2.35(s, 3H), 2.08~2.04(m, 2H), 1.56~1.45(m, 2H). |
| F-68 | | 851.99 | — |

TABLE 5

| No. | Chemical Formula | M.W. | NMR |
|---|---|---|---|
| G-1 | | 730.79 | — |

TABLE 5-continued
| No. | Chemical Formula | M.W. | NMR |
|---|---|---|---|
| G-2 | 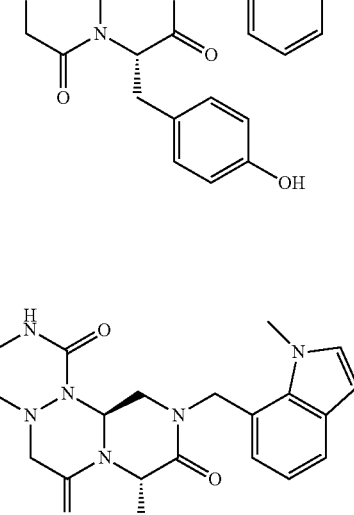 | 727.81 | — |
| G-3 | 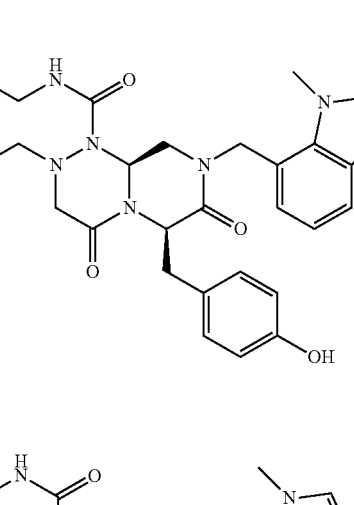 | 741.83 | — |
| G-4 | 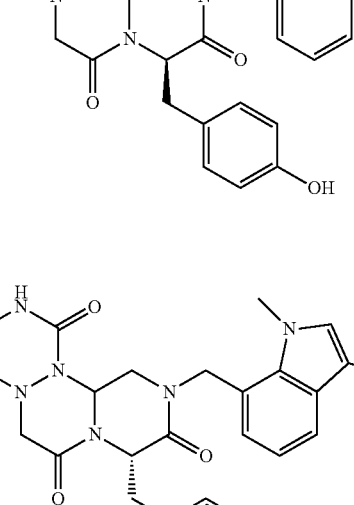 | 741.83 | — |
| G-5 | 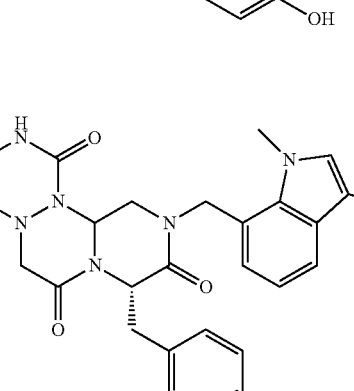 | 742.82 | — |

TABLE 5-continued

| No. | Chemical Formula | M.W. | NMR |
|---|---|---|---|
| G-6 | | 783.91 | — |
| G-7 | | 757.30 | — |
| G-8 | | 726.82 | — |
| G-9 | | 727.81 | — |

| No. | Chemical Formula | M.W. | NMR |
|---|---|---|---|
| G-10 | 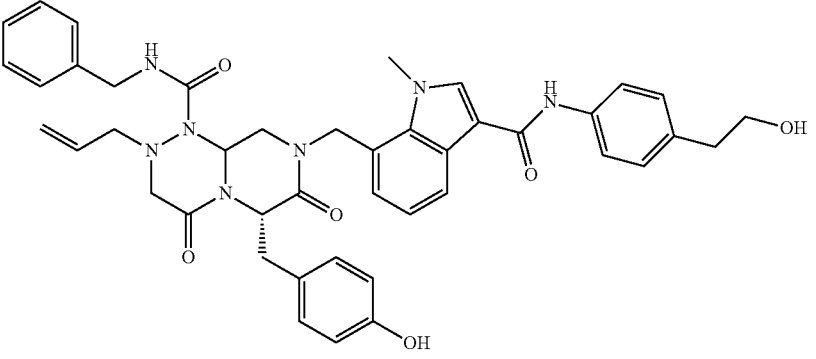 [SMILES: C=CCN1CC(=O)N2C(CN(Cc3cccc4c(C(=O)Nc5ccc(CCO)cc5)cn(C)c34)C(=O)[C@@H]2Cc2ccc(O)cc2)N1C(=O)NCc1ccccc1] | 755.86 | 1H NMR (300 MHz, DMSO-d6, ppm, δ): 9.67 (S, 1H), 6.29 (S, 1H), 8.14~8.16 (m, 2H), 7.82(t, J = 6.3 Hz, 1H), 7.64(d, J = 8.4 Hz, 2H), 7.28~7.33 (m, 2H), 7.14~7.22 (m, 5H), 7.07(t, J = 7.8 Hz, 1H), 6.90(d, J = 8.4 Hz, 2H), 6.71(d, J = 7.2 Hz, 1H), 6.62 (d, J = 8.4 Hz, 2H), 5.75~5.84 (m, 1H), 5.41~5.46 (m, 2H), 5.03~5.11 (m, 3H), 4.88(d, J = 15.9 Hz, 1H), 4.64(t, J = 5.1 Hz, 1H), 4.20(t, J = 6 Hz, 2H), 4.06 (S, 3H), 3.54~3.74 (m, 6H), 2.99~3.32 (m, 4H), 2.68(t, J = 6.9 Hz, 2H) |

TABLE 5-continued
| No. | Chemical Formula | M.W. | NMR |
|---|---|---|---|
| G-11 | 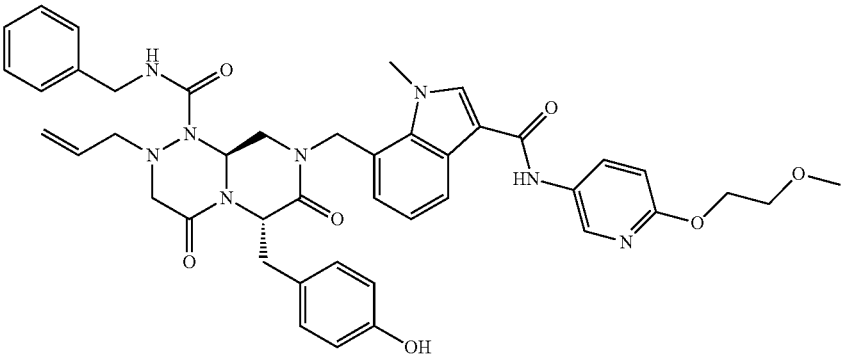 [SMILES: C=CCN1CC(=O)N2[C@@H](Cc3ccc(O)cc3)C(=O)N(Cc3cccc4c(C(=O)Nc5ccc(OCCOC)nc5)cn(C)c34)C[C@@H]2N1C(=O)NCc1ccccc1] | 786.35 | — |
| G-12 | 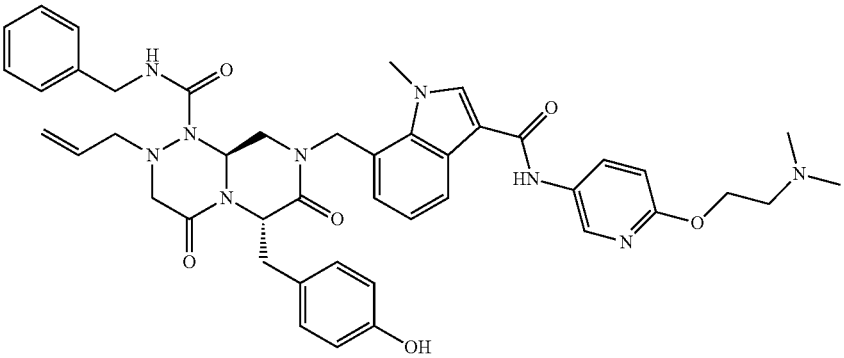 [SMILES: C=CCN1CC(=O)N2[C@@H](Cc3ccc(O)cc3)C(=O)N(Cc3cccc4c(C(=O)Nc5ccc(OCCN(C)C)nc5)cn(C)c34)C[C@@H]2N1C(=O)NCc1ccccc1] | 799.92 | — |
| G-13 | 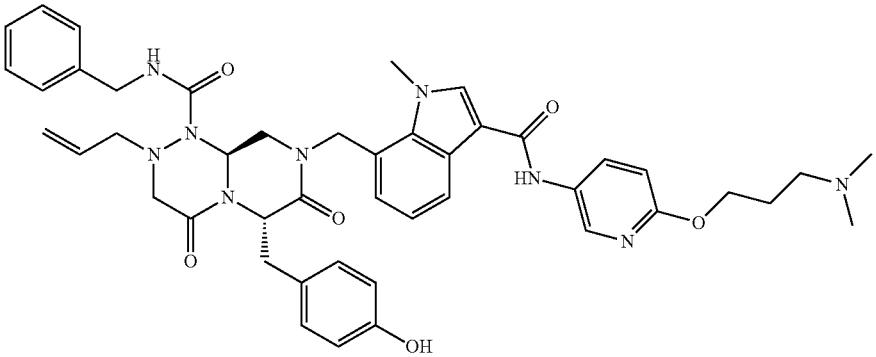 [SMILES: C=CCN1CC(=O)N2[C@@H](Cc3ccc(O)cc3)C(=O)N(Cc3cccc4c(C(=O)Nc5ccc(OCCCN(C)C)nc5)cn(C)c34)C[C@@H]2N1C(=O)NCc1ccccc1] | 813.94 | — |
| G-14 | 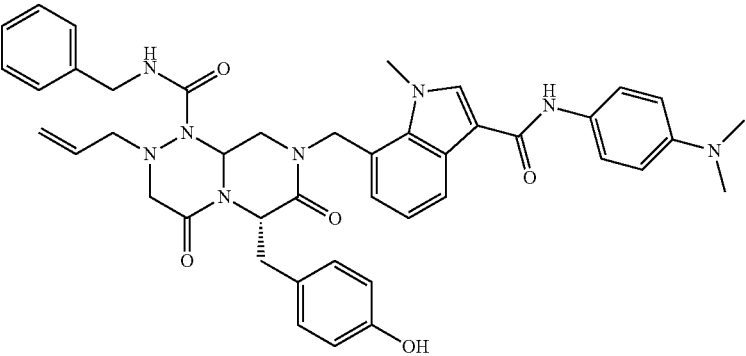 [SMILES: C=CCN1CC(=O)N2C(CN(Cc3cccc4c(C(=O)Nc5ccc(N(C)C)cc5)cn(C)c34)C(=O)[C@@H]2Cc2ccc(O)cc2)N1C(=O)NCc1ccccc1] | 754.88 | — |

TABLE 5-continued
| No. | Chemical Formula | M.W. | NMR |
|---|---|---|---|
| G-15 | 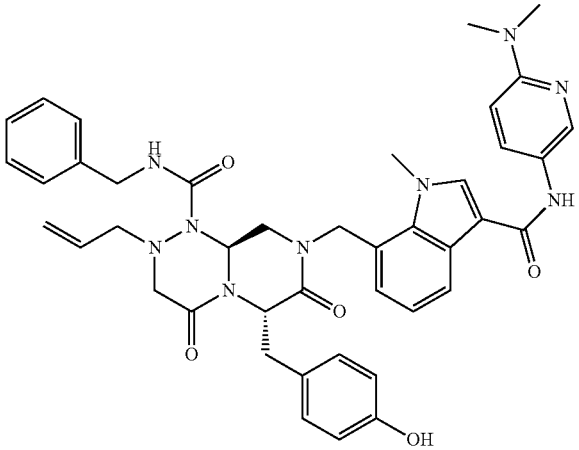 [SMILES: C=CCN1CC(=O)N2[C@@H](Cc3ccc(O)cc3)C(=O)N(Cc3cccc4c(C(=O)Nc5ccc(N(C)C)nc5)cn(C)c34)C[C@@H]2N1C(=O)NCc1ccccc1] | 755.86 | 1H NMR (300 MHz, CDCl3, ppm, δ) 8.14 (d, J = 2.4Hz, 2H), 8.04(d, J = 7.8 Hz, 1H)), 7.99 (m, 1H), 7.28~7.19 (m, 4H), 7.13(d, J = 6.9 Hz, 2H), 7.02(d, J = 7.5 Hz, 1H), 6.96(d, J = 8.7 Hz, 2H), 6.85 (d, J = 6.9 Hz, 1H), 6.79(m, 1H), 6.72 (d, J = 8.1 Hz, 2H), 6.56(d, J = 9.6 Hz, 1H), 5.49~5.64 (m, 1H), 5.27(t, J = 5.1 Hz, 2H), 5.05(d, J = 11.1 Hz, 2H), 4.85 (m, 1H), 4.15~4.34 (m, 2H), 3.71 (S, 3H), 3.14~3.50 (m, 8H), 3.09 (S, 6H) |
| G-16 | 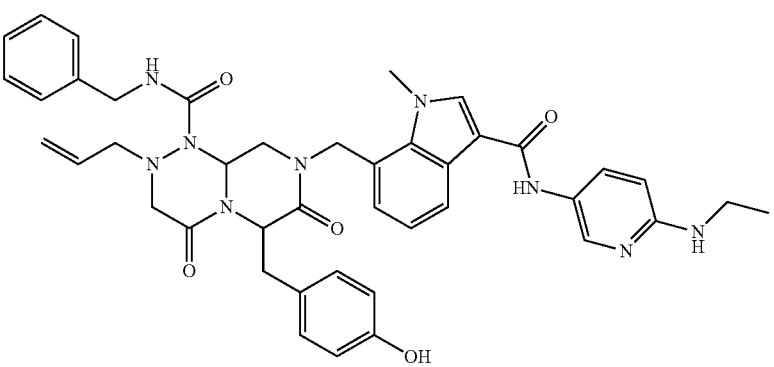 [SMILES: C=CCN1CC(=O)N2C(Cc3ccc(O)cc3)C(=O)N(Cc3cccc4c(C(=O)Nc5ccc(NCC)nc5)cn(C)c34)CC2N1C(=O)NCc1ccccc1] | 755.86 | — |

TABLE 5-continued

| No. | Chemical Formula | M.W. | NMR |
|---|---|---|---|
| G-17 | | 797.94 | — |
| G-18 | | 785.89 | — |
| G-19 | | 785.89 | — |
| G-20 | | 799.92 | — |

TABLE 5-continued

| No. | Chemical Formula | M.W. | NMR |
|---|---|---|---|
| G-21 | | 801.89 | — |
| G-22 | | 797.94 | — |
| G-23 | | 798.93 | — |

TABLE 5-continued

| No. | Chemical Formula | M.W. | NMR |
|---|---|---|---|
| G-24 | | 826.98 | — |
| G-25 | | 855.04 | — |
| G-26 | | 926.16 | — |
| G-27 | | 839.00 | — |

TABLE 5-continued
| No. | Chemical Formula | M.W. | NMR |
|---|---|---|---|
| G-28 | 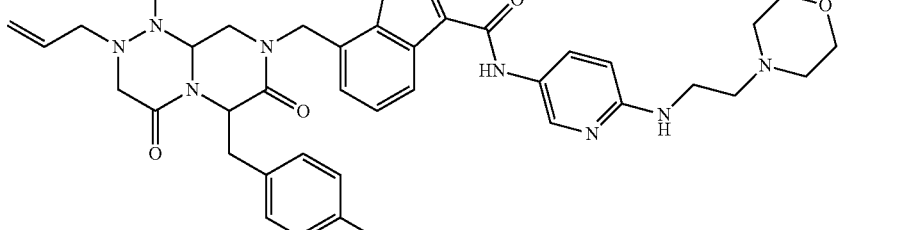 | 840.97 | — |
| G-29 | 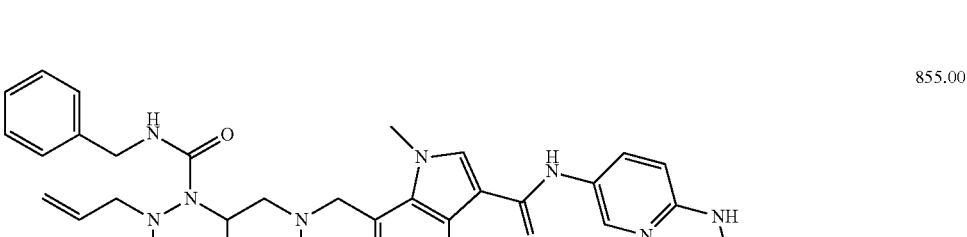 | 855.00 | — |
| G-30 | 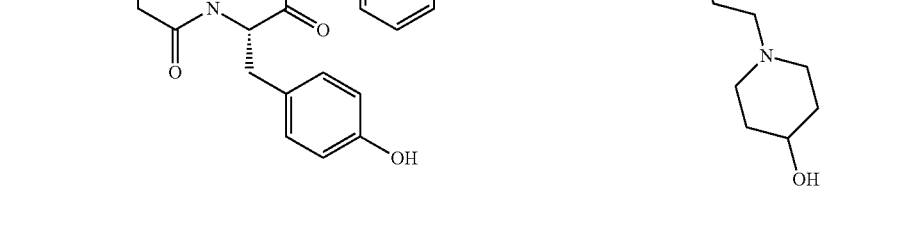 | 854.01 | — |
| G-31 | 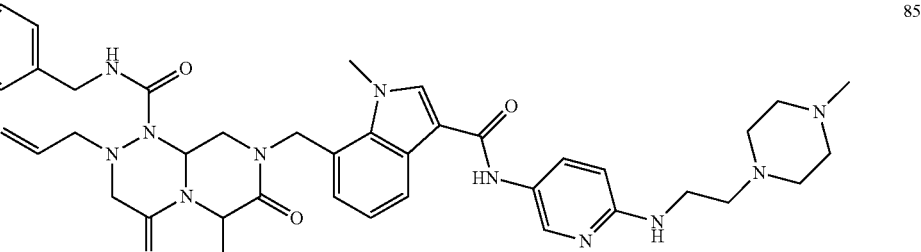 | 854.01 | — |

TABLE 5-continued
| No. | Chemical Formula | M.W. | NMR |
|---|---|---|---|
| G-32 | 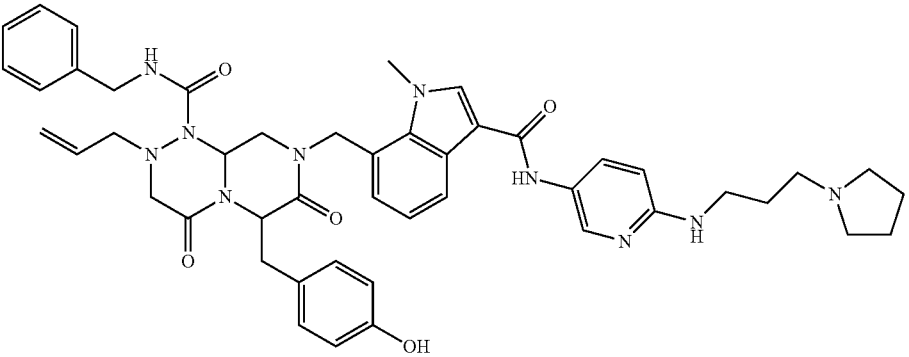 [SMILES: C=CCN1CC(=O)N2C(Cc3ccc(O)cc3)C(=O)N(Cc3cccc4c(C(=O)Nc5ccc(NCCCN6CCCC6)nc5)cn(C)c34)CC2N1C(=O)NCc1ccccc1] | 839 | — |
| G-33 | 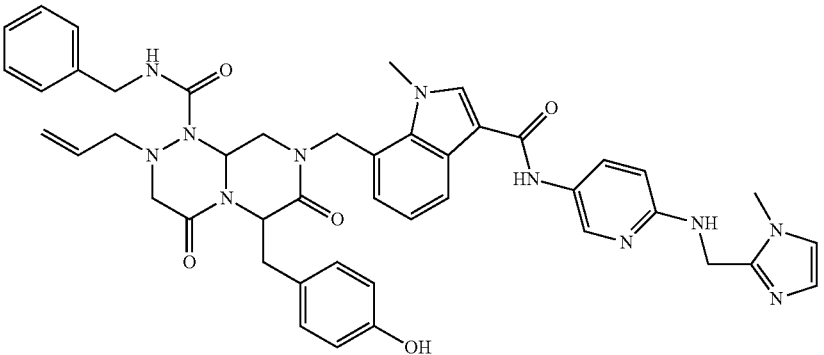 [SMILES: C=CCN1CC(=O)N2C(Cc3ccc(O)cc3)C(=O)N(Cc3cccc4c(C(=O)Nc5ccc(NCc6nccn6C)nc5)cn(C)c34)CC2N1C(=O)NCc1ccccc1] | 821.93 | — |
| G-34 | 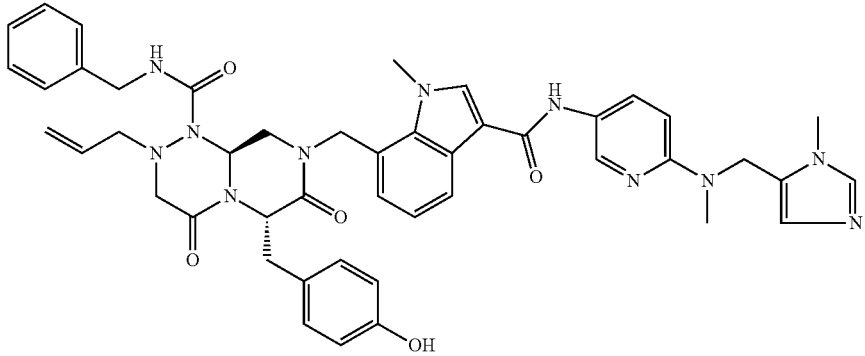 [SMILES: C=CCN1CC(=O)N2[C@@H](Cc3ccc(O)cc3)C(=O)N(Cc3cccc4c(C(=O)Nc5ccc(N(C)Cc6cncn6C)nc5)cn(C)c34)C[C@@H]2N1C(=O)NCc1ccccc1] | 835.95 | — |
| G-35 | 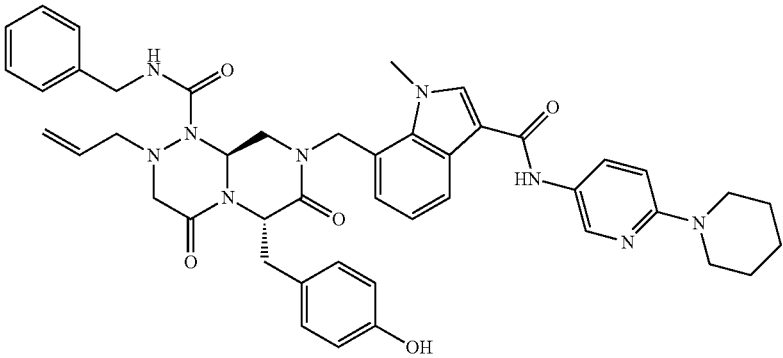 [SMILES: C=CCN1CC(=O)N2[C@@H](Cc3ccc(O)cc3)C(=O)N(Cc3cccc4c(C(=O)Nc5ccc(N6CCCCC6)nc5)cn(C)c34)C[C@@H]2N1C(=O)NCc1ccccc1] | 795.93 | — |

TABLE 5-continued
| No. | Chemical Formula | M.W. | NMR |
|---|---|---|---|
| G-36 | 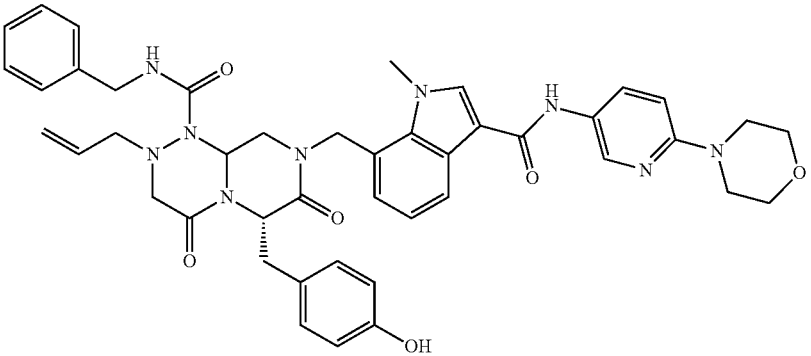 [SMILES: C=CCN1CC(=O)N2C(CN(Cc3cccc4c(C(=O)Nc5ccc(N6CCOCC6)nc5)cn(C)c34)C(=O)[C@@H]2Cc2ccc(O)cc2)N1C(=O)NCc1ccccc1] | 797.9 | 1H NMR (300 MHz, CDCl3, ppm, δ) 8.11~8.15 (m, 3H), 8.06(d, J = 7.8 Hz, 1H), 7.18~7.33 (m, 4H), 7.14(d, J = 6.9, 2H), 7.05 (t, J = 7.5 Hz, 1H), 6.98(d, J = 8.4 Hz, 2H), 6.85(d, J = 6.9 Hz, 1H), 6.65~6.75 (m, 4H), 5.52~5.63 (m, 1H), 5.30(t, J = 5.4 Hz, 2H), 4.93~4.99 (m, 4H), 4.17~4.38 (m, 2H), 3.84(t, J = 7.2 Hz, 4H), 3.74(S, 3H), 3.14~3.54 (m, 12H) |
| G-37 | 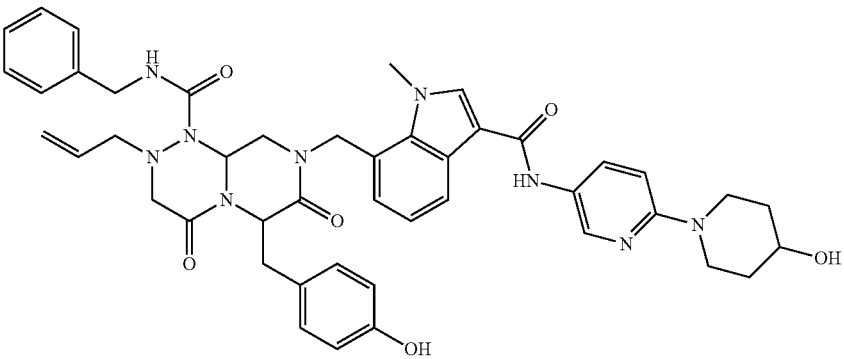 [SMILES: C=CCN1CC(=O)N2C(Cc3ccc(O)cc3)C(=O)N(Cc3cccc4c(C(=O)Nc5ccc(N6CCC(O)CC6)nc5)cn(C)c34)CC2N1C(=O)NCc1ccccc1] | 811.93 | — |

TABLE 5-continued
| No. | Chemical Formula | M.W. | NMR |
|---|---|---|---|
| G-38 | 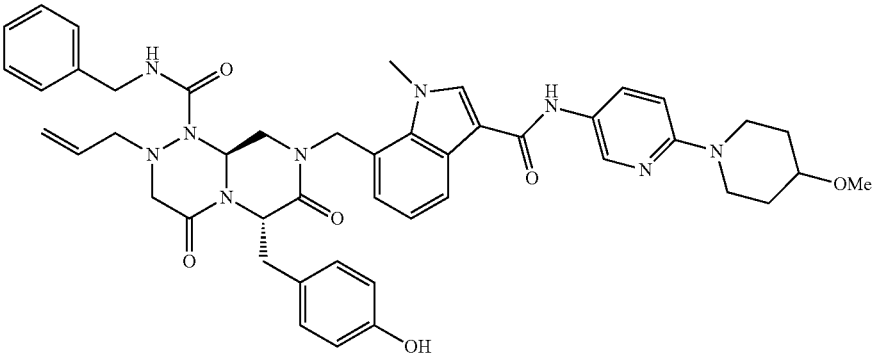 [SMILES: C=CCN1CC(=O)N2[C@@H](Cc3ccc(O)cc3)C(=O)N(Cc3cccc4c(C(=O)Nc5ccc(N6CCC(OC)CC6)nc5)cn(C)c34)C[C@@H]2N1C(=O)NCc1ccccc1] | 825.95 | — |
| G-39 | 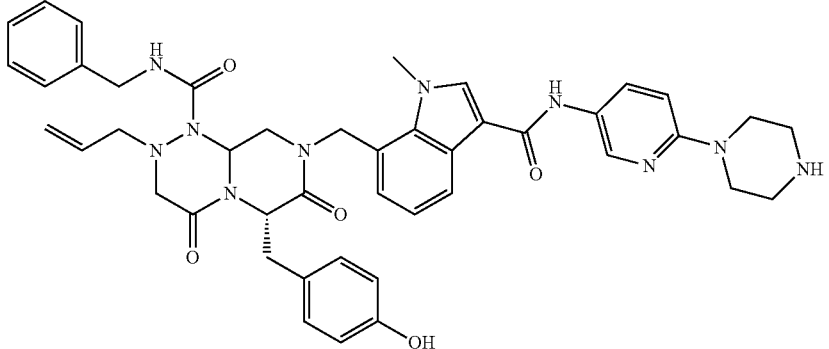 [SMILES: C=CCN1CC(=O)N2C(CN(Cc3cccc4c(C(=O)Nc5ccc(N6CCNCC6)nc5)cn(C)c34)C(=O)[C@@H]2Cc2ccc(O)cc2)N1C(=O)NCc1ccccc1] | 796.92 | — |
| G-40 | 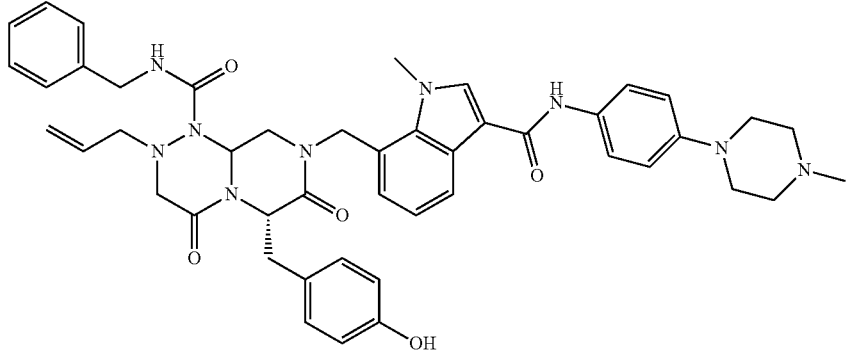 [SMILES: C=CCN1CC(=O)N2C(CN(Cc3cccc4c(C(=O)Nc5ccc(N6CCN(C)CC6)cc5)cn(C)c34)C(=O)[C@@H]2Cc2ccc(O)cc2)N1C(=O)NCc1ccccc1] | 809.95 | — |
| G-41 | 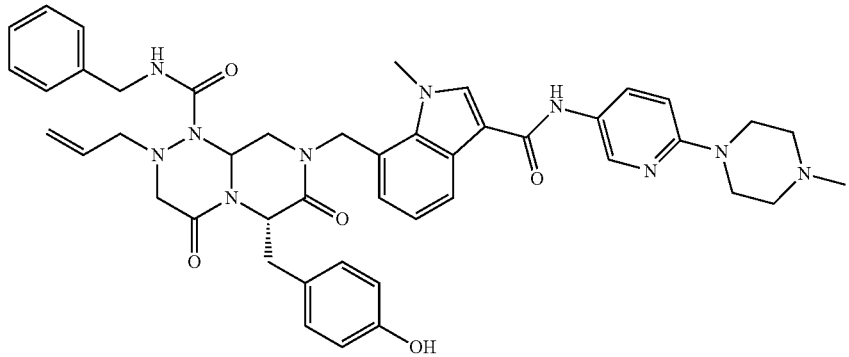 [SMILES: C=CCN1CC(=O)N2C(CN(Cc3cccc4c(C(=O)Nc5ccc(N6CCN(C)CC6)nc5)cn(C)c34)C(=O)[C@@H]2Cc2ccc(O)cc2)N1C(=O)NCc1ccccc1] | 810.94 | — |

TABLE 5-continued

| No. | Chemical Formula | M.W. | NMR |
|---|---|---|---|
| G-42 | | 824.97 | — |
| G-43 | | 839 | — |
| G-44 | | 840.47 | — |
| G-45 | | 839.00 | — |

TABLE 5-continued
| No. | Chemical Formula | M.W. | NMR |
|---|---|---|---|
| G-46 | 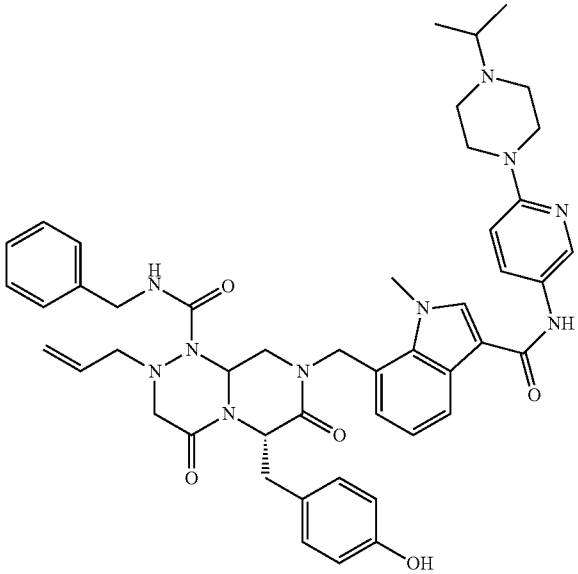 [SMILES: C=CCN1CC(=O)N2C(CN(Cc3cccc4c(C(=O)Nc5ccc(N6CCN(C(C)C)CC6)nc5)cn(C)c34)C(=O)[C@@H]2Cc2ccc(O)cc2)N1C(=O)NCc1ccccc1] | 839 | — |
| G-47 | 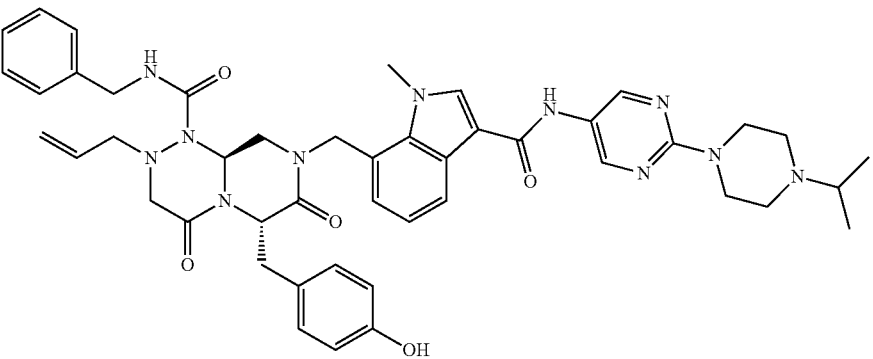 [SMILES: C=CCN1CC(=O)N2[C@@H](Cc3ccc(O)cc3)C(=O)N(Cc3cccc4c(C(=O)Nc5cnc(N6CCN(C(C)C)CC6)nc5)cn(C)c34)C[C@@H]2N1C(=O)NCc1ccccc1] | 839.98 | — |
| G-48 | 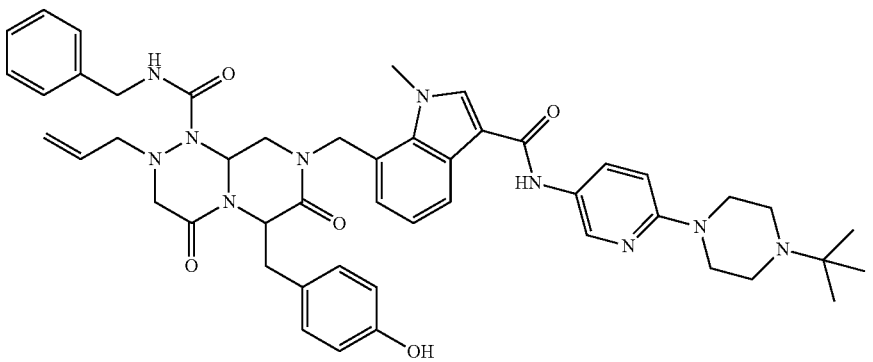 [SMILES: C=CCN1CC(=O)N2C(Cc3ccc(O)cc3)C(=O)N(Cc3cccc4c(C(=O)Nc5ccc(N6CCN(C(C)(C)C)CC6)nc5)cn(C)c34)CC2N1C(=O)NCc1ccccc1] | 853.02 | — |

TABLE 5-continued

| No. | Chemical Formula | M.W. | NMR |
|---|---|---|---|
| G-49 | | 836.98 | — |
| G-50 | | 865.03 | — |
| G-51 | | 865.03 | — |
| G-52 | | 881.08 | — |

TABLE 5-continued
| No. | Chemical Formula | M.W. | NMR |
|---|---|---|---|
| G-53 | 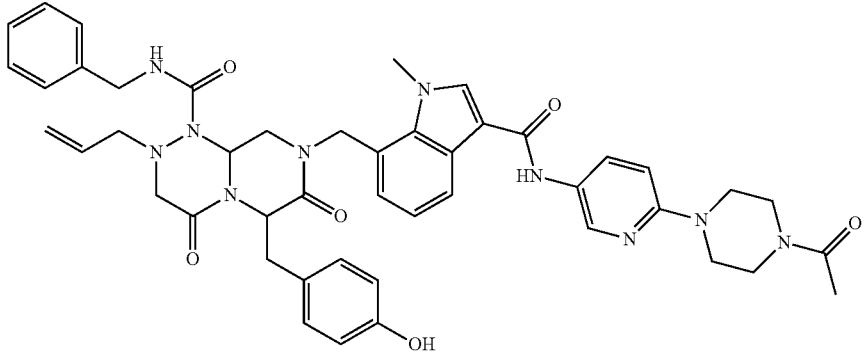 [SMILES: C=CCN1CC(=O)N2C(Cc3ccc(O)cc3)C(=O)N(Cc3cccc4c(C(=O)Nc5ccc(N6CCN(C(C)=O)CC6)nc5)cn(C)c34)CC2N1C(=O)NCc1ccccc1] | 838.95 | (300 MHz, CDCl3): 2.153 (s, 3H), 3.279-3.492 (m, 8H), 3.588 (s, 4H), 3.735-3.770 (dd, J = 12.0 Hz, J = 4.5 Hz, 2H), 3.827 (s, 3H), 4.195-4.404 (qdd, J = 41.7 Hz, J = 15.0 Hz, J = 5.7 Hz, 2H), 4.935-5.330 (m, 6H), 5.514-5.647 (m, 1H), 6.671-6.731 (m, 4H), 6.859-7.449 (m, 8H), 7.962 (s, 1H), 8.062-8.103 (m, 2H), 8.198-8.207 (d, J = 2.7 Hz, 1H) |
| G-54 | 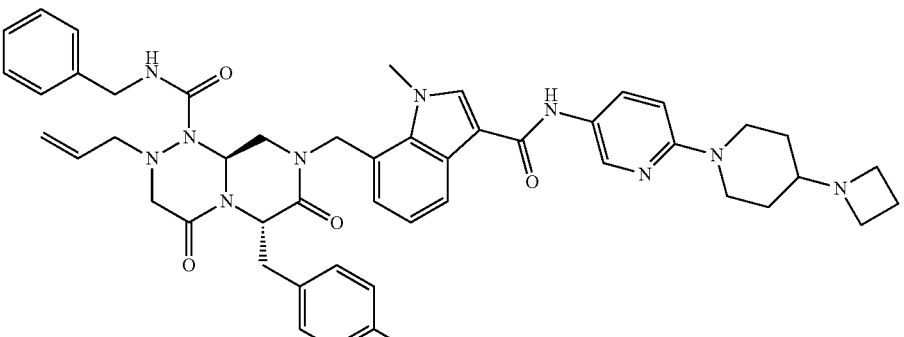 | 851.01 | — |

TABLE 5-continued
| No. | Chemical Formula | M.W. | NMR |
|---|---|---|---|
| G-55 | 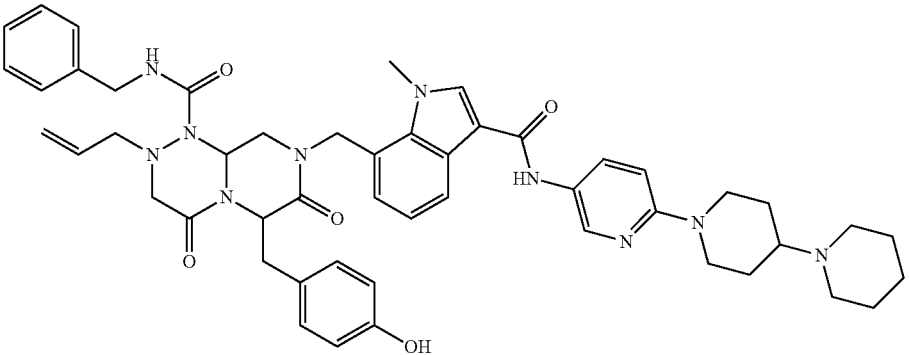 [SMILES: C=CCN1CC(=O)N2C(Cc3ccc(O)cc3)C(=O)N(Cc3cccc4c(C(=O)Nc5ccc(N6CCC(N7CCCCC7)CC6)nc5)cn(C)c34)CC2N1C(=O)NCc1ccccc1] | 879.06 | — |
| G-56 | 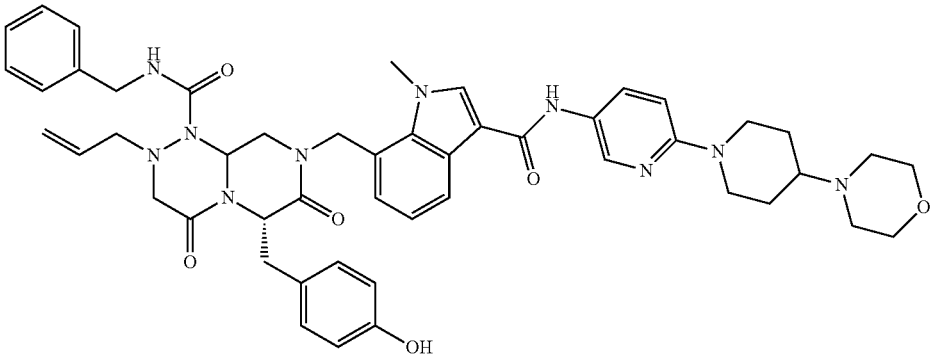 [SMILES: C=CCN1CC(=O)N2C(CN(Cc3cccc4c(C(=O)Nc5ccc(N6CCC(N7CCOCC7)CC6)nc5)cn(C)c34)C(=O)[C@@H]2Cc2ccc(O)cc2)N1C(=O)NCc1ccccc1] | 881.03 | — |
| G-57 | 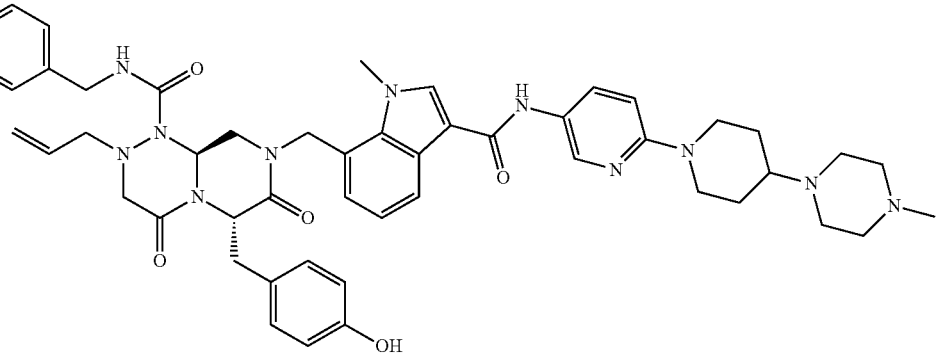 | 894.07 | — |
| G-58 | 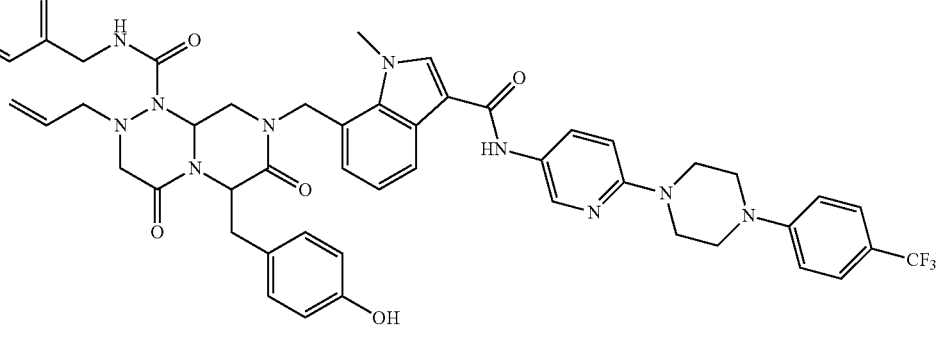 | 941.01 | — |

TABLE 5-continued
| No. | Chemical Formula | M.W. | NMR |
|---|---|---|---|
| G-59 | 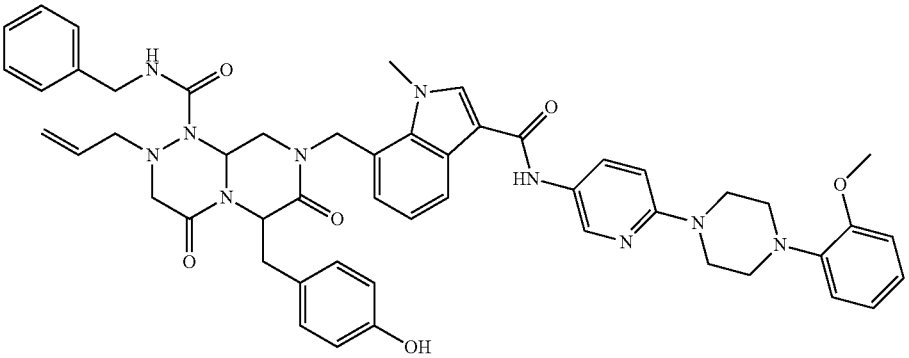 [SMILES: C=CCN1CC(=O)N2C(Cc3ccc(O)cc3)C(=O)N(Cc3cccc4c(C(=O)Nc5ccc(N6CCN(c7ccccc7OC)CC6)nc5)cn(C)c34)CC2N1C(=O)NCc1ccccc1] | 903.04 | (300 MHz, CDCl3): 3.138-3.529 (m, 8H), 3.692-3.752 (t, J = 5.1 Hz, 4H), 3.850 (s, 3H), 3.905 (s, 3H), 4.195-4.410 (qdd, J = 43.2 Hz, J = 14.7 Hz, J = 5.7 Hz, 2H), 4.909-5.332 (m, 6H), 5.498-5.661 (m, 1H), 6.708-8.183 (m, 20H) |
| G-60 | 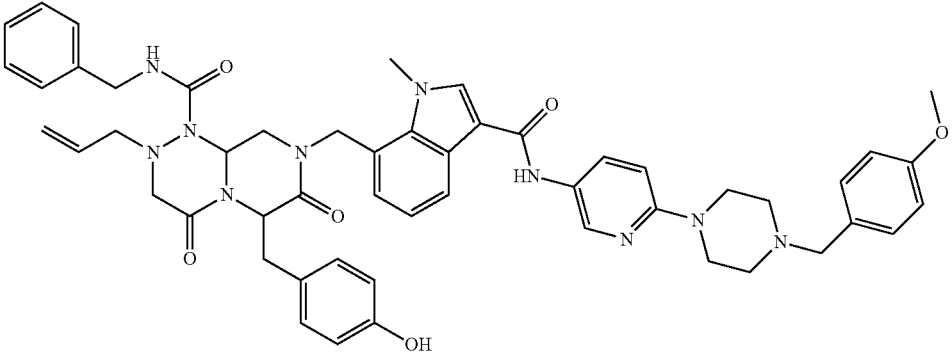 [SMILES: C=CCN1CC(=O)N2C(Cc3ccc(O)cc3)C(=O)N(Cc3cccc4c(C(=O)Nc5ccc(N6CCN(Cc7ccc(OC)cc7)CC6)nc5)cn(C)c34)CC2N1C(=O)NCc1ccccc1] | 917.06 | (300 MHz, CDCl3): d 2.558-2.590 (m, 4H), 3.260-3.514 (m, 8H), 3.816 (s, 3H), 3.826 (s, 3H), 4.176-4.402 (m, 2H), 4.919-5.347 (m, 4H), 5.505-5.667 (m, 1H), 6.671-7.357 (m, 16H), 7.764 (s, 1H), 8.032-8.135 (m, 3H) |

TABLE 5-continued
| No. | Chemical Formula | M.W. | NMR |
|---|---|---|---|
| G-61 | 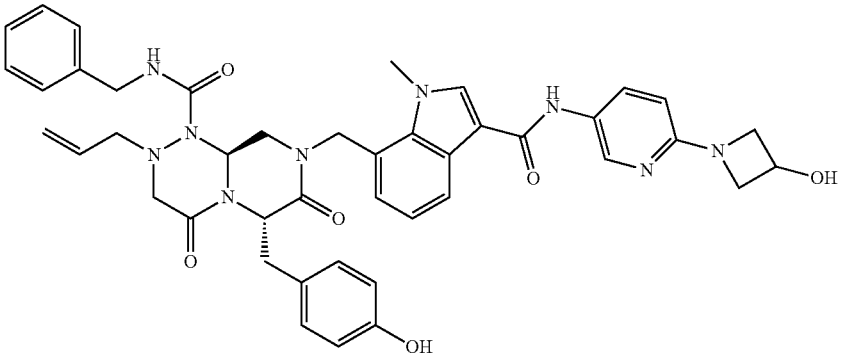 [SMILES: C=CCN1CC(=O)N2[C@@H](Cc3ccc(O)cc3)C(=O)N(Cc3cccc4c(C(=O)Nc5ccc(N6CC(O)C6)nc5)cn(C)c34)C[C@@H]2N1C(=O)NCc1ccccc1] | 783.87 | — |
| G-62 | 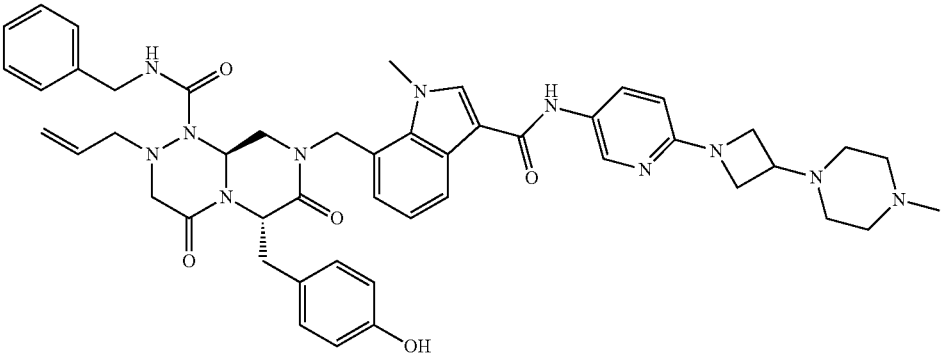 [SMILES: C=CCN1CC(=O)N2[C@@H](Cc3ccc(O)cc3)C(=O)N(Cc3cccc4c(C(=O)Nc5ccc(N6CC(N7CCN(C)CC7)C6)nc5)cn(C)c34)C[C@@H]2N1C(=O)NCc1ccccc1] | 866.02 | — |
| G-63 | 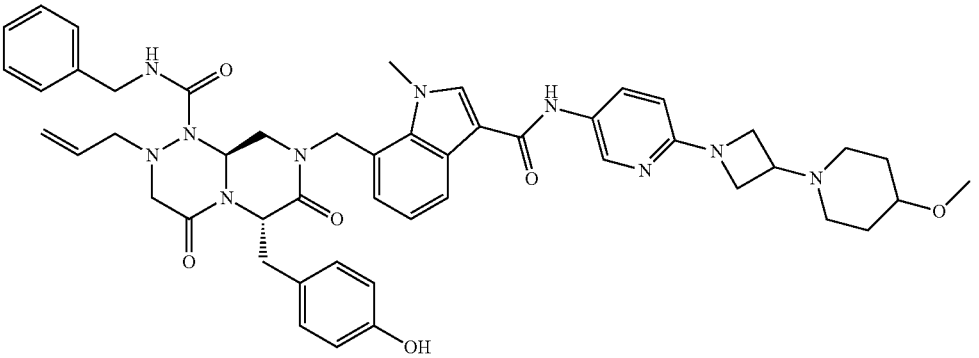 [SMILES: C=CCN1CC(=O)N2[C@@H](Cc3ccc(O)cc3)C(=O)N(Cc3cccc4c(C(=O)Nc5ccc(N6CC(N7CCC(OC)CC7)C6)nc5)cn(C)c34)C[C@@H]2N1C(=O)NCc1ccccc1] | 881.03 | — |
| G-64 | 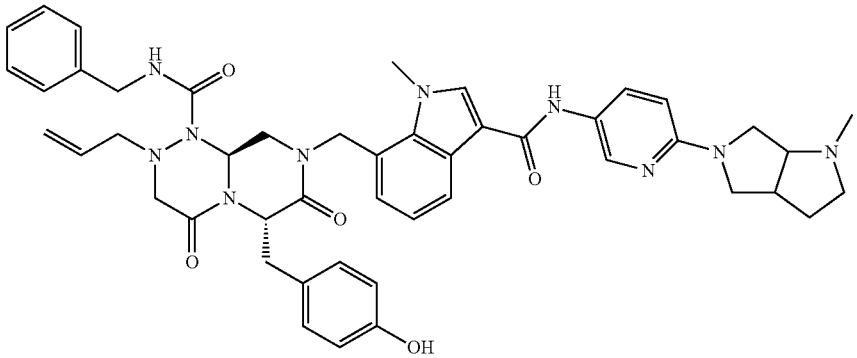 [SMILES: C=CCN1CC(=O)N2[C@@H](Cc3ccc(O)cc3)C(=O)N(Cc3cccc4c(C(=O)Nc5ccc(N6CC7CCN(C)C7C6)nc5)cn(C)c34)C[C@@H]2N1C(=O)NCc1ccccc1] | 836.97 | — |

TABLE 5-continued
| No. | Chemical Formula | M.W. | NMR |
|---|---|---|---|
| G-65 | 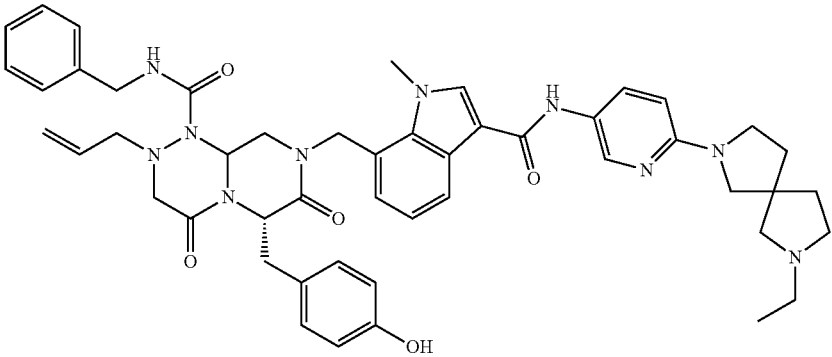 [SMILES: C=CCN1CC(=O)N2C(CN(Cc3cccc4c(C(=O)Nc5ccc(N6CCC7(CCN(CC)C7)C6)nc5)cn(C)c34)C(=O)[C@@H]2Cc2ccc(O)cc2)N1C(=O)NCc1ccccc1] | 864.44 | — |
| G-66 | 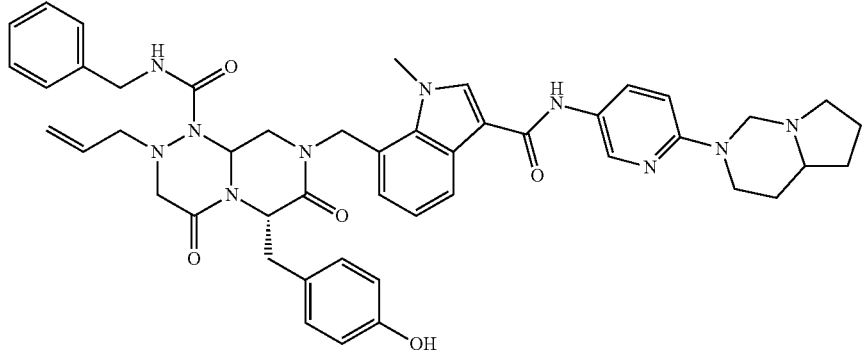 [SMILES: C=CCN1CC(=O)N2C(CN(Cc3cccc4c(C(=O)Nc5ccc(N6CCC7CCCN7C6)nc5)cn(C)c34)C(=O)[C@@H]2Cc2ccc(O)cc2)N1C(=O)NCc1ccccc1] | 836.98 | — |
| G-67 | 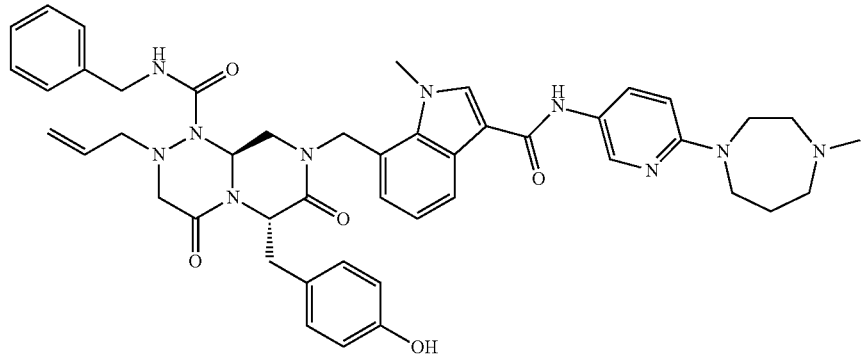 [SMILES: C=CCN1CC(=O)N2[C@@H](Cc3ccc(O)cc3)C(=O)N(Cc3cccc4c(C(=O)Nc5ccc(N6CCCN(C)CC6)nc5)cn(C)c34)C[C@@H]2N1C(=O)NCc1ccccc1] | 824.96 | — |
| G-68 | 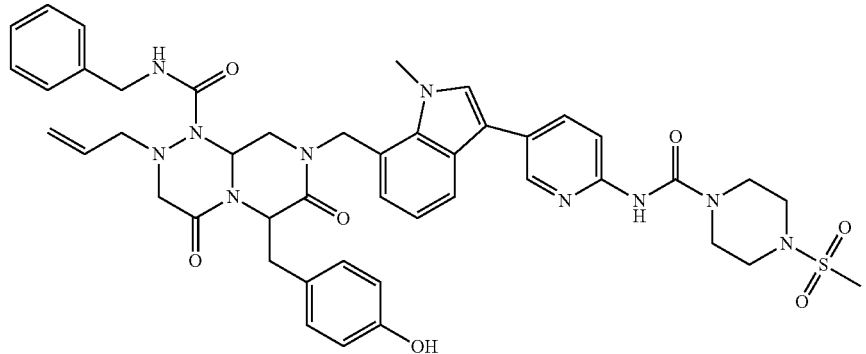 [SMILES: C=CCN1CC(=O)N2C(Cc3ccc(O)cc3)C(=O)N(Cc3cccc4c(-c5ccc(NC(=O)N6CCN(S(C)(=O)=O)CC6)nc5)cn(C)c34)CC2N1C(=O)NCc1ccccc1] | 875.01 | — |

TABLE 5-continued
| No. | Chemical Formula | M.W. | NMR |
|---|---|---|---|
| G-69 | 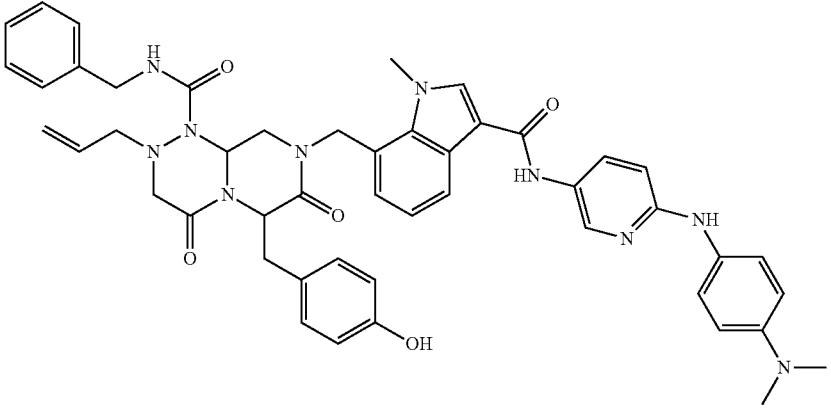 [SMILES: C=CCN1CC(=O)N2C(Cc3ccc(O)cc3)C(=O)N(Cc3cccc4c(C(=O)Nc5ccc(Nc6ccc(N(C)C)cc6)nc5)cn(C)c34)CC2N1C(=O)NCc1ccccc1] | 846.97 | — |
| G-70 | 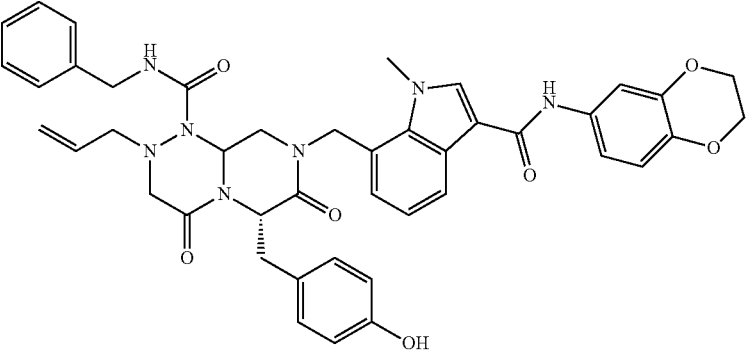 [SMILES: C=CCN1CC(=O)N2C(CN(Cc3cccc4c(C(=O)Nc5ccc6c(c5)OCCO6)cn(C)c34)C(=O)[C@@H]2Cc2ccc(O)cc2)N1C(=O)NCc1ccccc1] | 769.84 | — |
TABLE 6
| No. | Chemical Formula | M.W. | NMR |
|---|---|---|---|
| H-1 | 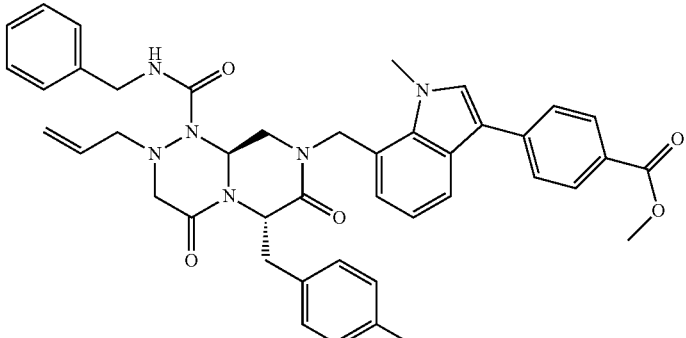 | 726.82 | — |

TABLE 6-continued
| No. | Chemical Formula | M.W. | NMR |
|---|---|---|---|
| H-2 | 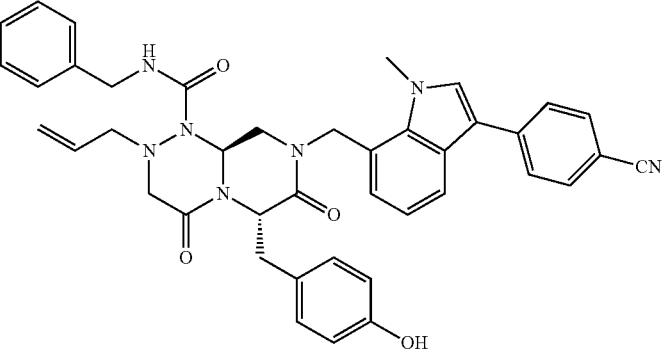 [SMILES: C=CCN1CC(=O)N2[C@@H](Cc3ccc(O)cc3)C(=O)N(Cc3cccc4c(-c5ccc(C#N)cc5)cn(C)c34)C[C@@H]2N1C(=O)NCc1ccccc1] | 693.79 | (CDCl3, 300 MHz) δ 7.85 (d, 1H, J = 8.1 Hz), 7.69 (s, 4H), 7.37 (d, 2H, J = 7.2 Hz), 7.39~7.22 (m, 4H), 7.22 (s, 1H), 7.17 (t, 1H, J = 8.1 Hz), 7.04 (d, 2H, J = 8.1 Hz), 6.95 (d, 1H, J = 7.2 Hz), 6.70~6.67 (m, 3H), 5.60~5.41 (m, 3H), 5.36 (t, 1H, J = 5.7 Hz), 5.05 (d, 1H, J = 11.1 Hz), 5.01 (d, 1H, J = 15.3 Hz), 4.83 (d, 1H, J = 16.8 Hz), 4.47 (dd, 1H, J = 15.0, 6.3 Hz), 4.32 (dd, 1H, J = 15.0, 6.0 Hz), 4.03 (s, 3H), 3.48~3.19 (m, 8H) |
| H-3 | 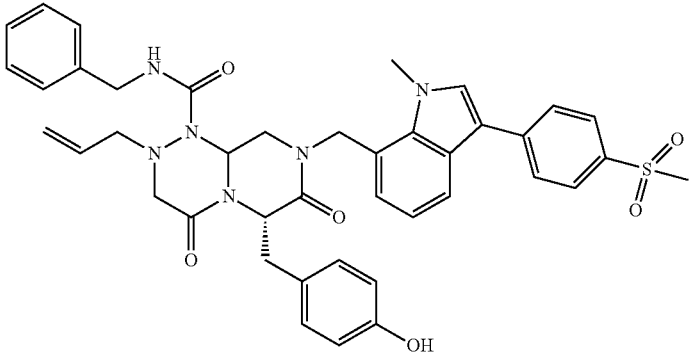 [SMILES: C=CCN1CC(=O)N2C(CN(Cc3cccc4c(-c5ccc(S(C)(=O)=O)cc5)cn(C)c34)C(=O)[C@@H]2Cc2ccc(O)cc2)N1C(=O)NCc1ccccc1] | 746.87 | (CDCl3, 300 MHz) δ 7.99 (d, 2H, J = 8.4 Hz), 7.88 (d, 1H, J = 7.2 Hz), 7.79 (dd, 2H, J = 8.7, 2.1 Hz), 7.39~7.22 (m, 5H), 7.04 (d, 2H, J = 8.4 Hz), 6.96 (d, 1H, J = 6.9 Hz), 6.71~6.68 (m, 1H), 6.69 (d, 2H, J = 8.4 Hz), 5.59~5.44 (m, 3H), 5.37 (t, 1H, J = 5.7 Hz), 5.05 (d, 1H, J = 9.6 Hz), 5.02 (d, 1H, J = 14.7 Hz), 4.84 (d, 1H, J = 17.1 Hz), 4.47 (dd, 1H, J = 15.0, 6.0 Hz), 4.33 (dd, 1H, J = 15.0, 6.0 Hz), 4.04 (s, 3H), 3.50~3.22 (m, 8H), 3.10 (s, 3H) |

TABLE 6-continued

| No. | Chemical Formula | M.W. | NMR |
| --- | --- | --- | --- |
| H-4 | | 815.94 | 300 MHz, CDCl3): 1.339-1.387 (t, J = 7.2 Hz, 3H), 3.186-3.487 (m, 6H), 4.027 (S, 3H), 4.252-4.464 (m, 4H),, 4.747-4.804 (d, J = 17.1 Hz, 1H), 4.932-4.981 (d, J = 14.7 Hz, 1H), 4.997-5.033 (d, J = 10.8 Hz, 1H), 5.342-5.379 (t, J = 5.4 Hz, 1H), 5.439-5.574 (m, 2H), 6.675-6.703 (m, 3H), 6.920-6.943 (d, J = 6.9 Hz, 1H), 7.012-7.040 (d, J = 8.4 Hz, 2H), 7.116-7.395 (m, 10H) |
| H-5 | | 847.98 | — |
| H-6 | | 719.83 | — |

TABLE 6-continued

| No. | Chemical Formula | M.W. | NMR |
|---|---|---|---|
| H-7 | | 713.83 | 1H NMR (300 MHz, CDCl3) δ 8.39-8.26 (s, 2H), 7.76-7.65 (d, J = 8.3 Hz, 1H), 7.45-7.19 (m, 4H), 7.16-7.05 (t, J = 7.6 Hz, 1H), 7.07-6.98 (m, 3H), 6.96-6.87 (d, J = 7.4 Hz, 1H), 6.74-6.61 (dd, J = 8.2, 2.1 Hz, 3H), 5.61-5.44 (m, 3H), 5.40-5.32 (t, J = 5.6 Hz, 1H), 5.06-4.96 (m, 1H), 4.96-4.86 (d, J = 15.0 Hz, 1H), 4.82-4.69 (d, J = 17.1 Hz, 1H), 4.50-4.23 (ddd, J = 44.6, 15.0, 5.9 Hz, 2H), 4.05-3.94 (s, 3H), 3.43-3.37 (d, J = 5.3Hz, 4H), 3.31-3.19 (s, 6H) |
| H-8 | | 716.85 | — |

Particularly useful as the reverse-turn mimetic in the present invention is a compound (Compound E-5) represented by

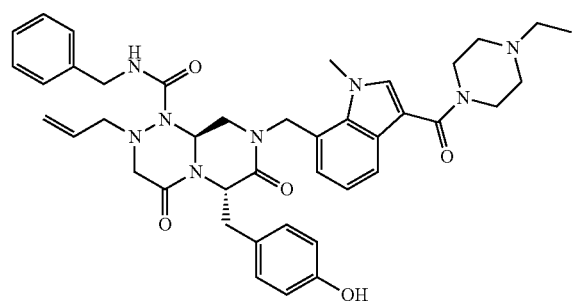

In the present invention, the pharmaceutically acceptable salt means a salt that is typically used in the medical field, and examples thereof may include metal salts of hydrochloric acid, sulfuric acid, hydrobromic acid, and phosphoric acid (e.g. sodium hydrogen ortho-phosphate and potassium hydrogen sulfate), and the salts thus listed do not limit the kinds of salt useful in the present invention. Particularly useful as the pharmaceutically acceptable salt may be a hydrochloride or sulfate.

In addition, the present invention provides a method of economically preparing the reverse-turn mimetics on a mass scale. The method of preparing the compound according to the present invention may be performed using the following procedures, but is not limited thereto.

Specifically, the method includes introducing a cyano group (—CN) to position 3 of indole-7-carbaldehyde; introducing a methyl group and an aminoacetal group (to the indole-7-carbaldehyde in which a cyano group (—CN) is introduced); performing stereoselective amidation with Cbz-tyrosine-OtBu and 2-(1-allyl-4-benzylsemicarbazido)acetic acid (for the indole-7-carbaldehyde in which a cyano group (—CN), a methyl group and an aminoacetal group are introduced); performing cyclization using formic acid (for the amidated compound); and converting the cyano group (—CN) of the resulting compound into a carboxyl group and then performing amidation.

Also, the method of preparing the compound according to the present invention may be performed using the following procedures, but is not limited thereto.

Specifically, the method includes iodizing indole-7-carbaldehyde so that iodine is introduced to position 3 of indole-7-carbaldehyde; introducing a methyl group and an aminoacetal group (to the indole-7-carbaldehyde in which a iodine is introduced); performing stereoselective amidation with Cbz-tyrosine-OtBu and 2-(1-allyl-4-benzylsemicarbazido)acetic acid (for the indole-7-carbaldehyde in which a iodine, a methyl group and an aminoacetal group are introduced); performing cyclization using formic acid (for the amidated compound); and subjecting the resulting compound to Suzuki reaction using an aryl boric acid derivative and a palladium catalyst.

In the above preparation method, 2-(1-allyl-4-benzylsemicarbazido)acetic acid may be prepared as follows: introducing triethylamine (TEA) to an ethylhydrazinoacetate solution; adding allyl bromide dropwise to the solution (in which TEA is added); and adding benzylisocyanate dropwise to the solution (solution in which TEA and allyl bromide are added).

The schematic preparation schemes of representative compounds among the compounds of the present invention are illustrated below, but are not limited thereto.

[Preparation Scheme 1]

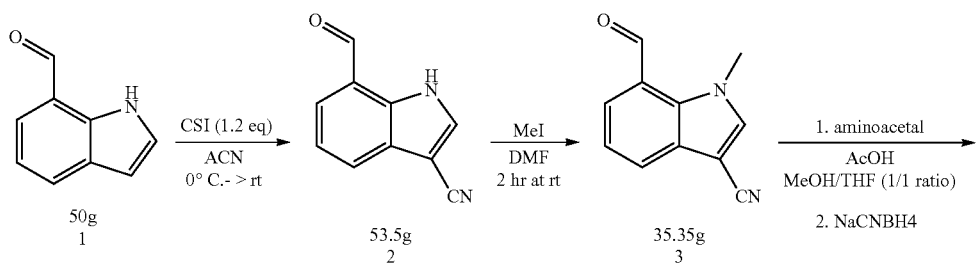

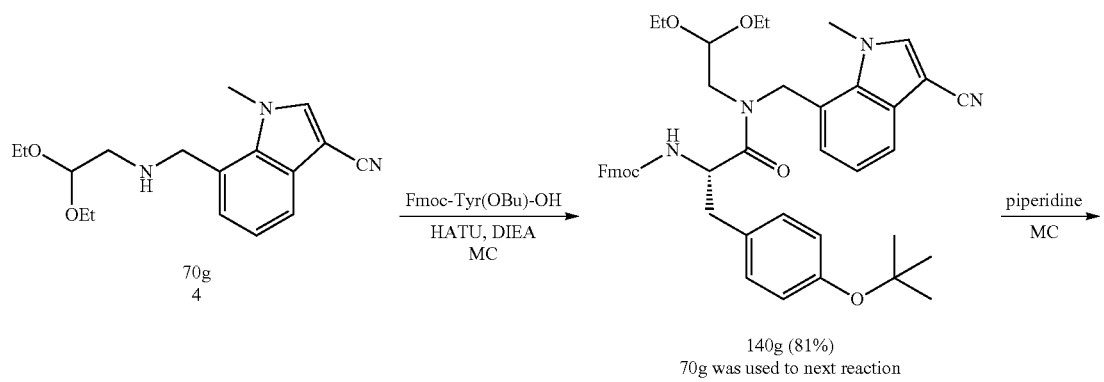

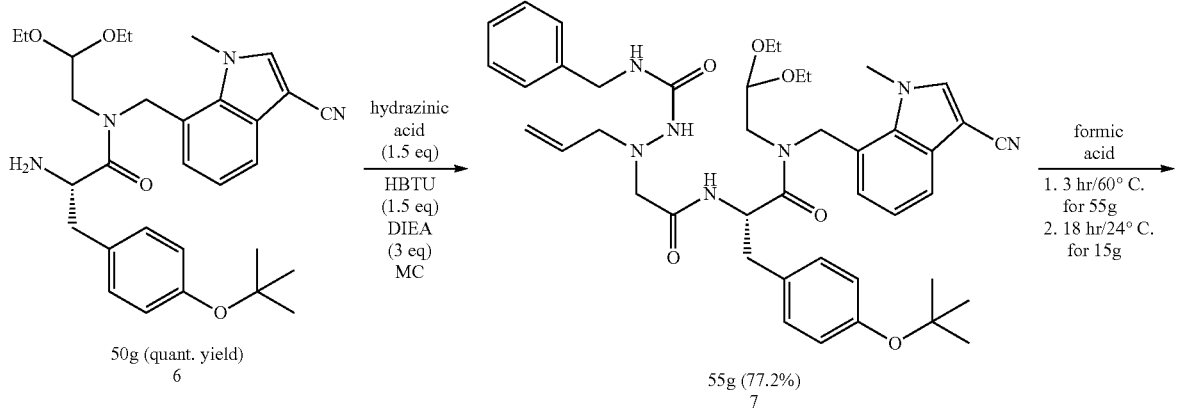

-continued
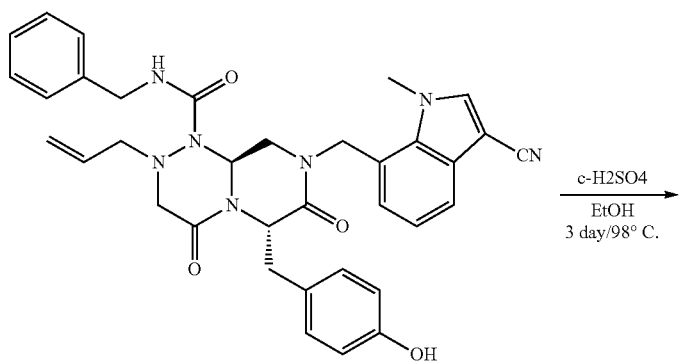
pure: 14.8g (33.3%)
8
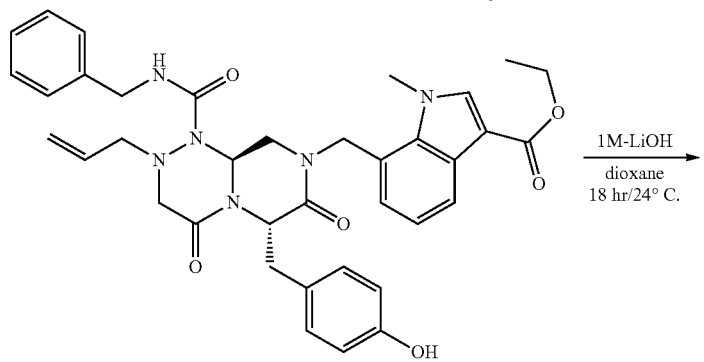
pure: 7.2g (45.2%)
9
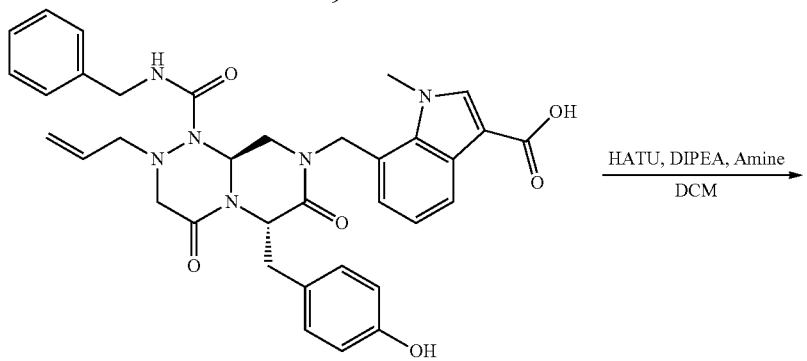
6.4g (78.5%)
10
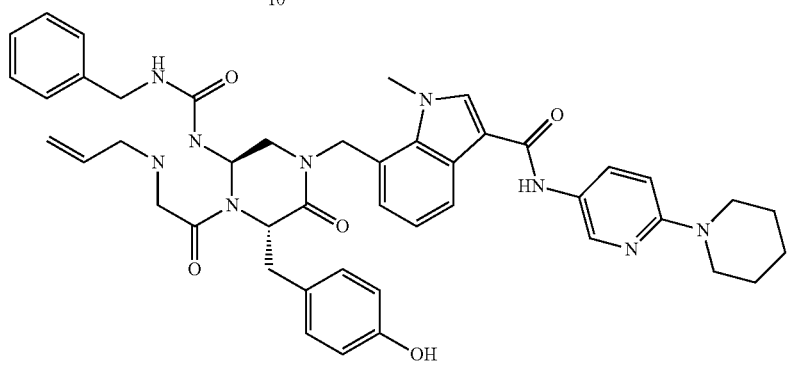
A

[Preparation Scheme 2]
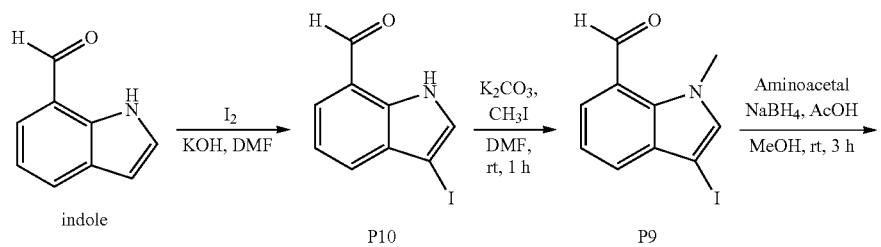
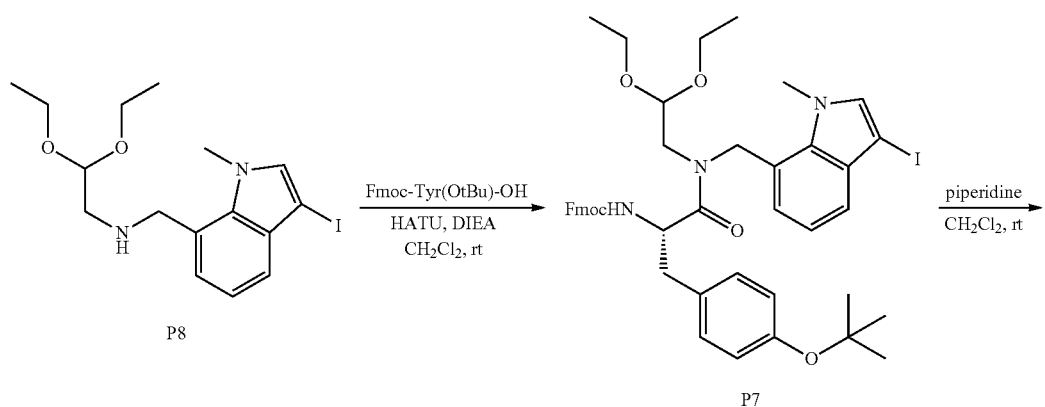
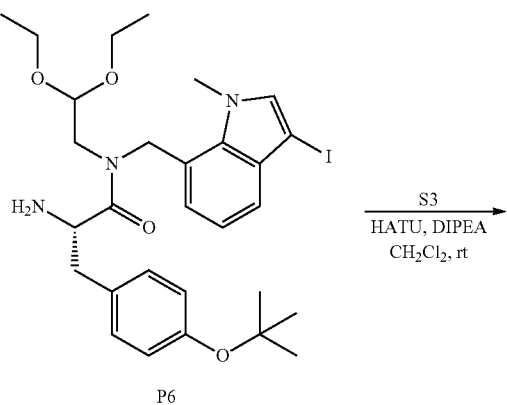
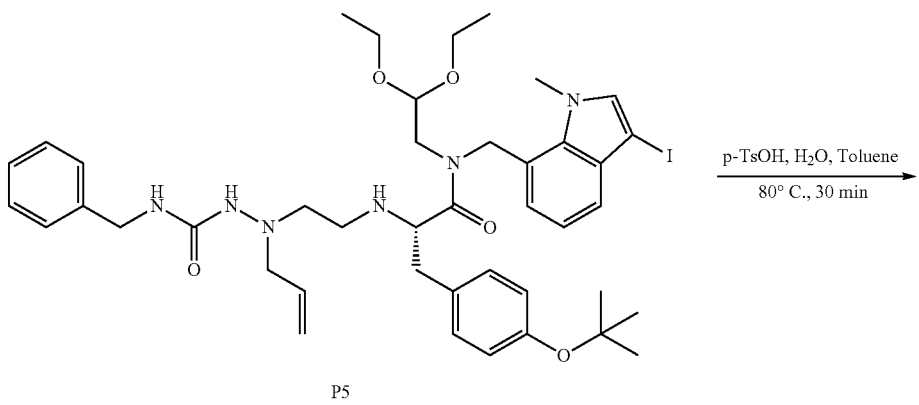

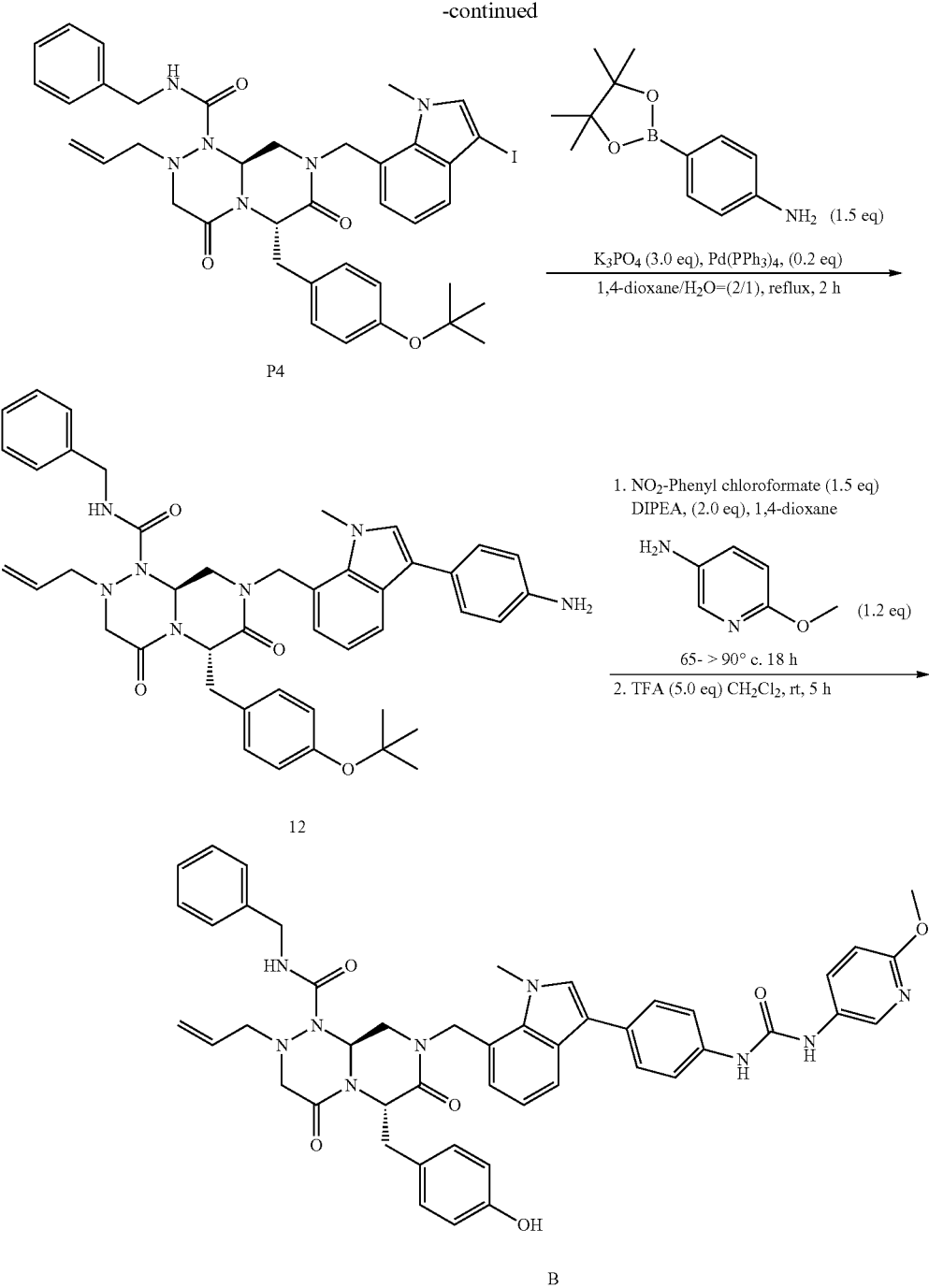
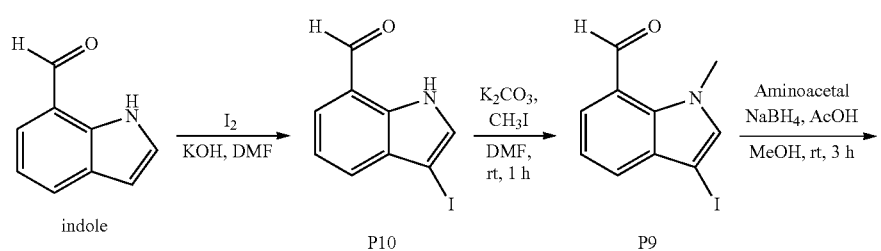
[Preparation Scheme 3]

-continued
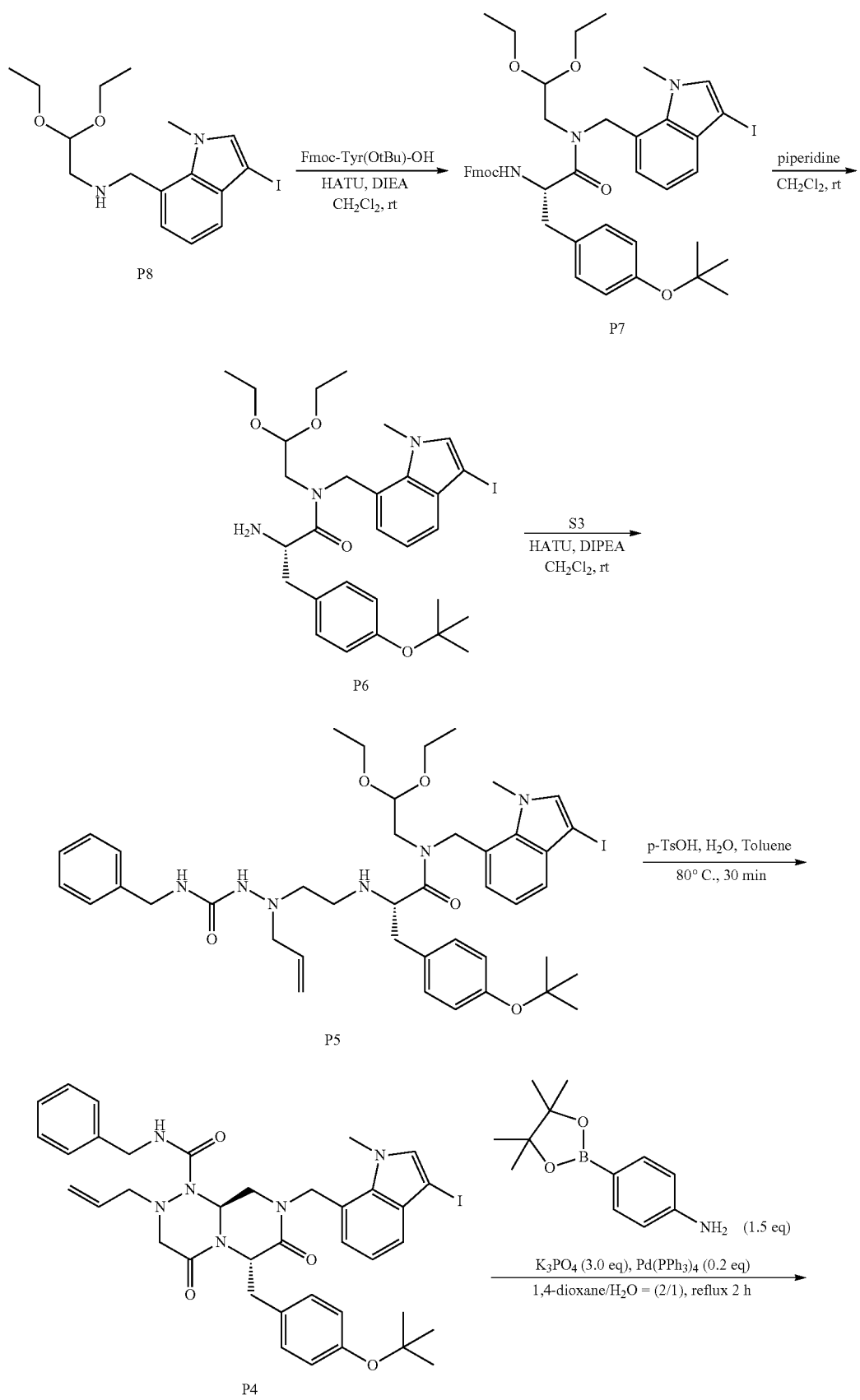

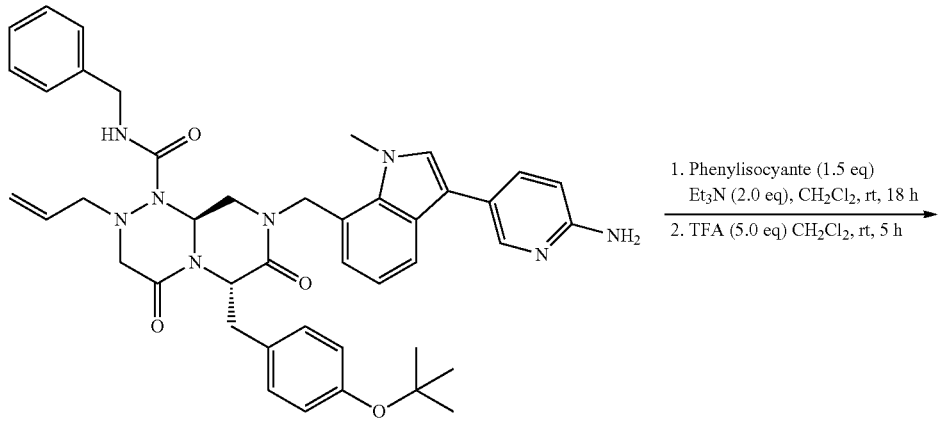

14

1. Phenylisocyante (1.5 eq)
   Et₃N (2.0 eq), CH₂Cl₂, rt, 18 h
2. TFA (5.0 eq) CH₂Cl₂, rt, 5 h

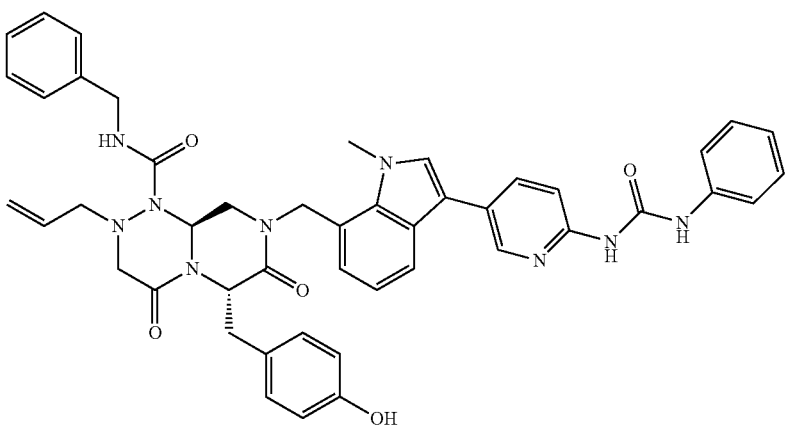

C

In Preparation Scheme 2 or 3, S3 is a compound having a structure of

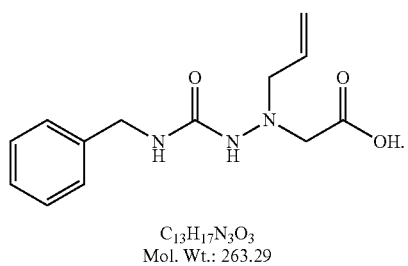 [SMILES: C=CCN(CC(=O)O)NC(=O)NCc1ccccc1]

$C_{13}H_{17}N_3O_3$
Mol. Wt.: 263.29

The structure of the compound of the present invention has different functional groups at four portions of pyrazino-triazinone used as a basic framework, and also has two chiralities and thus should be stereoselectively synthesized.

In Preparation Scheme 1, the compound of the present invention may be produced by introducing carboxylic acid to position 3 of the indole of indol-7-aldehyde used as a starting material, thus obtaining an intermediate compound, which is then coupled with a variety of amines.

In Preparation Scheme 2 or 3, the compound of the present invention may be produced by introducing iodine to position 3 of the indole of indol-7-aldehyde used as a starting material, thus obtaining an intermediate compound, to which an aryl carboxyl group and an aryl amine group are then introduced using a Suzuki reaction, followed by performing a coupling reaction.

Also, the compound of the present invention may be prepared in the following Preparation Schemes 4 to 8 below, but the present invention is not limited thereto.

[Preparation Scheme 4]
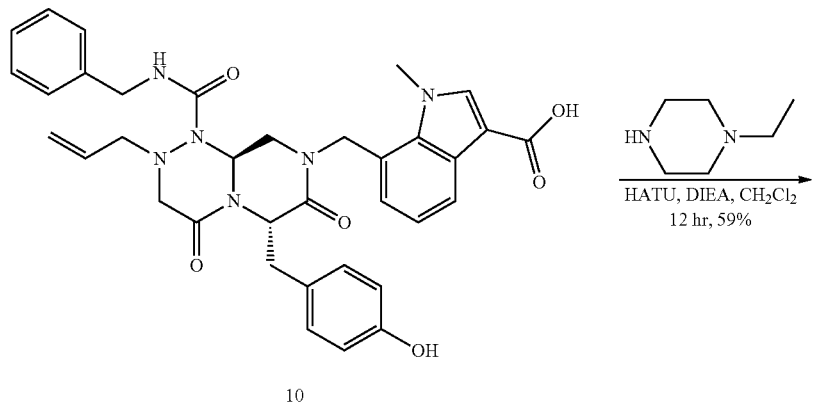
Compound 10 (indole acid) of Preparation Scheme 1 is coupled with substituted piperazine, thus synthesizing Compound E-5.
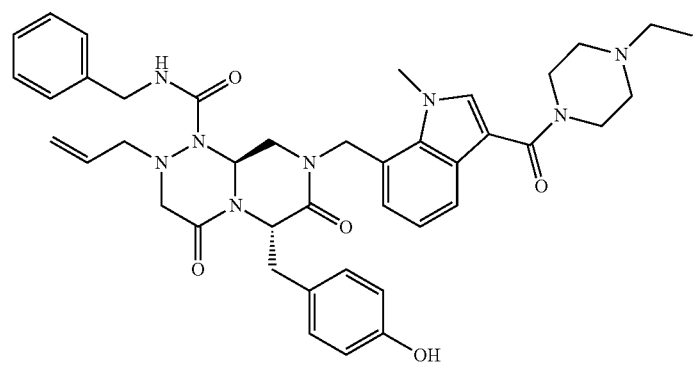
[Preparation Scheme 5]
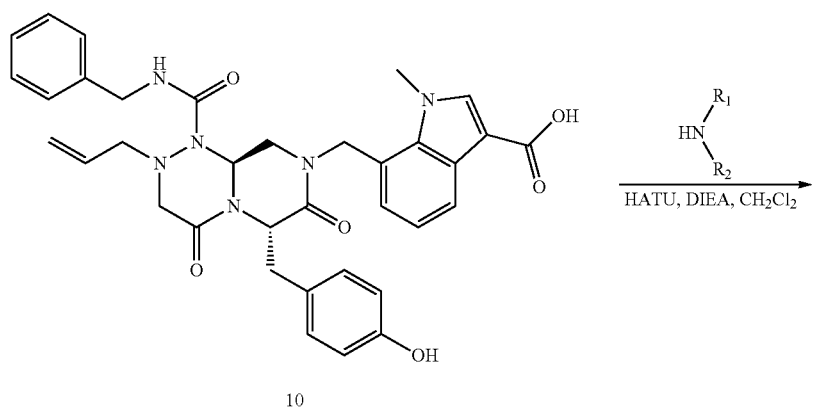

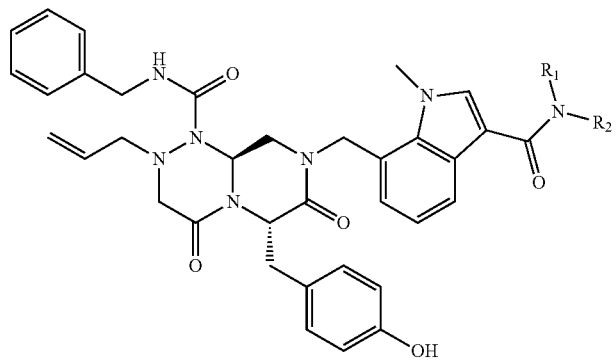
E1
The indole acid intermediate, Compound 10, prepared in the method as in Preparation Scheme 1 may be coupled with amine (NHR₁R₂), thus preparing a pyrazino-triazine derivative E1.
[Preparation Scheme 6]
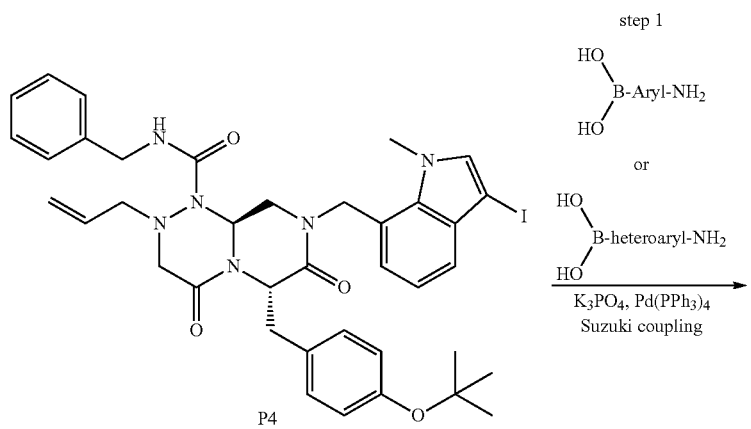
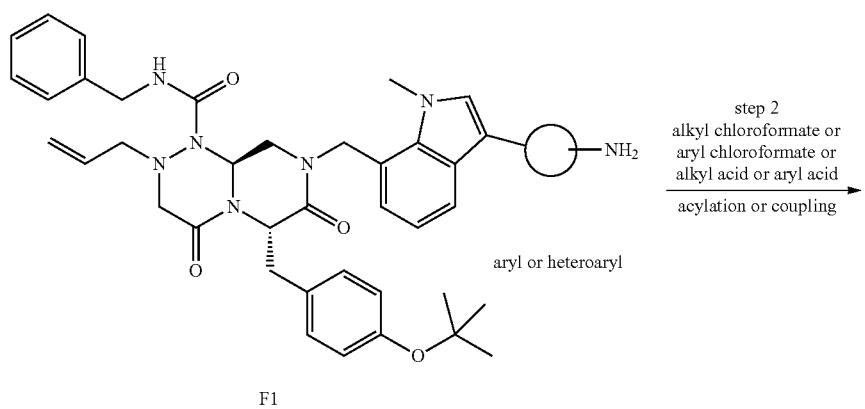

-continued

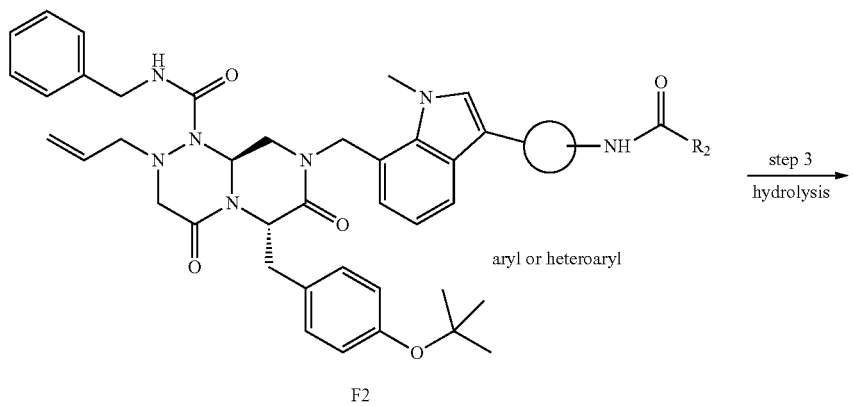

F2 aryl or heteroaryl step 3
hydrolysis →

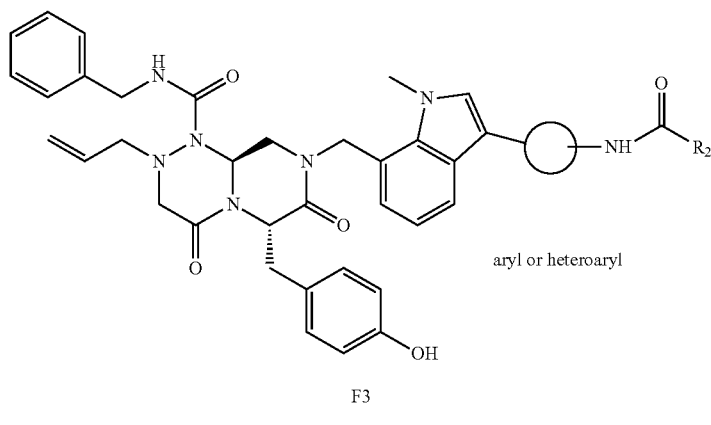

F3 aryl or heteroaryl

Respective steps of Preparation Scheme 6 are as follows:
Step 1: Suzuki coupling an indole intermediate P4 obtained in the method as in Preparation Scheme 2;

Step 2: acylating the compound F 1 resulting from Suzuki coupling thus producing an acyl compound; and
Step 3: deprotecting the acyl compound F2.

[Preparation Scheme 7]

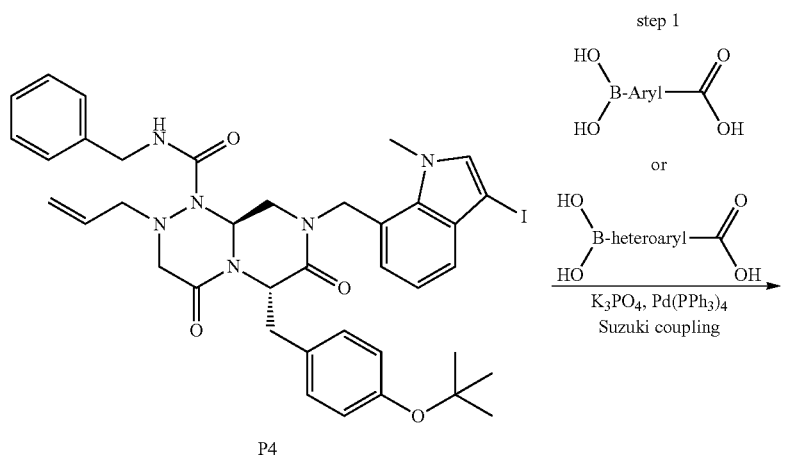

P4

$K_3PO_4$, $Pd(PPh_3)_4$
Suzuki coupling

-continued
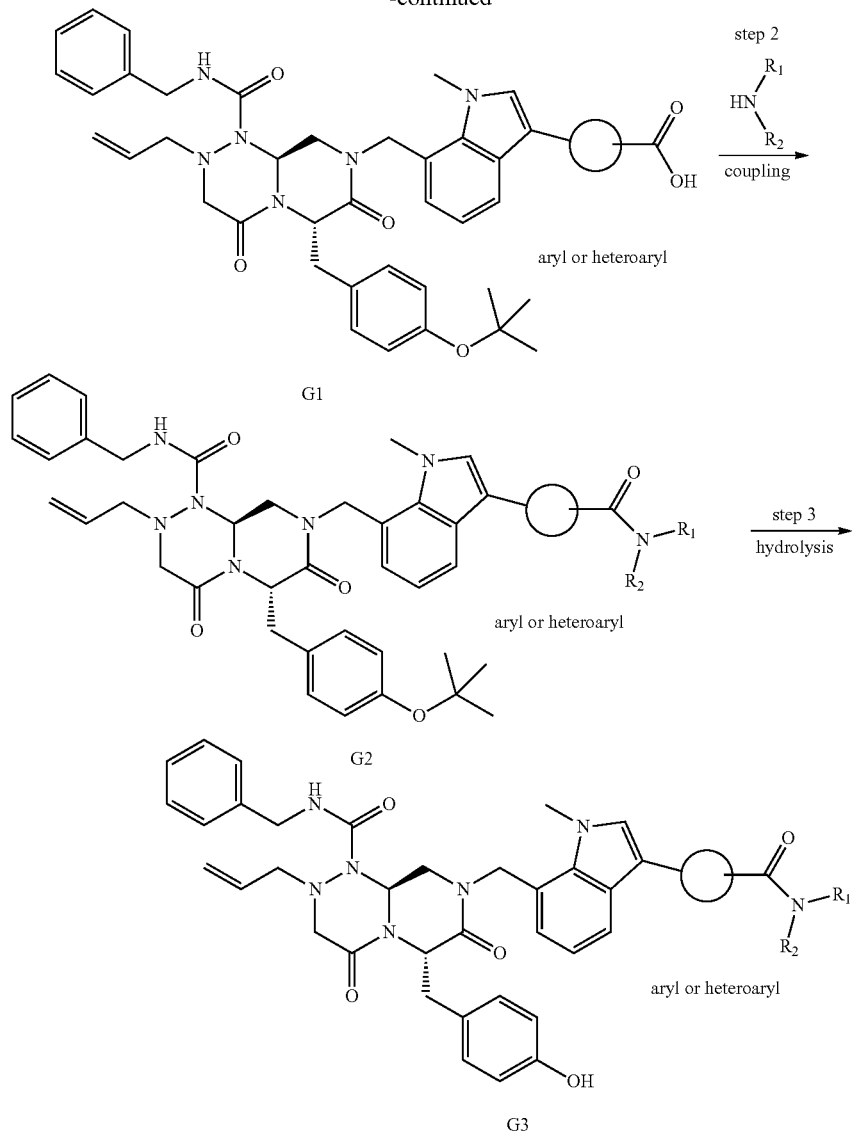
Respective steps of Preparation Scheme 7 are as follows:
Step 1: Suzuki coupling an indole intermediate P4 obtained in the method as in Preparation Scheme 2;
Step 2: coupling the compound G1 resulting from Suzuki coupling with substituted amine; and
Step 3: deprotecting the amide compound G2.
[Preparation Scheme 8]
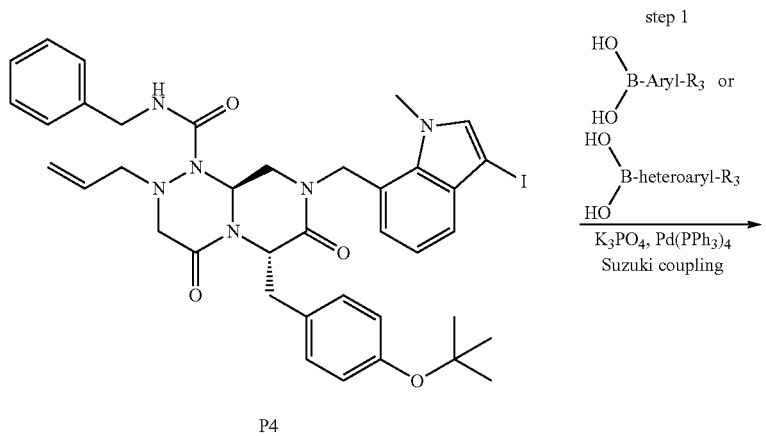

-continued

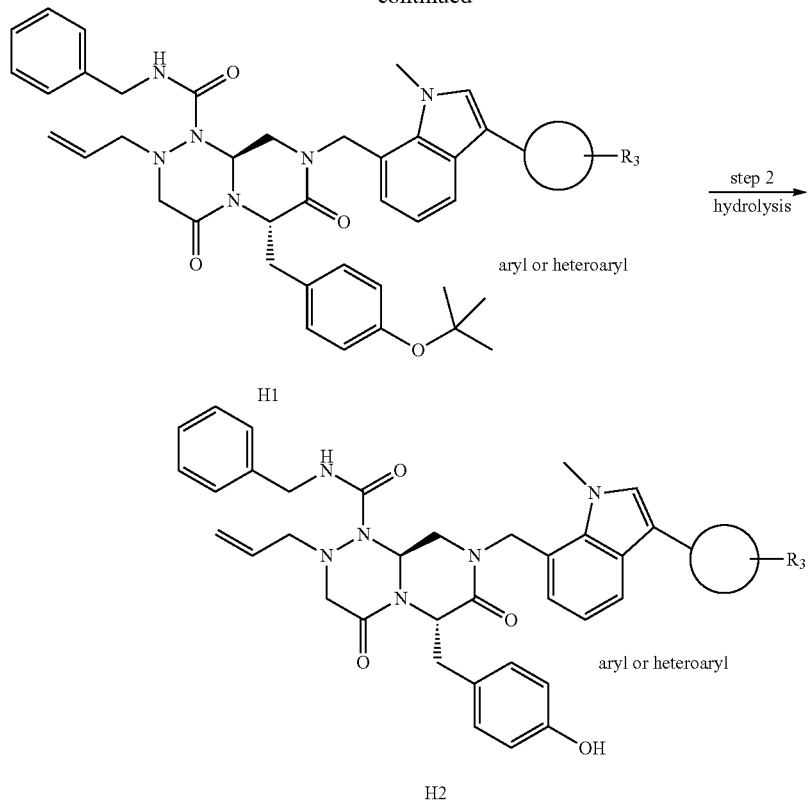

Respective steps of Preparation Scheme 8 are as follows:
Step 1: Suzuki coupling an indole intermediate P4 obtained in the method as in Preparation Scheme 2; and
Step 2: deprotecting the compound H1 resulting from Suzuki coupling.

A pharmaceutical composition containing the compound represented by Formula I according to the present invention can be used to treat cancer, in particular, acute myeloid leukemia.

Also, an injection composition containing the compound represented by Formula I according to the present invention can be used to treat cancer, in particular, acute myeloid leukemia.

The following examples, which are set forth to illustrate but are not to be construed as limiting the present invention, may improve the understanding of the present invention.

Specific illustrations of the method of preparing the compounds according to the present invention are described below.

EXAMPLE

Example 1

Preparation of Compound A

Compound A according to the present invention was prepared by Preparation Scheme 1.

(1) Synthesis of Compound 2
(7-formyl-1H-indole-3-carbonitrile)

50 g of Compound 1 was dissolved in 1 l of acetonitrile and this solution was cooled to 5° C., and 36 ml (1.2 eq) of chlorosulfonylisocyanate was added dropwise. The temperature was raised to room temperature (25° C.) and the mixture was stirred for 2 hours. An excess of DMF was added, and the resulting mixture was stirred for 1 hour, after which the reaction was terminated with an excess of water, followed by performing layer separation with ethylacetate (EA), dehydrating with $MgSO_4$, filtering and concentrating under reduced pressure, yielding 53.5 g (91.3%) of the title compound (Compound 2).
1H NMR (300 MHz, DMSO-d6, ppm, δ) 12.58(bs, 1H), 10.20(s, 1H), 8.31(d, J=3.1 Hz, 1H), 8.03(d, J=7.94 Hz, 1H), 7.97(dd, J=7.72, J=1.13 Hz, 1H), 7.49(t, 7.94 Hz, 1H)

(2) Synthesis of Compound 3 (7-formyl-1-methyl-1H-indole-3-carbonitrile)

53.4 g of Compound 2 was dissolved in 600 ml of DMF, and 215 g (5 eq) of $K_2CO_3$ and 58 ml (3 eq) of $CH_3I$ were added, and the resulting mixture was stirred at room temperature for 15 hours. The termination of the reaction was confirmed, followed by performing layer separation using $H_2O$ and EA, dehydrating using $MgSO_4$, and filtering and drying under reduced pressure. The produced solid was treated with hexane for 30 minutes thus preparing a slurry which was then filtered and dried, yielding 35.4 g (61.2%) of the title compound (Compound 3).
1H NMR (300 MHz, DMSO-d6, ppm, δ): 10.42(s, 1H), 8.38(s, 1H), 7.98(d, J=8.07, 1H), 7.95(dd, J=7.55, 1.12, 1H), 7.46(d, J=7.62, 1H), 4.15(S, 3H)

(3) Synthesis of Compound 4 (7-(((2,2-diethoxyethyl)amino)methyl)-1-methyl-1H-indole-3-carbonitrile)

49 g of Compound 3 was suspended in a solvent mixture of $CH_3OH$ (1 l) and THF (1 l), and 42.4 ml (1.1 eq) of diethyl aminoacetal and 22.8 ml (1.5 eq) of acetic acid were added at room temperature, and the mixture was warmed to 50° C. so that undissolved Compound 3 was completely dissolved, and then the mixture was stirred at room temperature for 1 hour. 18.4 g (1.1 eq) of NaCNBH$_4$ was added at room temperature and the mixture was stirred for 1 hour, followed by performing layer separation using H$_2$O and EA, dehydrating with MgSO$_4$, filtering and drying under reduced pressure, thus obtaining a crude title compound. This crude title compound was purified using column chromatography, yielding 70 g (87.3%) of the title compound (Compound 4).

1H NMR(300 MHz, DMSO-d6, ppm, δ): 9.37(bs, 1H), 8.28(s, 1H), 7.69(d, J=7.58, 1H), 7.49(bs, 1H), 7.31(t, J=8.05, 1H), 4.90(bs, 1H), 4.63(bs, 2H), 4.15(s, 3H), 3.60 (m, 4H), 3.15(bs, 2H), 1.15(t, J=6.98, 6H)

(4) Synthesis of Compound 5 ((S)-(9H-fluoren-9-yl) methyl (3-(4-(tert-butoxy)phenyl)-1-(((3-cyano-1-methyl-1H-indol-7-yl)methyl)(2,2-diethoxyethyl) amino)-1-oxopropan-2-yl)carbamate)

70 g of Compound 4 and 106.8 g (1.0 eq) of Fmoc-Tyr(OtBu)OH were dissolved in 2 l of DCM (dichloromethane), and 106 g (1.2 eq) of HATU (O-(7-azabenzotriazol-1-yl)-N,N,N',N'-tetramethyluronium hexafluorophosphate) and 97 ml (2.4 eq) of DIPEA (Diisopropylethylamine) were added at room temperature. The mixture was stirred at room temperature for 3 hours, followed by performing layer separation using H$_2$O and DCM, dehydrating with MgSO$_4$, filtering and drying under reduced pressure, thus obtaining a crude title compound. This crude title compound was purified using column chromatography, yielding 140 g (81%) of the title compound (Compound 5).

1H NMR (300 MHz, CDCl$_3$, ppm, δ): 7.75(d, J=7.31, 2H), 7.70~7.48(m, 3H), 7.47~7.36(m, 3H), 7.30(t, J=7.75, 2H), 7.21~7.05(m, 2H), 6.98~6.66(m, 4H), 5.58~5.32(m, 1H), 5.14~4.87(m, 1H), 4.73~4.61(m, 1H), 4.44~4.05(m, 5H), 3.95(d, J=18.76, 2H), 3.79~3.64(m, 1H), 3.61~3.40(m, 3H), 3.38~3.16(m, 2H), 3.15~2.85(m, 3H), 1.28(m, 9H), 1.10(m, 61~1)

(5) Synthesis of Compound 6 ((S)-2-amino-3-(4-(tert-butoxy)phenyl)-N-((3-cyano-1-methyl-1H-indol-7-yl)methyl)-N-(2,2-diethoxyethyl)propanamide)

70 g of Compound 5 was dissolved in 700 ml of DCM, and 70 ml of piperazine was added at room temperature. The mixture was stirred at room temperature for 2 hours, and H$_2$O was added to separate layers, after which DCM and piperazine were removed under reduced pressure. The resulting crude compound was purified using column chromatography, yielding 50 g (quant. yield) of the title compound (Compound 6).

1H NMR (300 MHz, DMSO-d6, ppm, δ): 8.17(s, 1H), 7.50(d, J=7.89, 1H), 7.14(m, 2H), 6.99(d, J=8.35, 1H), 6.83 (m, 3H), 5.13(m, 2H), 4.53(t, J=4.91, 0.5H), 4.33(t, J=5.34, 0.5H), 4.04(m, 4H), 3.5~3.15(m, 10H), 1.26(s, 9H), 1.02(m, 6H)

(6) Synthesis of Compound 7 ((S)-2-allyl-N-benzyl-2-(2-((3-(4-(tert-butoxy)phenyl)-1-(((3-cyano-1-methyl-1H-indol-7-yl)methyl)(2,2-diethoxyethyl) amino)-1-oxopropan-2-yl)amino)-2-oxoethyl) hydrazinecarboxamide)

49 g of Compound 6, 33.9 g (1.2 eq) of hydrazine acid and 53.5 g (1.5 eq) of HBTU (O-Benzotriazole-N,N,N',N'-tetramethyl-uronium-hexafluoro-phosphate) were dissolved in 1 l of DCM, and 49.2 ml (3 eq) of DIPEA (diisopropylethylamine) was added at room temperature. The mixture was stirred at room temperature for 15 hours, after which the termination of the reaction was confirmed, followed by conducting layer separation with H$_2$O, dehydrating with MgSO$_4$, filtering and drying under reduced pressure. The resulting crude compound was purified using column chromatography, yielding 55 g (77.2%) of the title compound (Compound 7).

1H NMR (300 MHz, DMSO-d6, ppm, δ): 8.64(m, 1H), 8.16(m, 2H), 7.50(d, J=7.22, 1H), 7.35~7.05(m, 9H), 6.86~6.60(m, 3H), 5.84(m, 1H), 5.28~5.03(m, 4H), 4.80~4.10(m, 2H), 4.03(s, 3H), 3.61(m, 4H), 3.5~2.8(m, 10H), 1.25(m, 9H), 1.05(m, 6H)

(7) Synthesis of Compound 8 ((6S,9aS)-2-allyl-N-benzyl-8-((3-cyano-1-methyl-1H-indol-7-yl)methyl)-6-(4-hydroxybenzyl)-4,7-dioxooctahydro-1H-pyrazino[2,1-c][1,2,4]-triazine-1-carboxamide)

55 g of Compound 7 was dissolved in 1 l of formic acid, and this solution was stirred at 60° C. for 2 hours. Formic acid was removed under reduced pressure, followed by conducting layer separation with H$_2$O and EA, dehydrating with MgSO$_4$, filtering and drying under reduced pressure. The resulting crude compound was purified using column chromatography, yielding 14.8 g (33.3%) of the title compound (Compound 8).

1H NMR (300 MHz, DMSO-d6, ppm, δ): 9.30(s, 1H), 8.18(s, 1H), 7.81(t, J=6.56, 1H), 7.53(d, J=7.67, 1H), 7.33~7.12(m, 6H), 6.89(d, J=8.34, 2H), 6.75(d, J=6.82, 1H), 6.62(d, J=7.80, 2H), 5.81(m, 1H), 5.40(d, J=10.74, 2H), 5.11~5.05(m, 3H), 4.90(d, J=16.09, 1H), 4.20(m, 2H), 4.07(s, 3H), 3.70(t, J=11.37, 1H), 3.61~3.55(m, 3H), 3.41~3.09(m, 3H), 3.02(dd, J=11.85, 3.48, 1H)

(8) Synthesis of Compound 9 (ethyl 7-(((6S,9aS)-2-allyl-1-(benzylcarbamoyl)-6-(4-hydroxybenzyl)-4,7-dioxohexahydro-1H-pyrazino[2,1-c][1,2,4]-triazin-8 (2H)-yl)methyl)-1-methyl-1H-indole-3-carboxylate)

14.8 g of Compound 8 was dissolved in 900 ml of ethanol (EtOH) and this solution was cooled to 5° C., and 27.23 g (14.8 d) of H$_2$SO$_4$ was added dropwise, and the mixture was stirred at 98° C. for three days and then cooled to room temperature, followed by conducting layer separation with H$_2$O and EA, dehydrating with MgSO$_4$, and filtering and drying under reduced pressure. The resulting crude compound was purified using column chromatography, yielding 7.2 g (45.2%) of the title compound (Compound 9).

1H NMR (300 MHz, DMSO-d6, ppm, δ): 9.27(s, 1H), 8.05(s, 1H), 7.96(d, J=7.69, 1H), 7.80(t, J=6.22, 1H), 7.30~7.12(m, 5H), 7.10(t, J=7.66, 1H), 6.88(d, J=8.40, 2H), 6.70(d, J=7.24, 1H), 6.62(d, J=8.38, 2H), 5.79(m, 1H), 5.43~5.37(m, 2H), 5.10~5.02(m, 3H), 4.90(d, J=15.93, 1H), 4.27~4.20(m, 4H), 4.07(s, 3H), 3.70(t, J=11.31, 1H), 3.63~3.53(m, 3H), 3.19~3.01(m, 4H), 1.32(t, J=6.88, 3H)

(9) Synthesis of Compound 10 (7-(((6S,9aS)-2-allyl-1-(benzylcarbamoyl)-6-(4-hydroxybenzyl)-4,7-dioxohexahydro-1H-pyrazino[2,1-c][1,2,4]-triazin-8 (2H)-yl)methyl)-1-methyl-1H-indole-3-carboxylic acid)

7.18 g of Compound 9 was dissolved in 540 ml of dioxane and this solution was cooled to 5° C., and 540 ml (50 eq) of 1 M LiOH was added dropwise. This mixture was stirred at room temperature for 15 hours, and dioxane was removed under reduced pressure. Ether was added to separate layers, and the aqueous layer was cooled to 5° C., and pH was adjusted to 2 using c-HCl, followed by conducting layer separation with EA, dehydrating with MgSO$_4$, and filtering and drying under reduced pressure, yielding 6.4 g (78.5%) of the title compound (Compound 10).

1H NMR (300 MHz, DMSO-d6, ppm, δ): 11.96(bs, 1H), 9.28(bs, 1H), 7.98~7.96(m, 2H), 7.80(t, J=6.56, 1H), 7.31~7.17(m, 5H), 7.07(t, J=7.64, 1H), 7.89(d, J=8.23, 2H), 6.70(d, J=7.77, 1H), 6.62(d, J=7.85, 2H), 5.79(m, 1H), 5.45~5.37(m, 2H), 5.09~5.02(m, 3H), 4.95 (d, J=16.03, 1H), 4.20~4.01(m, 5H), 3.59(t, J=11.13, 1H), 3.62~3.51(m, 4H), 3.27~2.96(m, 3H)

(10) Synthesis of Compound A ((6S,9aS)-2-allyl-N-benzyl-6-(4-hydroxybenzyl)-8-((1-methyl-3-(((6-(pyrrolidin-1-yl)pyridin-3-yl)carbamoyl)-1H-indol-7-yl)methyl)-4,7-dioxooctahydro-1H-pyrazino[2,1-c][1,2,4]-triazine-1-carboxamide)

30 mg of Compound 10 was dissolved in 10 ml of dichloromethane, and 0.02 ml (2.4 eq) of DIPEA (diisopropylethylamine) and 21 mg (1.2 eq) of HATU (O-(7-azabenzotriazol-1-yl)-N,N,N',N'-tetramethyluronium hexafluorophosphate) were added, and this mixture was stirred for 30 minutes. 9.1 mg (1.2 eq) of 6-(pyrrolidin-1-yl)pyridin-3-amine was added, and the resulting mixture was stirred at room temperature for 12 hours. The termination of the reaction was confirmed, followed by carrying out layer separation with H$_2$O, dehydrating with Na$_2$SO$_4$, and filtering and drying under reduced pressure. The resulting crude compound was purified using column chromatography, yielding 10 mg (27%) of the title compound (Compound A).

1H NMR (300 MHz, CDCl3-d, ppm, δ): 8.10~8.06(m, 3H), 8.03~7.99(m, 1H), 7.38(d, J=0.6 Hz, 1H), 7.31~7.22(m, 2H), 7.15(d, J=6.9 Hz, 2H), 7.07(t, J=7.8 Hz, 1H), 6.98(d, J=4.8 Hz, 2H), 6.86(d, J=7.2 Hz, 1H), 6.75~6.68(m, 4H), 5.61~5.52(m, 1H), 5.31~5.27(m, 2H), 5.07(d, J=10.2 Hz, 2H), 4.96~4.83(m, 1H), 4.37~4.17(m, 2H), 3.78(s, 3H), 3.49~3.22(m, 12H), 3.17~3.12 (m, 1H).

Example 2

Preparation of Compound B

Compound B according to the present invention was prepared by Preparation Scheme 2.

(1) Synthesis of S3
(2-(1-allyl-4-benzylsemicarbazido)acetic acid)

In Preparation Scheme 2, the preparation method of S3 was as follows.

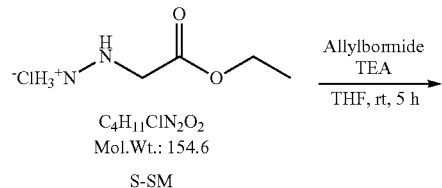

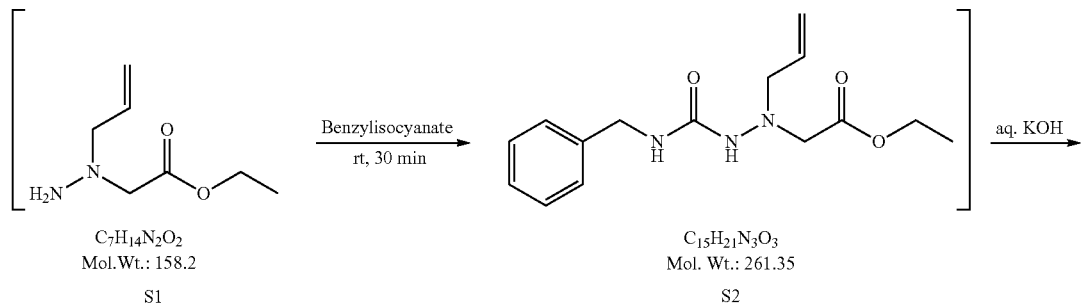

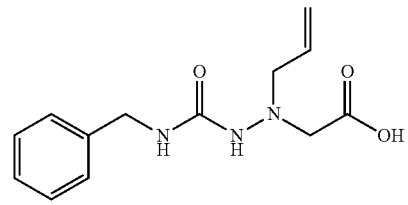

67 g of ethylhydrazinoacetate was dissolved in 673 ml of THF (tetrahydrofuran), and 121 ml of TEA (triethylamine) was added, and 41 ml of allyl bromide was added dropwise for 20 minutes. The resulting mixture was stirred for 5 hours and filtered, after which 53 ml of benzylisocyanate was added dropwise to the filtrate for 15 minutes, and the mixture was stirred at room temperature for 30 minutes. After completion of stirring, a solution of 48 g of KOH (potassium hydroxide) in 673 ml of purified water was added dropwise, and the mixture was stirred for 30 minutes. After completion of stirring, 403 ml of MC (dichloromethane) and 269 ml of hexane were added, and the mixture was stirred, and layer separation was carried out. The aqueous layer was washed once more with 201 ml and of MC. The pH of the aqueous layer was adjusted to 3 using 100 ml of c-HCl, and this solution was stirred for 30 minutes, and extracted with 1009 ml of MC. The extracted MC layer was dehydrated with 269 g of $Na_2SO_4$, filtered, and concentrated under reduced pressure. The residue thus concentrated was crystallized using 134 ml of EA (ethylacetate) and 269 ml of hexane, and filtered. The filtered solid was made into a slurry using 134 ml of EA, after which the slurry was filtered at 0, and dried in a vacuum using a vacuum oven, yielding 40 g (yield 35%) of the white solid S3.

1H NMR (500 MHz, CDCl3) δ 10.84 (bs, 1H), δ 7.90 (s, 1H), δ 7.4~7.3 (m, 5H), δ 6.42 (t, J=5.0 Hz, 1H), δ 5.85~5.72 (m, 1H), δ 5.28 (dd, J=28.5, 2.0 Hz, 1H), δ 5.19 (d, J=17 Hz, 1H), δ 4.47~4.42 (m, 2H), δ 3.70 (dd, J=40.0, 2.5 Hz, 1H).

(2) Synthesis of P10
(3-Iodo-1H-indole-7-carbaldehyde)

To a starting material (indole-7-carbaldehyde), a solution of 24 g of $I_2$ in 125 ml of DMF (dimethylformamide) was added with stirring, and 5.3 g of KOH was added, after which the mixture was allowed to react. The termination of the reaction was confirmed with thin layer chromatography (TLC), after which layer separation was conducted with 354 ml of EA and 354 ml of purified water. The organic layer was washed with aqueous 10% $Na_2S_2O_3$, dried with $Na_2SO_4$ (sodium sulfate), filtered and concentrated at 40, thus obtaining P10 as a concentrated residue.

1H-NMR (CDCl3, 300 MHz) δ 10.3 (bs, 1H), 10.2 (s, 1H), 7.79 (d, 1H, J=7.8 Hz), 7.75 (d, 1H, J=7.2 Hz), 7.44 (d, 1H, J=2.1 Hz), 7.37 (t, 1H, J=7.2 Hz); m/z 272.14 [M+1]+

(3) Synthesis of P9 (3-Iodo-1-methyl-1H-indole-7-carbaldehyde)

17 g of P10 was dissolved in 100 ml of DMF and stirred. The stirred solution was cooled to 10, and 18 g of $K_2CO_3$ (potassium carbonate) was added and 6 ml of $CH_3I$ (methyliodide) was added dropwise. The resulting mixture was warmed to room temperature and stirred for 5 hours, after which disappearance of the starting material was confirmed, and $K_2CO_3$ was filtered, followed by performing crystallization with hexane, thus obtaining P9.

$^1$H-NMR (CDCl$_3$, 300 MHz) δ 10.2 (s, 1H), 7.76 (td, 1H, J=7.8, 1.2 Hz), 7.31 (t, 1H, J=7.8 Hz), 7.12 (s, 1H), 4.14 (s, 3H)

(4) Synthesis of P8

18 g of P9 was dissolved in 600 ml of $CH_3OH$ (methanol) and 0.4 ml of acetic acid was added. 14 ml of aminoacetaldehyde diethylacetal was added at room temperature, and the mixture was stirred for 4 hours and then cooled to 10. 3.3 g of a reductant $NaCNBH_3$ (sodium cyanoborohydride) was slowly added (cautiously, because hydrogen gas and heat are generated). The resulting mixture was stirred at room temperature for 1 hour, after which the termination of the reaction was confirmed, and layer separation was conducted using 354 ml of EA and 354 ml of purified water. The organic layer was dehydrated using 141 g of $Na_2SO_4$ (sodium sulfate) and crystallized with hexane, thus obtaining P8.

(5) Synthesis of P7

27 g of Fmoc-Tyr(OtBu) was dissolved in 200 ml of MC (dichloromethane) and stirred. 23 g of HATU (O-(7-azabenzotriazol-1-yl)-N,N,N',N'-tetramethyluronium hexafluorophosphate) and 20 ml of DIPEA (diisopropylethylamine) were added dropwise at room temperature. The mixture was stirred for 2 hours, and 15.8 g of P9 was added, and the resulting mixture was stirred for 3 hours. After termination of the reaction, layer separation was carried out using purified water. The organic layer was washed with 898 ml of aqueous 5% citric acid and 898 ml of aqueous 5% $NaHCO_3$, dehydrated with $Na_2SO_4$ (sodium sulfate) and concentrated, thus obtaining P7 as a concentrated residue.

(6) Synthesis of P6

34 g of P7 was dissolved in 400 ml of MC (dichloromethane), and 20 ml of piperidine was added. The mixture was reacted and then concentrated. Layer separation was conducted with 400 ml of MC and 800 ml of purified water, and the organic layer was washed with 850 ml of aqueous 5% citric acid and 850 ml of aqueous 5% $NaHCO_3$ and concentrated, thus obtaining P6.

(7) Synthesis of P5

13 g of S3 obtained in (1) was dissolved in 400 ml of MC (dichloromethane), and 19 g of HATU (O-(7-azabenzotriazol-1-yl)-N,N,N',N'-tetramethyluronium hexafluorophosphate)) and 16 ml of DIPEA (diisopropylethylamine) were added dropwise at room temperature. The mixture was stirred for 3 hours, and a solution of 18 g of P6 in 200 ml of MC was added dropwise, and the mixture was stirred at room temperature for 2 hours. After termination of the reaction was confirmed, layer separation was conducted with 300 ml of MC and 200 ml of purified water. The organic layer was washed with 200 ml of aqueous 5% citric acid and 200 ml of aqueous 5% $NaHCO_3$, dehydrated with 340 g of $Na_2SO_4$ (Sodium sulfate) and concentrated, thus obtaining P5 as a concentrated residue.

(8) Synthesis of P4

P5 was dissolved in 100 ml of toluene, and 289 mg of p-TsOH.$H_2O$ was added, and the mixture was heated to 80. The mixture was stirred at the same temperature for 30 minutes, cooled to room temperature and concentrated. Layer separation was conducted with 200 ml of EA and 200 ml of purified water. The organic layer was washed with 200 ml of aqueous 5% citric acid and 200 ml of aqueous 5% $NaHCO_3$, dehydrated with 340 g of $Na_2SO_4$ (sodium sulfate) and concentrated, thus obtaining P4 as a concentrated residue.

1H-NMR (CDCl3, 300 MHz) δ 7.43~7.27 (m, 3H), 7.23~7.21 (m, 2H), 7.12 (t, 1H, J=7.2 Hz), 7.08 (s, 1H), 7.05 (d, 2H, J=7.8 Hz), 6.97 (d, 1H, J=7.2 Hz), 6.90 (d, 2H, J=8.4 Hz), 6.59 (t, 1H, J=6.0 Hz), 5.62 (dd, 1H, J=10.2, 4.8 Hz), 5.53~5.39 (m, 3H), 5.37 (t, 1H, J=6.0 Hz), 5.02 (d, 1H, J=10.2 Hz), 4.93 (d, 1H, J=16.5 Hz), 4.77 (d, 1H, J=17.1 Hz), 4.44

(dd, 1H, J=15.0, 6.3 Hz), 4.32 (dd, 1H, J=15.0, 6.0 Hz), 3.97 (s, 3H), 3.49~3.19 (m, 8H), 1.33 (s, 9H)

(9) Synthesis of Compound 12 (((6S,9aS)-2-allyl-8-((3-(4-aminophenyl)-1-methyl-1H-indol-7-yl)methyl)-N-benzyl-6-(4-(tert-butoxy)benzyl)-4,7-dioxooctahydro-1H-pyrazino[2,1-c][1,2,4]triazine-1-carboxamide)

1.0 g of P4 was dissolved in 20 ml of 1,4-dioxane/$H_2O$ (2/1), and 465 mg (1.5 eq) of 4-aminophenyl boronic acid pinacol ester and 872 mg (3.0 eq) of $K_3PO_4$ were added. When the temperature was gradually raised and then reached 80, 312 mg (0.2 eq) of $Pd(PPh_3)_4$ was instantly added, and the mixture was refluxed for 2 hours. The termination of the reaction was confirmed, followed by performing layer separation using $H_2O$ and EA, dehydrating with $Na_2SO_4$, and filtering and drying under reduced pressure. Subsequently, purification was conducted using NH silica gel chromatography ($CH_2Cl_2/CH_3OH$=40/1), yielding 400 mg (39%) of the title compound.

(10) Synthesis of Compound B ((6S,9aS)-2-allyl-N-benzyl-6-(4-hydroxybenzyl)-8-((3-(4-(3-(6-methoxypyridin-3-yl)ureido)phenyl)-1-methyl-1H-indol-7-yl)methyl)-4,7-dioxooctahydro-1H-pyrazino[2,1-c][1,2,4]-triazine-1-carboxamide)

30 mg of Compound 12 was dissolved in 5 ml of 1,4-dioxane, and 13 mg (1.5 eq) of 4-nitrophenyl chloroformate was added, and the mixture was stirred at 65 for 2 hours. 6.1 mg (1.2 eq) of 3-amino-6-methoxypyridine and 10 mg (2.0 eq) of DIPEA were added, and the temperature was raised to 90, and the mixture was stirred for 18 hours. The termination of the reaction was confirmed, followed by performing concentration under reduced pressure and purification using silica gel chromatography ($CH_2Cl_2/CH_3OH$=9/1), thus obtaining the title compound. This title compound was dissolved in 5 ml of $CH_2Cl_2$, and 4 mg (5.0 eq) of TFA was added, and the mixture was stirred for 5 hours. The termination of the reaction was confirmed, followed by performing concentration under reduced pressure and purification using silica gel chromatography ($CH_2Cl_2/CH_3OH$=9/1), yielding 6.8 mg (20%) of the title compound.

($CDCl_3$, 300 MHz) δ11.66 (bs, 1H), 8.43 (s, 1H), 8.28 (s, 1H), 7.77 (m, 2H), 7.64 (d, 2H, J=7.8 HZ), 7.38 (m, 2H), 7.24~7.19 (m, 2H), 7.14 (m, 1H), 7.07 (s, 1H), 7.04 (d, 2H, J=8.4 Hz), 6.90 (d, 2H, J=7.2 Hz), 6.75 (d, 2H, J=8.4 Hz), 6.70 (t, 1H, J=5.7 Hz), 5.57 (m, 1H), 5.42~5.34 (m, 3H), 5.29 (d, 1H, J=15.0 Hz), 5.18 (d, 1H, J=15.0 Hz), 5.08 (d, 1H, J=10.2 Hz), 4.90 (d, 1H, J=17.1 Hz), 4.44 (dd, 1H, J=15.0, 8.3 Hz), 4.32 (dd, 1H, J=15.0, 6.0 Hz), 3.98 (s, 3H), 3.54~3.22 (m, 9H)

Example 3

Compound C according to the present invention was prepared by Preparation Scheme 3.

(1) Synthesis of S3
(2-(1-allyl-4-benzylsemicarbazido)acetic acid)

This compound was prepared as in Example 2

(2) Synthesis of P10 to P4

These compounds were prepared as in Example 2

(3) Synthesis of Compound 14 ((6S,9aS)-2-allyl-8-((3-(6-aminopyridin-3-yl)-1-methyl-1H-indol-7-yl)methyl)-N-benzyl-6-(4-(tert-butoxy)benzyl)-4,7-dioxooctahydro-1H-pyrazino[2,1-c][1,2,4]triazine-1-carboxamide)

1.1 g of P4 was dissolved in 28 ml of 1,4-dioxane/$H_2O$ (2/1), and 516 mg (1.5 eq) of 2-aminopyridine-5-boronic acid pinacol ester and 961 mg (3.0 eq) of $K_3PO_4$ were added. When the temperature was gradually raised and then reached 80, 349 mg (0.2 eq) of $Pd(PPh_3)_4$ was instantly added and the mixture was refluxed for 2 hours. The termination of the reaction was confirmed, followed by performing layer separation using $H_2O$ and EA, dehydrating with $Na_2SO_4$, filtering and drying under reduced pressure. Subsequently, purification was carried out using NH silica gel chromatography ($CH_2Cl_2/CH_3OH$=20/1), yielding 250 mg (23%) of the title compound.

(4) Synthesis of Compound C ((6S,9aS)-2-allyl-N-benzyl-6-(4-hydroxybenzyl)-8-((1-methyl-3-(6-(3-phenylureido)pyridine-3-yl)-1H-indol-7-yl)methyl)-4,7-dioxooctahydro-1H-pyrazino[2,1-c][1,2,4]-triazine-1-carboxamide)

25 mg of Compound 14 was dissolved in 5 ml of $CH_2Cl_2$, and 6.1 mg (1.5 eq) of phenylisocyanate and 6.9 mg (2.0 eq) of $Et_3N$ were added, and the mixture was stirred at room temperature for 18 hours. The termination of the reaction was confirmed, followed by performing concentration under reduced pressure and purification using silica gel chromatography ($CH_2Cl_2/CH_3OH$=15/1), thus obtaining the title compound. This title compound was dissolved in 5 ml of $CH_2Cl_2$, and 5 mg (5.0 eq) of TFA was added. The resulting mixture was stirred for 5 hours, after which the termination of the reaction was confirmed, followed by performing concentration under reduced pressure and purification using silica gel chromatography ($CH_2Cl_2/CH_3OH$=15/1), yielding 7.5 mg (27%) of the title compound.

($CDCl_3$, 300 MHz) δ 8.01~7.87(m, 3H), 7.75 (d, 1H, J=8.1 Hz), 7.39~7.18 (m, 2H), 7.12(s, 1H), 7.08~6.99 (m, 3H), 7.04 (d, 2H, J=8.1 Hz), 6.95 (d, 2H, J=10.5 Hz), 6.83~6.71 (m, 3H) 6.76 (s, 1H), 6.73 (d, 2H, J=8.1 Hz), 5.61~5.47 (m, 3H), 5.44 (t, 1H, J=4.8 Hz), 5.39~5.25 (m, 3H), 5.03~4.97 (m, 3H), 4.83 (d, 1H, J=17.1 Hz), 4.43 (dd, 1H, J=14.7, 6.3 Hz), 4.32 (dd, 1H, J=15.6, 5.7 Hz), 3.94 (s, 3H), 3.91 (s, 3H), 3.56~3.18 (m, 9H)

Example 4

Synthesis of Compound E-5 ((6S,9aS)-2-allyl-N-benzyl-8-((3-(4-ethylpiperazine-1-carbonyl)-1-methyl-1H-indol-7-yl)methyl)-6-(4-hydroxybenzyl)-4,7-dioxooctahydro-1H-pyrazino[2,1-c][1,2,4]-triazine-1-carboxamide)

Compound 10 (15.6 g) synthesized in Example 1 was dissolved in 160 ml of dichloromethane, and 10.2 ml (2.4 eq) of DIPEA (diisopropylethylamine) and 11.1 g (1.2 eq) of HATU (O-(7-azabenzotriazol-1-yl)-N,N,N',N'-tetramethyluronium hexafluorophosphate) were added, and the resulting mixture was stirred for 30 minutes. 2.9 ml (0.95 eq) of N-ethyl piperazine was added, and the mixture was stirred at room temperature for 12 hours. The termination of the reaction was confirmed, followed by performing layer separation with $H_2O$, dehydrating with $Na_2SO_4$, filtering and drying under reduced pressure. The resulting crude compound was purified using column chromatography, yielding 10.7 g (59%) of the title compound (Compound E-5).

Example 5

Compounds shown in Tables 2 to 6 were synthesized by Preparation Schemes 4 to 8.

Test Example

The GI50, IC50, TDI, metabolic stability and PKa of Compounds A to C prepared in Examples 1 to 3 and the compounds (shown in Tables 2 to 6) prepared in Examples 4 and 5 were measured. The results are shown in Tables 7 to 10 below.

(1) Measurement of GI50 of MV-4-11

The anti-proliferative activity (cell growth inhibition assay) of the compounds according to the present invention against AML (Acute Myeloid Leukemia) cancer cells was measured. GI50 of MV-4-11 shows the anti-proliferative activity against AML cancer cells. The lower the GI50 value, the higher the anti-proliferative activity.

A cell growth Inhibition assay was performed to investigate the rate of inhibition of cell proliferation by the compounds of the present invention. MV-4-11 (human, Acute Myeloid Leukemia cell line) cells were cultured in Iscove's modified Dulbecco's medium (IMDM) including 10% fetal bovine serum (FBS), 1× penicillin/streptomycin (10,000 units/ml Penicillin, 10,000 g/ml Streptomycin in 0.85% NaCl). MV-4-11 cells were harvested with the IMDM and 5×10$^4$ cells/well were transferred to each well of 96-well culture plates (Nunc, #167008).

The compounds of Examples 1 to 5 were exposed to serial dilution and duplicated for each concentration. For the serial dilution, the compounds of the present invention were repeatedly diluted with the same volume of media onto 96-well assay block (costar, #3956). After the dilution, each compound was added to each well.

Also, the background absorbance was measured during the treatment with the test compounds by replacing the test compound with IMDM in the negative control plate. The plates were incubated for three days (72 hours) at 37 in the humidified incubator containing 5% CO$_2$. On the last day, 20 l of a CellTiter 96 Aqueous One Solution (Promega #G3581) was added to the culture in each well and the plates were incubated for a few hours at 37 in the humidified incubator containing 5% CO$_2$. After the incubation, the absorbance of each cell was measured at 490 nm using an EnVision (Perkinelmer, USA).

The GI50 values were calculated using a Prism 3.0 program. The results are shown in Tables 9 and 10 below. The results showed that the compounds of the present invention had an influence on cell proliferation and inhibited the growth of AML cancer cells.

(2) Measurement of CYP (IC50 of P450 CYP3A4)

The compounds of the present invention had lower P450 CYP3A4 inhibitory activity (higher IC50). Lower CYP3A4 inhibitory activity means that the compounds of the present invention cause fewer side-effects from the pharmacological point of view.

This assay was performed in a 200 l volume in 96-well microtiter plates using cDNA-expressed human hepatic CYP3A4 (supersome, BD Gentest™ #456202). As a substrate for CYP3A4, 7-benzyloxy-4-trifluoromethyl-coumarin (BFC) was used. The compounds of Examples 1 to 5 and the substrate BFC were dissolved in 100% acetonitrile. The final volume of acetonitrile of the incubation mixture was less than 1% (volume/volume). A potassium phosphate buffer (pH 7.4, final concentration 0.1M), MgCl$_2$ (final concentration 8.3 mM), EDTA (final concentration 1.67 mM), an inventive compound stock solution, CYP3A4 supersome, and NADPH (final concentration 0.25 mM) were added to each well. The reaction was initiated by adding the substrate (BFC, final concentration 30 M) at 37. The incubation was performed for 20 minutes and then the reaction was terminated by the addition of 75 μl of acetonitrile: 0.5 M tris-base=4:1 (volume/volume).

Then, a fluorescent signal was measured using a fluorometer. A BFC metabolite, 7-hydroxy-4-trifluoromethyl-coumarin, was measured using an excitation wavelength of 409 nm and an emission wavelength of 530 nm. The results are shown in Tables 9 and 10 below.

(3) TDI (Time Depend Inhibition)

In the same test method as measuring IC50 in (2), the reaction was initiated using Compounds A, B and C by the addition of a substrate (BFC, final concentration 30 M) after pre-incubation at 37 for 10 minutes. The incubation was conducted at 37 for 20 minutes, and the reaction was terminated with 75 μl of acetonitrile: 0.5 M tris-base=4:1 (volume/volume). Then, a fluorescent signal was measured using a fluorometer. A BFC metabolite, 7-hydroxy-4-trifluoromethyl-coumarin, was measured using an excitation wavelength of 409 nm and an emission wavelength of 530 nm. The results are shown in Table 9 below.

(4) Measurement of MLM (for Hepatic Metabolic Stability)

For the sake of retaining efficacy of novel drugs and preventing side-effects, hepatic metabolic stability is regarded as very important. Hepatic metabolic stability is typically determined using microsome or S9. In the present test, a microsome having CYP450 as a main component, which plays a great role in metabolism, was used to evaluate the metabolic stability.

This assay was performed in a 200 l volume in a 13 ml glass tube using mouse hepatic microsome whose activity was measured.

The compounds of Examples 1 to 5 were dissolved in DMSO (dimethyl sulfoxide) to prepare a 25 mM stock solution, which was then diluted with 50% acetonitrile and used in the test. A potassium phosphate buffer (pH 7.4, final concentration 0.1M), MgCl$_2$ (final concentration 0.1M), a diluted inventive compound stock solution (final concentration 1 mM), and a mouse microsome (final concentration 5 mg/ml) were added to the glass tube. The reaction was initiated by the addition of a cofactor NADPH (final concentration 12.5 mM) after pre-incubation at 37 for 3 minutes. The reaction was carried out at 37 for 10 minutes and 30 minutes, and then terminated with 1000 μl of acetonitrile, and the remaining inventive compound was extracted. The centrifugation was conducted at 3000 rpm for 10 minutes, after which the supernatant was dried and dissolved again in 150 μl of 50% acetonitrile and quantitatively analyzed by HPLC. 0 minutes and 30 minutes after reaction, the amounts of the compounds of the present invention were compared thus evaluating the extent of metabolic stability. The results are shown in Tables 9 and 10 below.

(5) Solubility

1) Evaluation of Solubility of Compounds A, B, C

The solubility of the compounds of the present invention was measured in physiological saline. When the solubility is higher, pharmacokinetic advantages are obtained in terms of administration and absorption.

Specifically, the compounds of the invention were weighed to within 0.5 mg, and saline was added to a concentration of 1 mg/ml to a 1.5 ml eppendorf tube. Sonication was conducted at 37 for 10 minutes and then centrifugation was carried out at 15000 rpm for 5 minutes. 200 µl of the solution was placed into a filter tube of a ultrafree-MC centrifugal filter unit, and centrifuged at 5000 rpm for 5 minutes and filtered. 100 µl of the filtrate was mixed with 100 µl of 100% acetonitrile, and the mixture was quantitatively analyzed by HPLC to evaluate the solubility.

2) Evaluation of Solubility of Compound E-5

Compound E-5, Compound E-5•HCl, and Compound E-5•$H_2SO_4$ were respectively weighed to 10 mg, and 0.25 ml of physiological saline was added, and they were vortex mixed. The supernatant was filtered with a 0.22 µm filter and quantitatively analyzed by HPLC. The results are shown in Table 7 below.

TABLE 7

|  | Compound E-5 | Compound E-5•HCl | Compound E-5•$H_2SO_4$ |
|---|---|---|---|
| Solubility | 0.068 mg/mL | >40 mg/mL | 0.566 mg/mL |

(6) Blood Drug Concentration Upon Administration of Compound E-5

Compound E-5 was intravenously injected in 12.5 mg/kg to SD rat. 5, 15, 30, 30, 120, 240, 1140 minutes after injection, the blood was taken and the drug concentration in the blood was quantitatively analyzed using an analyzer HPLC/MS/MS.

The results are shown in Table 8 below.

TABLE 8

|  | Compound E-5 |
|---|---|
| Dose (mg/kg) | 12.5 |
| AUC (ug hr/ml) | 4.53 |
| Half-life (t ½, hr) | 1.59 |

TABLE 9

|  | MV4-11 GI50 (nM) | CYP (µM) | TDI | MLM (%) |
|---|---|---|---|---|
| Compound A | 1.4 | 14.7 | (−) | 65% |
| Compound B | 6.5 | >25 | (−) | 65% |
| Compound C | 9.5 | >25 | (−) | 64% |

TABLE 10

| Compound No. | MV4-11 GI50(nM) | CYP (µM) | MLM (%) |
|---|---|---|---|
| D-1 | 1.8 | | |
| D-2 | 1.3 | | |
| D-3 | 0.1 | | |
| D-4 | 1.4 | | |
| D-5 | 2.2 | 1.76 | |
| D-6 | 1.7 | | |
| D-7 | 1.2 | | |
| D-8 | 1.2 | | |
| D-9 | 3.3 | | |
| D-10 | 1.3 | >25 | 88 |
| D-11 | 1.8 | 7.04 | |
| D-12 | 2.1 | >25 | |
| D-13 | 1.2 | | |
| D-14 | | 2.13 | |
| D-15 | 2.8 | 15.97 | |
| D-16 | 15.6 | 8.07 | |
| D-17 | 6.9 | 7.63 | |
| D-18 | 1.2 | 2.42 | |
| D-19 | 2 | | |
| D-20 | | 17.2 | |
| D-21 | 6.9 | 6.53 | |
| D-22 | 4.2 | 19.5 | |
| D-23 | | >25 | |
| D-25 | | >25 | |
| D-26 | 19 | 13.7 | |
| D-27 | 4.3 | | |
| D-28 | 5.5 | | |
| D-29 | 1.3 | | |
| D-30 | 1.5 | | |
| D-31 | 1.5 | >25 | 107 |
| D-32 | 1.3 | | |
| D-33 | 1.4 | | |
| D-34 | 1.2 | 3.41 | |
| D-35 | 15 | | |
| D-36 | 1.2 | | |
| D-37 | 1.3 | | |
| D-38 | 3.2 | | |
| D-39 | 1.2 | | |
| D-40 | 1.2 | | |
| D-41 | 1.2 | | |
| D-42 | 1.8 | | |
| D-43 | 1.2 | | |
| D-44 | 19.5 | >25 | |
| D-45 | 1.9 | 2.51 | 49.4 |
| D-46 | 3.4 | | |
| D-47 | 1.3 | | |
| D-48 | 1.9 | >25 | |
| D-49 | 10 | >25 | |
| D-50 | 2 | >25 | |
| D-51 | 5.4 | >25 | |
| D-52 | | 21.7 | |
| D-53 | 1.2 | | |
| D-54 | 1.2 | | |
| D-55 | 5.8 | 2.26 | |
| D-56 | 12.5 | >25 | |
| D-57 | | >25 | |
| D-59 | 1.2 | 2.19 | |
| D-60 | 1.1 | | |
| D-61 | 1.3 | | |
| D-62 | 1.3 | | |
| D-63 | 1.3 | | |
| D-64 | 1.2 | | |
| D-65 | 1.3 | | |
| D-66 | 1.3 | | |
| D-66-1 | 1.4 | | |
| D-67 | 1.3 | | |
| D-68 | 1.4 | | |
| D-69 | 1.1 | >25 | 65 |
| D-70 | 4.4 | | |
| D-71 | 1.9 | | |
| D-72 | | 2.78 | |
| D-73 | 14.4 | >25 | 73.4 |
| D-74 | 11.2 | >25 | 56.9 |
| D-75 | 17 | 10.5 | |
| D-76 | 15.8 | 9.48 | |
| D-77 | 6.5 | >25 | 65.4 |
| D-78 | 1.5 | | |
| D-79 | 10.8 | 7.8 | |
| D-81 | 9.9 | | |
| D-82 | 16.8 | 8.52 | |

TABLE 10-continued

| Compound No. | MV4-11 GI50(nM) | CYP (μM) | MLM (%) |
|---|---|---|---|
| D-83 | 13.8 | 4.61 | |
| D-84 | 1.7 | | |
| D-85 | 9.5 | >25 | 64.3 |
| D-86 | 4.9 | | |
| D-87 | 1.3 | | |
| D-88 | 1.2 | 10.2 | |
| D-89 | 1.3 | | |
| D-90 | 4.6 | 6.96 | |
| D-91 | 1.3 | 6.51 | |
| D-92 | 19 | | |
| D-93 | 16.1 | 20.39 | 68.5 |
| D-94 | 1.5 | | |
| D-96 | | 2.19 | |
| D-97 | 2.2 | 6.4 | |
| D-98 | 23 | 2.92 | |
| D-99 | 2.7 | | |
| D-101 | 5.8 | | |
| D-102 | 1.6 | 3.42 | |
| D-103 | 10.8 | | |
| D-104 | 6.3 | | |
| D-105 | 3.7 | | |
| E-1 | 5.8 | | |
| E-10 | 10.8 | 9.12 | |
| E-11 | | 11.3 | |
| E-12 | | 9.3 | |
| E-13 | | >25 | 89.1 |
| E-14 | | 10.9 | |
| E-15 | | 11.2 | |
| E-16 | | 2.82 | |
| E-17 | 4.5 | | |
| E-18 | 20.9 | | |
| E-19 | | >25 | 73.4 |
| E-21 | | >25 | |
| E-23 | | 8.17 | 73.8 |
| E-24 | | 5.53 | |
| E-25 | 20.4 | 6.09 | |
| E-26 | 2.3 | | |
| E-27 | 13.5 | | |
| E-28 | 5.6 | | |
| E-29 | 18.4 | | |
| E-30 | 14.4 | | |
| E-31 | 6 | | |
| E-33 | 9 | | |
| E-35 | 5.1 | | |
| E-36 | 8.4 | | |
| E-37 | 16.4 | | |
| E-38 | | 2.48 | |
| E-40 | 15.4 | | |
| E-42 | | 3.63 | |
| E-43 | 15.1 | 6.6 | |
| E-44 | | 15 | |
| E-45 | 1.8 | 3.98 | |
| E-46 | 2 | | |
| E-47 | 13.5 | 2.2 | |
| E-48 | | 12.1 | |
| E-49 | 6.9 | | |
| E-50 | | 5.04 | |
| E-51 | | 10.7 | |
| E-52 | 9.2 | 3.3 | |
| E-53 | 1.9 | 3.86 | |
| E-54 | | 4.97 | |
| E-56 | 3.1 | | |
| E-57 | | 7.65 | |
| E-59 | | >25 | 58.5 |
| E-60 | | 6.02 | |
| E-61 | | 2.23 | |
| E-64 | | 8.55 | |
| E-65 | 13 | 2.11 | |
| E-68 | | 2.45 | |
| E-69 | | 4.49 | |
| E-70 | | 18.3 | |
| E-71 | | >25 | 67.2 |
| E-72 | | 5.99 | |
| E-73 | 19.3 | 11.8 | |
| E-3 | 18.4 | 3.9 | |
| E-4 | 11.2 | 12.2 | |
| E-5 | 11.6 | 8.04 | |
| E-7 | 11.3 | 2.24 | |
| E-8 | 8.9 | | |
| E-9 | | 6.82 | |
| F-1 | | 3.16 | |
| F-3 | 7.6 | 2.51 | |
| F-4 | | 16.18 | |
| F-5 | 16 | 3.68 | |
| F-6 | 11.9 | 3.84 | |
| F-7 | | 16.36 | |
| F-8 | 2 | | |
| F-9 | 15.4 | 2.53 | |
| F-10 | 15.1 | 2.01 | |
| F-11 | 10.4 | | |
| F-13 | | 7.87 | |
| F-14 | | 3.64 | |
| F-18 | | 17.89 | |
| F-19 | 1.5 | | |
| F-20 | | 2.89 | |
| F-21 | | 10.89 | |
| F-22 | | 3.58 | |
| F-23 | | 3.46 | |
| F-24 | | >25 | 84.2 |
| F-25 | | 8.5 | |
| F-26 | 19.8 | 2.86 | |
| F-27 | | 11.51 | |
| F-28 | | 7.8 | |
| F-29 | | 1.1 | |
| F-30 | | 2.54 | |
| F-31 | 1.9 | | |
| F-32 | | 5.04 | |
| F-36 | | 2.48 | |
| F-38 | 6.1 | | |
| F-40 | 17.2 | | |
| F-41 | 11.6 | | |
| F-42 | 9.1 | | |
| F-43 | 17.8 | | |
| F-44 | 4.5 | | |
| F-45 | 1.7 | | |
| F-46 | 1.3 | | |
| F-47 | 6.9 | 2.05 | |
| F-48 | 10.7 | 2.18 | |
| F-49 | 11.4 | | |
| F-50 | 1.6 | | |
| F-52 | 4.6 | | |
| F-53 | | 2.33 | |
| F-55 | | 6.15 | |
| F-56 | | 17.44 | |
| F-57 | | 4.78 | |
| F-58 | | 22.29 | |
| F-59 | | 2.39 | |
| F-60 | | 6.8 | |
| F-61 | 1.6 | 5.65 | |
| F-63 | | 9.71 | |
| F-64 | | 5.12 | |
| F-65 | | 6.87 | |
| F-66 | 17.5 | 6.15 | |
| F-67 | 2.5 | 9.65 | |
| G-1 | | 2.97 | |
| G-2 | 8 | | |
| G-3 | 5.7 | 2.61 | |
| G-5 | 8.8 | 2.16 | |
| G-6 | 14 | 19.1 | |
| G-7 | 10.5 | | |
| G-8 | 7.4 | | |
| G-9 | 19.9 | | |
| G-10 | 1.7 | 7.4 | |
| G-11 | 1.8 | 7.62 | |
| G-12 | 9.9 | 10.1 | |
| G-13 | 9 | 13.03 | |
| G-14 | 1.2 | | |
| G-15 | 1.2 | 6.75 | |
| G-16 | 1.7 | | |
| G-17 | 2 | | |
| G-18 | 1.5 | 3.45 | |
| G-19 | 9.3 | | |
| G-20 | 1.7 | | |
| G-21 | | 2.55 | |

TABLE 10-continued

| Compound No. | MV4-11 GI50(nM) | CYP (µM) | MLM (%) |
|---|---|---|---|
| G-22 | 1.4 | 2.38 | |
| G-23 | 1.3 | 6.75 | |
| G-24 | | 4.53 | |
| G-25 | | 4.05 | |
| G-26 | | 5.35 | |
| G-27 | 2 | 2.53 | |
| G-28 | 5.6 | 2.32 | |
| G-29 | | 5.8 | |
| G-30 | 5 | | |
| G-31 | 2.7 | 7.67 | |
| G-32 | 11.9 | 2.57 | |
| G-34 | 1.37. | | |
| G-35 | 1.4 | 12.24 | 34.9 |
| G-36 | 1.3 | 21.06 | 36 |
| G-37 | 1.3 | 6.95 | |
| G-38 | 0.6 | 2.21 | |
| G-39 | 11.3 | 2.73 | |
| G-40 | 1.3 | | |
| G-41 | 1.3 | 7.6 | |
| G-42 | 1.3 | 5.73 | |
| G-43 | 1.3 | 6.94 | |
| G-44 | 1.3 | 6.04 | |
| G-45 | 1.2 | | |
| G-46 | 1.3 | 6.12 | |
| G-47 | 2.3 | 3.67 | |
| G-48 | 1.3 | 4.19 | |
| G-49 | 1.3 | 6.94 | |
| G-50 | 2.4 | 17.24 | |
| G-51 | 1.3 | 3.97 | |
| G-52 | 13 | 7.1 | |
| G-53 | 1.3 | >25 | |
| G-54 | 1.4 | 3.29 | |
| G-55 | 1.3 | 2.37 | |
| G-56 | 1.3 | | |
| G-57 | 1.3 | 6.32 | |
| G-58 | | 23.67 | 85.1 |
| G-59 | 4.9 | >25 | 61.9 |
| G-60 | 6.5 | 21.52 | 52.8 |
| G-61 | 8.5 | 4.87 | |
| G-62 | 1.4 | 4.1 | |
| G-63 | 1.5 | 2.56 | |
| G-64 | 1.3 | 7.64 | |
| G-65 | 1.3 | 3.91 | |
| G-66 | 1.3 | 4.6 | |
| G-67 | 1.3 | 11.24 | |
| G-68 | 2.2 | 6.4 | |
| G-70 | 1.7 | 2.63 | |
| H-1 | 15 | 3.85 | |
| H-2 | 17.8 | 9.33 | |
| H-3 | 2.2 | 10 | |
| H-4 | 15 | >25 | 66.8 |
| H-5 | | >25 | 74 |
| H-6 | 9.7 | 2.09 | |
| H-7 | 1.5 | 6.41 | |
| H-8 | 5.7 | | |

As is apparent from Tables 9 and 10, the compounds of the present invention exhibit GI50 on the level of nM, which means that the compounds of the invention have high inhibitory activity for AML cancer cells.

Also as is apparent from Tables 9 and 10, the compounds of the present invention show low CYP3A4 inhibitory activity (higher IC50). Lower CYP3A4 inhibitory activity means that the compounds of the present invention cause fewer side-effects from the pharmacological point of view.

Furthermore, the compounds of the present invention have increased hepatic metabolic stability superior to that of conventional compounds of reverse-turn mimetics. Upon injection in vivo, the compounds of the present invention can exhibit equal or superior efficacy even when they are administered in a smaller dose or they are injected at a lower frequency.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The novel compounds of the present invention can effectively inhibit the proliferation of acute myeloid leukemia cancer cells in vitro, and also efficiently suppresses the growth of tumor in acute myeloid leukemia mouse model. Furthermore, the compounds of the present invention exhibit low CYP3A4 inhibitory activity, and superior hepatic metabolic stability.

What is claimed is:

1. A compound represented by Formula I below or a pharmaceutically acceptable salt thereof:

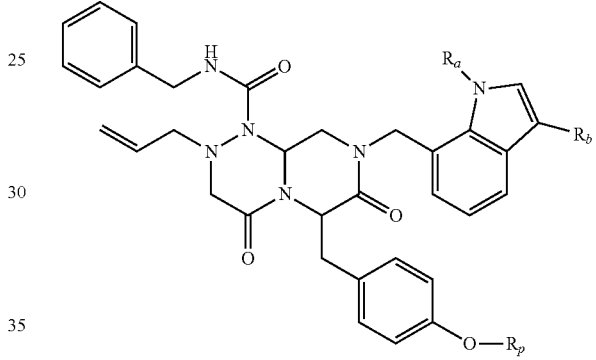

[Formula I]

wherein $R_a$ is $C_1$-$C_6$ alkyl group, $C_2$-$C_6$ alkenyl group, or $C_2$-$C_6$ alkynyl group;

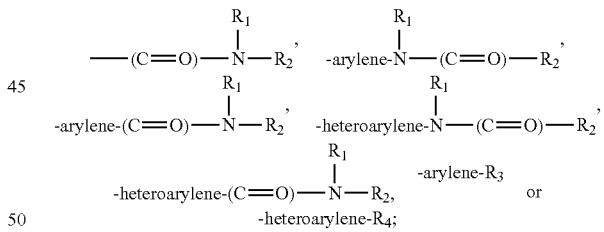

wherein $R_1$ is H, $C_1$-$C_{12}$ alkyl group or substituted $C_1$-$C_{12}$ alkyl group;

$R_2$ is H, $C_1$-$C_{30}$ alkyl group, $C_3$-$C_{10}$ cycloalkyl group, amino group, $C_1$-$C_{30}$ alkoxy group, benzyl group,

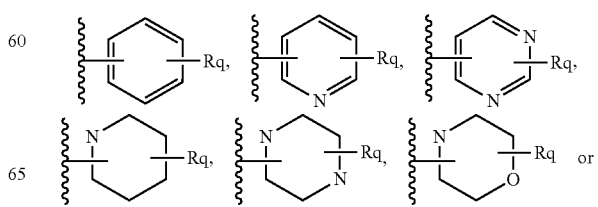

-continued

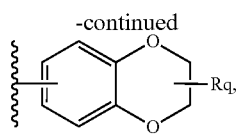

and wherein the $C_1$-$C_{30}$ alkyl group, the $C_3$-$C_{10}$ cycloalkyl group, the amino group, the $C_1$-$C_{30}$ alkoxy group, and the benzyl group may be substituted with at least one Rq, $R_1$ and $R_2$ may be joined together to form an aliphatic ring, an aliphatic hetero ring, an aromatic ring, or an aromatic hetero ring or to form a spiro bond, in which the rings may optionally have at least one substituent;

$R_3$ is $C_3$-$C_{20}$ acyl group, substituted $C_3$-$C_{20}$ acyl group, cyano group or sulfonyl group;

$R_4$ is H, substituted or unsubstituted amino group, $C_1$-$C_{20}$ acyl group or substituted $C_1$-$C_{20}$ acyl group; and $R_p$ is H or a prodrug functional group, wherein the prodrug functional group is —$PO_3H_2$, —$HPO_3^-Na^+$, —$PO_3^{2-}Na_2^+$, —$PO_3^{2-}K_2^+$, —$PO_3^{2-}Mg^{2+}$, $PO_3^{2-}Ca^{2+}$,

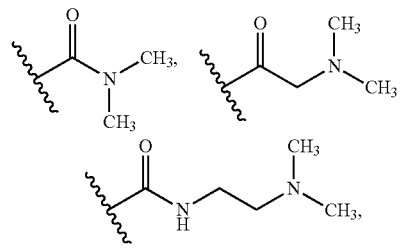

wherein Rq is H, at least one $C_1$-$C_{10}$ alkyl, substituted $C_1$-$C_{10}$ alkyl, $C_1$-$C_{10}$ cycloalkyl, substituted $C_1$-$C_{10}$ cycloalky, amino, substituted amino, $C_1$-$C_{10}$ alkoxy, substituted $C_1$-$C_{10}$ alkoxy, halogen, —OH, benzyl, substituted benzyl, acyl, substituted acyl, phenyl, substituted phenyl, butyl oxy carbonyl (BOC),

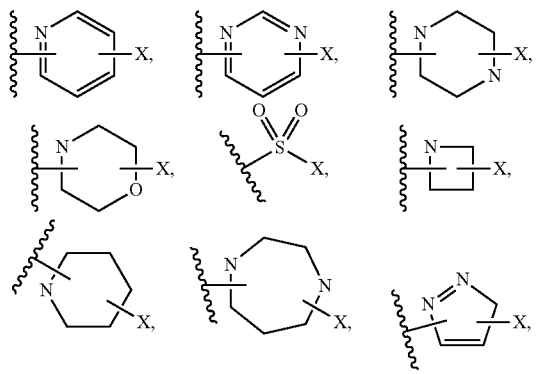

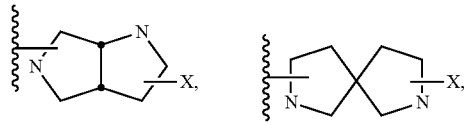

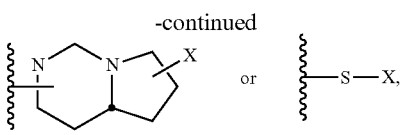

wherein X is H, at least one $C_1$-$C_{10}$ alkyl, substituted $C_1$-$C_{10}$ alkyl, acyl, $C_3$-$C_{10}$ cycloalkyl, $C_1$-$C_{10}$ alkoxy, phenyl, substituted phenyl, benzyl, substituted benzyl, a $C_1$-$C_{10}$ hetero aromatic ring, $C_3$-$C_{10}$ heterocycloalkyl, substituted $C_3$-$C_{10}$ heterocycloalkyl, amino, substituted amino, or —OH, wherein the $C_3$-$C_{10}$ heterocycloalkyl and the substituted $C_3$-$C_{10}$ heterocycloalkyl contain one or two heteroatoms wherein each heteroatom is independently selected from N and O, and wherein the substituted $C_3$-$C_{10}$ heterocycloalkyl is methyl substituted $C_3$-$C_{10}$ heterocycloalkyl, methoxy substituted $C_3$-$C_{10}$ heterocycloalkyl, or

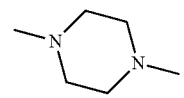

substituted $C_3$-$C_{10}$ heterocycloalkyl.

2. The compound or pharmaceutically acceptable salt thereof of claim 1, wherein $R_a$ is $C_1$-$C_6$ alkyl group or $C_2$-$C_6$ alkenyl group; and $R_p$ is H.

3. The compound or pharmaceutically acceptable salt thereof of claim 1, wherein $R_a$ is a methyl group.

4. The compound or pharmaceutically acceptable salt thereof of claim 1, wherein $R_b$ is selected from the group consisting of

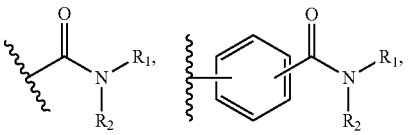

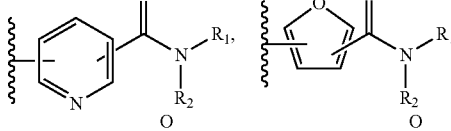

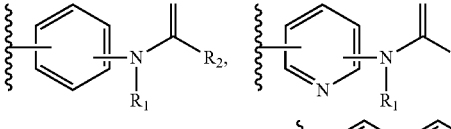

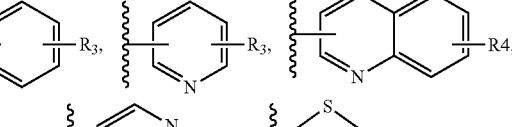

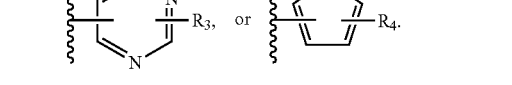

5. The compound or pharmaceutically acceptable salt thereof of claim 1,
wherein $R_1$ is H or $C_1$-$C_5$ alkyl group, and the $C_1$-$C_5$ alkyl group may be substituted with at least one Rq;

$R_2$ is H, $C_1$-$C_{10}$ alkyl group, $C_3$-$C_{10}$ cycloalkyl group, amino group, $C_1$-$C_{10}$ alkoxy group, benzyl group,

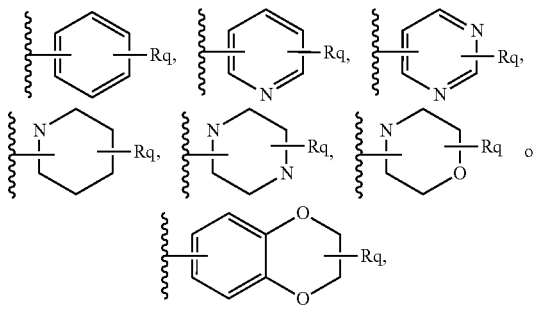

and the $C_1$-$C_{10}$ alkyl group, the $C_3$-$C_{10}$ cycloalkyl group, the amino group, the $C_1$-$C_{10}$ alkoxy group, and the benzyl group may be substituted with at least one Rq, $R_1$ and $R_2$ may be fused with N, thus forming any one ring selected from the group consisting of

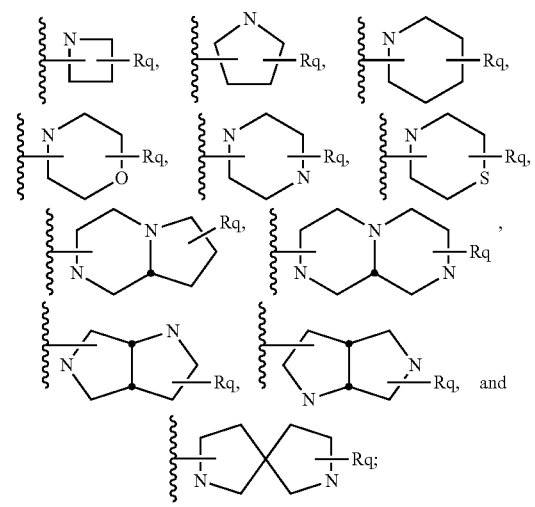

$R_3$ is

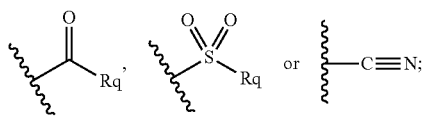

and $R_4$ is H, amino group substituted with at least one Rq,

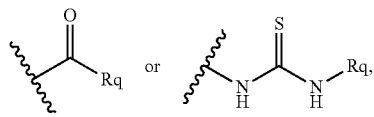

wherein Rq is H, at least one $C_1$-$C_{10}$ alkyl, substituted $C_1$-$C_{10}$ alkyl, $C_1$-$C_{10}$ cycloalkyl, substituted $C_1$-$C_{10}$ cycloalkyl, amino, substituted amino, $C_1$-$C_{10}$ alkoxy, substituted $C_1$-$C_{10}$ alkoxy, halogen, —OH, benzyl, substituted benzyl, acyl, substituted acyl, phenyl, substituted phenyl, butyl oxy carbonyl (BOC),

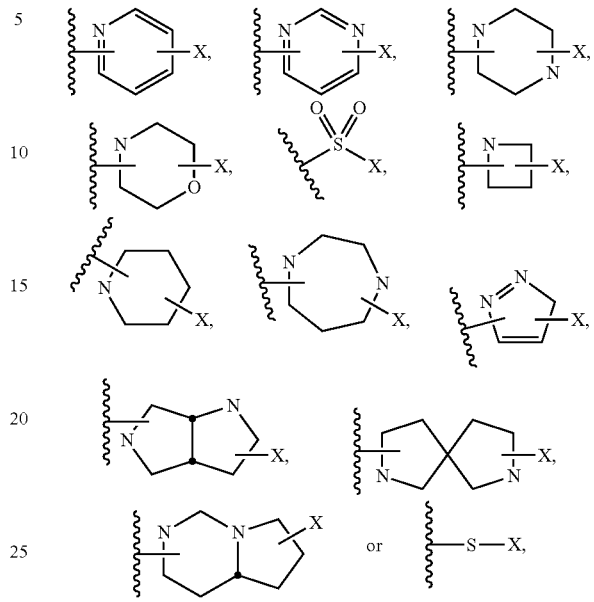

wherein X is H, at least one $C_1$-$C_{10}$ alkyl, substituted $C_1$-$C_{10}$ alkyl, acyl, $C_3$-$C_{10}$ cycloalkyl, $C_1$-$C_{10}$ alkoxy, phenyl, substituted phenyl, benzyl, substituted benzyl, a $C_1$-$C_{10}$ hetero aromatic ring, $C_3$-$C_{10}$ heterocycloalkyl, substituted $C_3$-$C_{10}$ heterocycloalkyl, amino, substituted amino, or —OH, wherein the $C_3$-$C_{10}$ heterocycloalkyl and the substituted $C_3$-$C_{10}$ heterocycloalkyl contain one or two heteroatoms wherein each heteroatom is independently selected from N and O, wherein the substituted $C_3$-$C_{10}$ heterocycloalkyl is methyl substituted $C_3$-$C_{10}$ heterocycloalkyl, methoxy substituted $C_3$-$C_{10}$ heterocycloalkyl, or

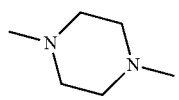

substituted $C_3$-$C_{10}$ heterocycloalkyl.

6. The compound or pharmaceutically acceptable salt thereof of claim 1, which is a compound (Compound E-5) represented by

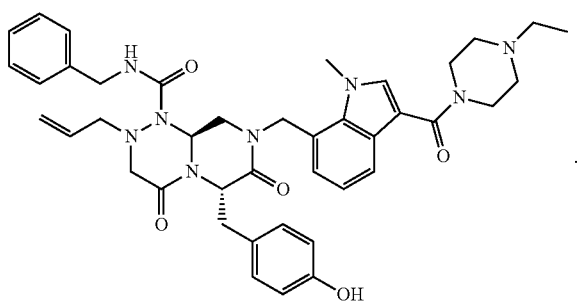 [SMILES: C=CCN1CC(=O)N2[C@@H](Cc3ccc(O)cc3)C(=O)N(Cc3cccc4c(C(=O)N5CCN(CC)CC5)cn(C)c34)C[C@@H]2N1C(=O)NCc1ccccc1]

7. A method of treating cancer comprising administering to a subject in need thereof a pharmaceutical composition comprising a compound or a pharmaceutically acceptable salt thereof according to claim 1, wherein the cancer is acute myeloid leukemia.

8. A method of treating cancer comprising administering to a subject in need thereof an injectable pharmaceutical composition comprising a compound or a pharmaceutically acceptable salt thereof according to claim 1, wherein the cancer is acute myeloid leukemia.

* * * * *